(12) United States Patent
Webster et al.

(10) Patent No.: US 8,642,621 B2
(45) Date of Patent: Feb. 4, 2014

(54) (4-PHENYL-PIPERIDIN-1-YL)-[5-(1H-PYRAZOL-4-YL)-THIOPHEN-3-YL]-METHANONE COMPOUNDS AND THEIR USE

(75) Inventors: Scott Peter Webster, Edinburgh (GB); Jonathan Robert Seckl, Edinburgh (GB); Brian Robert Walker, Edinburgh (GB); Peter Ward, Pinner (GB); Thomas David Pallin, Harlow (GB); Hazel Joan Dyke, Harlow (GB); Trevor Robert Perrior, Bury St Edmunds (GB)

(73) Assignee: The University Of Edinburgh, Edinburgh (GB)

(*) Notice: Subject to any disclaimer, the term of this patent is extended or adjusted under 35 U.S.C. 154(b) by 17 days.

(21) Appl. No.: 13/395,963

(22) PCT Filed: Sep. 14, 2010

(86) PCT No.: PCT/GB2010/001732
§ 371 (c)(1),
(2), (4) Date: Mar. 14, 2012

(87) PCT Pub. No.: WO2011/033255
PCT Pub. Date: Mar. 24, 2011

(65) Prior Publication Data
US 2012/0172393 A1    Jul. 5, 2012

Related U.S. Application Data

(60) Provisional application No. 61/242,825, filed on Sep. 16, 2009.

(51) Int. Cl.
*A61K 31/451* (2006.01)
*C07D 409/00* (2006.01)

(52) U.S. Cl.
USPC .......................................... 514/326; 546/213

(58) Field of Classification Search
None
See application file for complete search history.

(56) References Cited

U.S. PATENT DOCUMENTS

| | | | |
|---|---|---|---|
| 5,087,631 | A | 2/1992 | Shaffer |
| 6,340,678 | B1 | 1/2002 | Matsuhisa |
| 8,299,063 | B2 | 10/2012 | Webster et al. |
| 8,362,008 | B2 | 1/2013 | Webster et al. |
| 2006/0111366 | A1 | 5/2006 | Andersen |
| 2007/0117800 | A1 | 5/2007 | Arnold |
| 2007/0203154 | A1* | 8/2007 | Zhou et al. |
| 2010/0197662 | A1 | 8/2010 | Ogawa |
| 2010/0267696 | A1 | 10/2010 | Webster |
| 2011/0015178 | A1 | 1/2011 | Webster |
| 2012/0095046 | A1 | 4/2012 | Webster |
| 2013/0012545 | A1 | 1/2013 | Webster et al. |
| 2013/0123268 | A1 | 5/2013 | Webster et al. |

FOREIGN PATENT DOCUMENTS

| | | |
|---|---|---|
| EP | 1894919 A1 | 3/2008 |
| WO | WO 98/39325 A1 | 9/1998 |
| WO | WO 00/51608 A1 | 9/2000 |
| WO | WO 03/044009 A1 | 5/2003 |
| WO | WO 2004/016617 A1 | 2/2004 |
| WO | WO 2005/046685 A1 | 5/2005 |
| WO | WO 2005/047250 A1 | 5/2005 |
| WO | WO 2005/121145 A2 | 12/2005 |
| WO | WO 2006/132197 A1 | 12/2006 |
| WO | WO 2007/053776 A1 | 5/2007 |
| WO | WO 2007/082808 A2 | 7/2007 |
| WO | WO 2008/011453 A2 | 1/2008 |
| WO | WO 2008/103185 | 8/2008 |
| WO | WO 2009/074789 A1 | 6/2009 |
| WO | WO 2009/090239 A1 | 7/2009 |
| WO | WO 2009/112845 A1 | 9/2009 |
| WO | WO 2010/023161 A1 | 3/2010 |
| WO | WO 2010/146338 A1 | 12/2010 |
| WO | WO 2011/033255 A1 | 3/2011 |
| WO | WO 2011/135276 A1 | 11/2011 |

OTHER PUBLICATIONS

IPRP mailed Oct. 30, 2012 in PCT/GB2011/000345.
ISR and WOISA mailed May 4, 2011 in PCT/GB2011/000345.
Andrews, R.C., et al., 2003, "Effects of the 11β-hydroxysteroid dehydrogenase inhibitor carbenoxolone on insulin sensitivity in men with type 2 diabetes," *J. Clin. Endocrinol. Metab.*, vol. 88, pp. 285-291.
Christy, C., et al., 2003, "11β-hydroxysteroid dehydrogenase type 2 in mouse aorta; Localization and influence on response to glucocorticoids," *Hypertension*, vol. 42, pp. 580-587.
Cooper, M.S., et al., Sep. 2000, "Expression and functional consequences of 11β-hydroxysteroid dehydrogenase activity in human bone," *Bone*, vol. 27(3), pp. 375-381.
Gotthardt, H., 1971, "1.3-Dipolare Cycloadditionen Mit 1.3.2-Oxathiazolium-5-oxiden. Ein Neuer Weg in Die 5-Aryl-Isothiazol-Reihe", *Tetrahedron Letters*, No. 17, pp. 1281-1284.
Hadoke, P.W.F., et al., 2001, "Endothelial cell dysfunction in mice after transgenic knockout of type 2, but not type 1, 11β-hydroxysteroid dehydrogenase," *Circulation*, vol. 104, pp. 2832-2837.

(Continued)

*Primary Examiner* — Savitha Rao
*Assistant Examiner* — Gregg Polansky
(74) *Attorney, Agent, or Firm* — Swanson & Bratschun, L.L.C.

(57) ABSTRACT

The present invention pertains generally to the field of therapeutic compounds. More specifically the present invention pertains to certain (4-phenyl-piperidin-1-yl)-[5-(1H-pyrazol-4-yl)-thiophen-3-yl]-methanone compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

30 Claims, No Drawings

(56) References Cited

OTHER PUBLICATIONS

Hwang et al., 2001, "4-Hydroxy-6-oxo-6,7-dihydro-thieno[2,3-b]pyrimidine derivatives: synthesis and their biological evaluation for the glycine site acting on the N-methyl-D-aspartate (NMDA) receptor", *Archives of Pharmacol. Research*, vol. 24, No. 4, pp. 270-275.

Kotelevtsev, Y.V., et al., Dec. 1997, "11β-Hydroxysteroid dehydrogenase type 1 knockout mice show attenuated glucocorticoid inducible responses and resist hyperglycaemia on obesity and stress," *Proc. Natl. Acad. Sci.*, vol. 94, pp. 14924-14929.

Masuzaki, H., et al., 2001, "A Transgenic Model of Visceral Obesity and the Metabolic Syndrome," *Science*, vol. 294, pp. 2166-2170.

Moisan, M. P., et al., 1990, "11β-hydroxysteroid dehydrogenase bioactivity and messenger RNA expression in rat forebrain: localization in hypothalamus, hippocampus, and cortex," *Endocrinology*, vol. 127(3), pp. 1450-1455.

Morton, N.M., et al., Nov. 2, 2001, "Improved lipid and lipoprotein profile, hepatic insulin sensitivity, and glucose tolerance in 11β-hydroxysteroid dehydrogenase type 1 null mice," *J. Biol. Chem.*, vol. 276(44), pp. 41293-41300.

Morton, N.M., et al., Apr. 2004, "Novel adipose tissue-mediated resistance to diet-induced visceral obesity in 11β-hydroxysteroid dehydrogenase type 1 deficient mice," *Diabetes*, vol. 53, pp. 931-938.

Patani, G.A., et al., 1996, "Bioisosterism: A rational approach in drug design", *American Chemical Society*, vol. 96, pp. 3147-3176.

Paterson, J.M., et al., May 4, 2004, "Metabolic syndrome without obesity: hepatic overexpression of 11β-hydroxysteroid dehydrogenase type 1 in transgenic mice," *Proc. Natl. Acad. Sci.*, vol. 101(18), pp. 7088-7093).

Rask, E., et al., 2001, "Tissue-specific dysregulation of cortisol metabolism in human obesity," *J. Clin. Endocrinol. Metab.*, vol. 86(3), pp. 1418-1421.

Rauz, S., et al., 2001, "Expression and putative role of 11β-hydroxysteroid dehydrogenase isozymes within the human eye," *Investigative Opthalmology & Visual Science*, vol. 42(9), pp. 2037-2042.

Sandeep, T.C., et al., Apr. 27, 2004, "11β-hydroxysteroid dehydrogenase inhibition improves cognitive function in healthy elderly men and type 2 diabetics," *Proc. Natl. Acad. Sci.*, vol. 101(17), pp. 6734-6739.

Seckl, J.R., Walker, B.R., 2001, "11β-Hydroxysteroid dehydrogenase type 1—a tissue-specific amplifier of glucocorticoid action," *Endocrinology*, vol. 142(4), pp. 1371-1376.

Small, G.R., et al., Aug. 23, 2005, "Preventing local regeneration of glucocorticoids by 11β-hydroxysteroid dehydrogenase type 1 enhances angiogenesis," *Proc. Natl. Acad. Sci.*, vol. 102(34), pp. 12165-12170.

Stimson, R.H., et al., 2010, "Extra-adrenal cortisol production in obese men with type two diabetes mellitus—how big is the therapeutic target for 11βHSD1 inhibitors?" 92nd Annual Meeting of the Endocrine Society, San Diego, USA.

Walker, B.R., et al., 1991, "11β-Hydroxysteroid dehydrogenase in vascular smooth muscle and heart: implications for cardiovascular responses to glucocorticoids," *Endocrinology*, vol. 129(6), pp. 3305-3312.

Walker, B.R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, vol. 80(11), pp. 3155-3139.

Yau, J.L.W., et al., Apr. 10, 2001, "Lack of tissue glucocorticoid reactivation in 11β-hydroxysteroid dehydrogenase type 1 knockout mice ameliorates age-related learning impairments," *Proc. Natl. Acad. Sci.*, vol. 98(8), pp. 4716-4721.

GB Search Report for UK Patent Appln No. 0724251.4, Issued Mar. 27, 2008.
ISR and WOISA for PCT/GB2008/004068, Issued Feb. 6, 2009.
IPRP for PCT/GB2008/004068, Issued Jun. 15, 2010.
GB Search Report for UK Patent Appin No. 0804685.6, Issued Jul. 10, 2008.
ISR and WOISA for PCT/GB2009/000686, Issued Jun. 5, 2009.
IPRP for PCT/GB2009/000686, Issued Sep. 14, 2010.
ISR and WOISA for PCT/GB2010/001155, Issued Sep. 28, 2010.
IPRP for PCT/GB2010/001155, issued Dec. 16, 2011.
IPRP for PCT/GB2010/001732, issued Mar. 20, 2012.
ISR and WOISA for PCT/GB2010/001732, issued Mar. 20, 2012.
Registry No. 717867-57-7, entered STN Jul. 28, 2004.
Registry No. 717867-85-1, entered STN Jul. 28, 2004.
Registry No. 727385-01-5, entered STN Aug. 16, 2004.

* cited by examiner

(4-PHENYL-PIPERIDIN-1-YL)-[5-(1H-PYRAZOL-4-YL)-THIOPHEN-3-YL]-METHANONE COMPOUNDS AND THEIR USE

RELATED APPLICATION

This application is a 35 U.S.C. §371 national phase application of PCT/GB2010/001732, filed Sep. 14, 2010 (WO 2011/033255), entitled "(4-phenyl-piperidin-1-yl)-[5-(1H-pyrazol-4-yl)-thiophen-3-yl]-methanone Compounds and Their Use", related to United States provisional patent application number 61/242,825 filed Sep. 16, 2009, the contents of which are incorporated herein by reference in their entirety.

TECHNICAL FIELD

The present invention pertains generally to the field of therapeutic compounds. More specifically the present invention pertains to certain (4-phenyl-piperidin-1-yl)-[5-(1H-pyrazol-4-yl)-thiophen-3-yl]-methanone compounds that, inter alfa, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Glucocorticoids (cortisol in man, corticosterone in rodents) are hormones that regulate a range of pathways involved in stress and metabolic signalling. They are antagonists of insulin action and impair insulin-dependent glucose uptake, increase lipolysis, and enhance hepatic gluconeogenesis. These effects are evident in Cushing's syndrome, which is caused by elevated circulating levels of glucocorticoids. The features of Cushing's syndrome are diverse and reflect the tissue distribution of glucocorticoid receptors in the body. They include a cluster of metabolic (central/visceral obesity, insulin resistance, hyperglycaemia, dyslipidaemia) and cardiovascular (hypertension) abnormalities which, when observed in patients without Cushing's syndrome, constitute the metabolic syndrome. These abnormalities confer a substantial risk of cardiovascular disease. In addition, Cushing's syndrome is associated with neuropsychiatric manifestations including depression and cognitive impairment. The features of Cushing's syndrome are reversible upon removal of the cause of glucocorticoid excess.

It is recognised that glucocorticoid activity is controlled at the tissue level by the intracellular conversion of active cortisol and inactive cortisone by 11β-hydroxysteroid dehydrogenases (see, e.g., Seckl et al., 2001). These enzymes exist in two distinct isoforms. 11β-HSD1, which catalyses the reaction that activates cortisone, is expressed in liver, adipose tissue, brain, skeletal muscle, vascular smooth muscle and other organs, while, 11β-HSD2, which inactivates cortisol, is predominantly expressed in the kidney. Pharmacological inhibition of 11β-HSD1 in rat and man with carbenoxolone (see, e.g., Walker et al., 1995), and transgenic knockout in mice (see, e.g., Kotelevtsev et al., 1997), results in enhanced hepatic insulin sensitivity and reduced gluconeogenesis and glycogenolysis, suggesting that 11β-HSD1 inhibition will be a useful treatment in type 2 diabetes and other insulin resistance syndromes. Furthermore, mice lacking 11β-HSD1 possess low triglycerides, increased HDL cholesterol, and increased apo-lipoprotein A-I levels (see, e.g., Morton et al., 2001), suggesting that inhibitors of 11β-HSD1 may be of utility in the treatment of atherosclerosis.

The link between 11β-HSD1 and the metabolic syndrome has been strengthened by studies in transgenic mice and man. 11β-HSD1 knockout mice on two different genetic backgrounds are protected from dietary obesity (see, e.g., Morton et al., 2004), while administration of carbenoxolone to patients with type 2 diabetes enhances insulin sensitivity (see, e.g., Andrews et al., 2003). However, it has become apparent that the key tissue in which 11β-HSD1 exerts the greatest influence upon metabolic disease is the adipose tissue rather than the liver. Mice with transgenic overexpression of 11β-HSD1 in adipose tissue (see, e.g. Masuzaki et al., 2001) have a more profound metabolic syndrome and obesity than mice with overexpression in liver (see, e.g., Paterson et al., 2004). In obese humans, 11β-HSD1 activity is increased in adipose tissue, but enzyme activity is decreased in the liver (see, e.g., Rask et al., 2001).

In the CNS, 11β-HSD1 is highly expressed in regions important for cognition such as hippocampus, frontal cortex, and cerebellum (see, e.g., Moisan et al., 1990). Elevated cortisol is associated with cognitive dysfunction, and glucocorticoids have a range of neurotoxic effects. 11β-HSD1 knockout mice are protected against age-related cognitive dysfunction (see, e.g., Yau et al., 2001), while administration of the 11β-HSD inhibitor carbenoxolone has been shown to enhance cognitive function in elderly men and type 2 diabetics who have a selective impairment in verbal memory (see, e.g., Sandeep et al., 2004). Thus, 11β-HSD1 inhibitors are of potential therapeutic utility in the treatment of diseases such as Alzheimer's Disease, which are characterised by cognitive impairment.

The isozymes of 11β-HSD are also expressed in the blood vessel wall (see, e.g., Walker et al., 1991; Christy et al., 2003). 11β-HSD1 is expressed in vascular smooth muscle, while 11β-HSD2 is expressed in endothelial cells where it modulates endothelial-dependent vasodilation (see, e.g., Hadoke et al., 2001). 11β-HSD1 knockout mice have normal vascular function, but they exhibit enhanced angiogenesis in response to inflammation or ischaemia (see, e.g., Small et al., 2005). This offers therapeutic potential in the treatment of myocardial infarction, since inhibition of 11β-HSD1 may enhance revascularisation of ischaemic tissues.

Studies have shown that 11β-HSD1 affects intraocular pressure in man (see, e.g., Rauz et al., 2001). Inhibition of 11β-HSD1 may be useful in reducing intraocular pressure in the treatment of glaucoma.

Glucocorticoids are involved in the regulation of bone formation and skeletal development. Treatment of healthy volunteers with carbenoxolone led to a decrease in bone resorption markers suggesting that 11β-HSD1 plays a role in bone resorption (see, e.g., Cooper et al., 2000). 11β-HSD1 inhibitors could be used as protective agents in the treatment of osteoporosis.

Certain compounds that inhibit 11β-hydroxysteroid dehydrogenase type 1 (11β-HSD1) that are useful in the treatment, control, and/or prevention of disorders (e.g., diseases) that are responsive to the inhibition of 11β-HSD1 are described in international (PCT) patent application number PCT/GB2009/000686 filed 13 Mar. 2009 (published as WO 2009/112845 A1 on 17 Sep. 2009).

Certain compounds of the following formula which allegedly inhibit 11β-HSD1, and allegedly are useful in the treatment and prevention of diseases such as metabolic diseases, in particular, diabetes type 2, obesity, and dyslipidemia, are described in WO 2010/023161 A1 (published on 4 Mar. 2010).

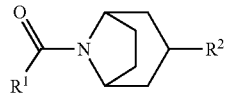

The inventors have discovered an especially preferred class of compounds, which inhibit 11β-hydroxysteroid dehydrogenase type 1 (11β-HSD1), and which additionally have improved pharmacokinetic and/or microsomal stability properties, and which are useful in the treatment, control, and/or prevention of disorders (e.g., diseases) that are responsive to the inhibition of 11β-HSD1.

SUMMARY OF THE INVENTION

One aspect of the invention pertains to certain (4-phenyl-piperidin-1-yl)-[5-(1H-pyrazol-4-yl)-thiophen-3-yl]-methanone compounds (referred to herein as PPPT compounds), as described herein.

Another aspect of the invention pertains to a composition (e.g., a pharmaceutical composition) comprising a PPPT compound, as described herein, and a pharmaceutically acceptable carrier or diluent.

Another aspect of the invention pertains to a method of preparing a composition (e.g., a pharmaceutical composition) comprising the step of admixing a PPPT compound, as described herein, and a pharmaceutically acceptable carrier or diluent.

Another aspect of the present invention pertains to a method of inhibiting 11β-hydroxysteroid dehydrogenase type 1 (11β-HSD1) function (e.g., in a cell), in vitro or in vivo, comprising contacting the cell with an effective amount of a PPPT compound, as described herein.

Another aspect of the present invention pertains to a method of treatment comprising administering to a subject in need of treatment a therapeutically-effective amount of a PPPT compound, as described herein, preferably in the form of a pharmaceutical composition.

Another aspect of the present invention pertains to a PPPT compound as described herein for use in a method of treatment of the human or animal body by therapy.

Another aspect of the present invention pertains to use of a PPPT compound, as described herein, in the manufacture of a medicament for use in treatment.

In one embodiment, the treatment is treatment or prevention of a disorder (e.g., a disease) that is ameliorated by the inhibition of 11β-hydroxysteroid dehydrogenase type 1 (11β-HSD1).

In one embodiment, the treatment is treatment or prevention of metabolic syndrome, which includes conditions such as type 2 diabetes and obesity, and associated disorders including insulin resistance, hypertension, lipid disorders and cardiovascular disorders such as ischaemic (coronary) heart disease.

In one embodiment, the treatment is treatment or prevention of a CNS disorder (e.g., a CNS disease) such as mild cognitive impairment and early dementia, including Alzheimer's disease.

Another aspect of the present invention pertains to a kit comprising (a) a PPPT compound, as described herein, preferably provided as a pharmaceutical composition and in a suitable container and/or with suitable packaging; and (b) instructions for use, for example, written instructions on how to administer the compound.

Another aspect of the present invention pertains to a PPPT compound obtainable by a method of synthesis as described herein, or a method comprising a method of synthesis as described herein.

Another aspect of the present invention pertains to a PPPT compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain (4-phenyl-piperidin-1-yl)-[5-(1H-pyrazol-4-yl)-thiophen-3-yl]-methanone compounds (for convenience, collectively referred to herein as "PPPT compounds"), which are related to the following compound:

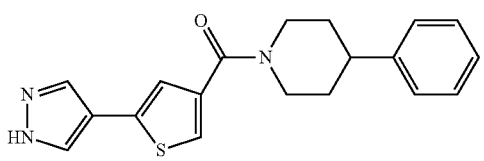 [SMILES: O=C(c1csc(-c2cn[nH]c2)c1)N1CCC(c2ccccc2)CC1]

(4-Phenyl-piperidin-1-yl)-[5-(1H-pyrazol-4-yl)-
thiophen-3-yl]-methanone

Some embodiments of the invention include the following:
(1) A compound selected from compounds of the following formula, and pharmaceutically acceptable salts, hydrates, and solvates thereof:

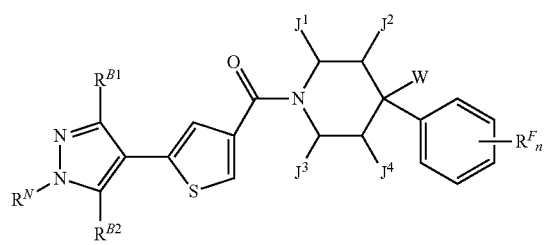

wherein:
—W is independently —H or —Y;
—Y is independently —$Y^1$, —$Y^2$, —$Y^3$, —$Y^4$, or —$Y^5$;
—$Y^1$ is independently —OH;
—$Y^2$ is independently —$Y^{2A}$, —$Y^{2B}$, or —$Y^{2C}$;
—$Y^3$ is independently —$Y^{3A}$, —$Y^{3B}$, or —$Y^{3C}$;
—$Y^4$ is independently —F, —Cl, —Br, or —I;
—$Y^5$ is independently —CN;
wherein:
—$Y^{2A}$ is independently —$OR^{YA}$;
—$Y^{2B}$ is independently —$OR^{YB}$;
—$Y^{2C}$ is independently —$OR^{YC}$;
—$Y^{3A}$ is independently —$R^{YA}$;
—$Y^{3B}$ is independently —$R^{YB}$;
—$Y^{3C}$ is independently —$R^{YC}$;
wherein:
each —$R^{YA}$ is independently saturated aliphatic $C_{1-6}$alkyl;
each —$R^{YB}$ is independently saturated aliphatic halo-$C_{1-6}$alkyl;
each —$R^{YC}$ is independently saturated aliphatic hydroxy-$C_{1-6}$alkyl;
and wherein:
each of -$J^1$, -$J^2$, -$J^3$, and -$J^4$ is —H;
or each of -$J^2$ and -$J^4$ is —H; and -$J^1$ and -$J^3$ taken together form —$CH_2$— or —$CH_2CH_2$—;
or each of -$J^1$ and -$J^3$ is —H; and -$J^2$ and -$J^4$ taken together form —$CH_2$— or —$CH_2CH_2$—;
or each of -$J^2$ and -$J^3$ is —H; and -$J^1$ and -$J^4$ taken together form —$CH_2$— or —$CH_2CH_2$—;
and wherein:
—$R^N$ is independently —H or —$R^{NN}$;
—$R^{NN}$ is independently saturated aliphatic $C_{1-6}$alkyl;
and wherein:
—$R^{B1}$ is independently —H or —$R^{BB}$;
—$R^{B2}$ is independently —H or —$R^{BB}$;
wherein:
each —$R^{BB}$ is independently —$R^{BB1}$, —$R^{BB2}$, or —$R^{BB3}$;
wherein:
each —$R^{BB1}$ is independently saturated aliphatic $C_{1-6}$alkyl, and is optionally substituted with one or more substituents selected from —F, —OH, —$OR^{BBB}$, —$OCH_2F$, —$OCHF_2$, —$OCF_3$, —$NH_2$, —$NHR^{BBB}$, and —$NR^{BBB}_2$; wherein each —$R^{BBB}$ is independently saturated aliphatic $C_{1-4}$alkyl;
each —$R^{BB2}$ is independently —F, —Cl, —Br, or —I;
each —$R^{BB3}$ is independently —CN;
and wherein:
n is independently 0, 1, 2, 3, 4, or 5;
each —$R^F$ is independently —$R^Z$, —F, —Cl, —Br, —I, —$CF_3$, —OH, —$OR^Z$, —$OCF_3$, —$SR^Z$, —$S(=O)_2R^Z$, or —CN; and
each —$R^Z$ is independently saturated aliphatic $C_{1-6}$alkyl, and is optionally substituted with one or more substituents selected from —F, —Cl, —OH, —$OR^{ZZ}$, —$OCH_2F$, —$OCHF_2$, and —$OCF_3$; wherein each —$R^{ZZ}$ is independently saturated aliphatic $C_{1-4}$alkyl;
with the proviso that the compound is not (4-phenyl-piperidin-1-yl)-[5-(1H-pyrazol-4-yl)-thiophen-3-yl]-methanone or a pharmaceutically acceptable salt, hydrate, or solvate thereof.

For the avoidance of doubt, it is not intended that the pyrazole ring (shown on the far left of the above formula) is fused to any other rings. For example, it is not intended that —$R^N$ and —$R^{B2}$, together with the atoms to which they are attached, form a ring.

The Proviso

For convenience, the compound (4-phenyl-piperidin-1-yl)-[5-(1H-pyrazol-4-yl)-thiophen-3-yl]-methanone, which is the subject of the proviso, is shown below. It appears as Compound EE-60 at page 59 of WO 2009/112845 A1.

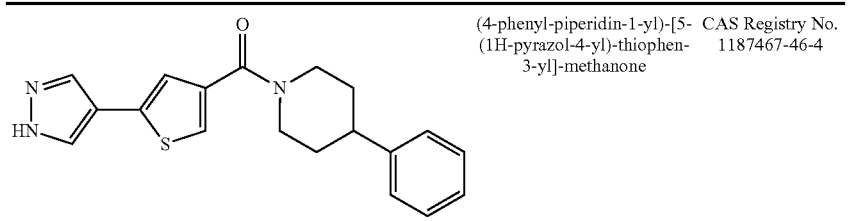

| | |
|---|---|
| (4-phenyl-piperidin-1-yl)-[5-(1H-pyrazol-4-yl)-thiophen-3-yl]-methanone | CAS Registry No. 1187467-46-4 |

The Group —W
(2) A compound according to (1), wherein —W is independently —Y.
(3) A compound according to (1), wherein —W is independently —H.

The Group —Y
(4) A compound according to any one of (1) to (3), wherein —Y, if present, is independently —$Y^1$, —$Y^2$, —$Y^3$, or —$Y^4$.
(5) A compound according to any one of (1) to (3), wherein —Y, if present, is independently —$Y^1$, $Y^2$, or $Y^3$.

(6) A compound according to any one of (1) to (3), wherein —Y, if present, is independently —Y$^1$ or —Y$^2$.

(7) A compound according to any one of (1) to (3), wherein —Y, if present, is independently —Y$^1$.

(8) A compound according to any one of (1) to (3), wherein —Y, if present, is independently —Y$^2$.

(9) A compound according to any one of (1) to (3), wherein —Y, if present, is independently —Y$^3$.

(10) A compound according to any one of (1) to (3), wherein —Y, if present, is independently —Y$^4$.

(11) A compound according to any one of (1) to (3), wherein —Y, if present, is independently —Y$^5$.

The Group —Y$^2$

(12) A compound according to any one of (1) to (11), wherein —Y$^2$, if present, is independently —Y$^{2A}$ or —Y$^{2B}$.

(13) A compound according to any one of (1) to (11), wherein —Y$^2$, if present, is independently —Y$^{2A}$.

(14) A compound according to any one of (1) to (11), wherein —Y$^2$, if present, is independently —Y$^{2B}$.

(15) A compound according to any one of (1) to (11), wherein —Y$^2$, if present, is independently —Y$^{2C}$.

The Group —Y$^3$

(16) A compound according to any one of (1) to (15), wherein —Y$^3$, if present, is independently —Y$^{3A}$ or —Y$^{3A}$.

(17) A compound according to any one of (1) to (15), wherein —Y$^3$, if present, is independently —Y$^{3A}$.

(18) A compound according to any one of (1) to (15), wherein —Y$^3$, if present, is independently —Y$^{3B}$.

(19) A compound according to any one of (1) to (15), wherein —Y$^3$, if present, is independently —Y$^{3C}$.

The Group —Y$^4$

(20) A compound according to any one of (1) to (19), wherein —Y$^4$, if present, is independently —F, —Cl, or —Br.

(21) A compound according to any one of (1) to (19), wherein —Y$^4$, if present, is independently —F or —Cl.

(22) A compound according to any one of (1) to (19), wherein —Y$^4$, if present, is independently —F.

(23) A compound according to any one of (1) to (19), wherein —Y$^4$, if present, is independently —Cl.

(24) A compound according to any one of (1) to (19), wherein —Y$^4$, if present, is independently —Br.

(25) A compound according to any one of (1) to (19), wherein —Y$^4$, if present, is independently —I.

The Group —R$^{YA}$

(26) A compound according to any one of (1) to (25), wherein each —R$^{YA}$, if present, is independently saturated aliphatic C$_{1-4}$alkyl.

(27) A compound according to any one of (1) to (25), wherein each —R$^{YA}$, if present, is independently -Me, -Et, -nPr, -iPr, -nBu, -iBu, or -tBu.

(28) A compound according to any one of (1) to (25), wherein each —R$^{YA}$, if present, is independently -Me, -Et, -nPr, or -iPr.

(29) A compound according to any one of (1) to (25), wherein each —R$^{YA}$, if present, is independently -Me or -Et.

(30) A compound according to any one of (1) to (25), wherein each —R$^{YA}$, if present, is independently -Me.

The Group —R$^{YB}$

(31) A compound according to any one of (1) to (30), wherein each —R$^{YB}$, if present, is independently saturated aliphatic halo-C$_{1-4}$alkyl.

(32) A compound according to any one of (1) to (30), wherein each —R$^{YB}$, if present, is independently —CF$_3$, —CHF$_2$, —CH$_2$F, —CH$_2$CF$_3$, —CH$_2$CHF$_2$, —CH$_2$CH$_2$F, or —CF$_2$CF$_3$.

(33) A compound according to any one of (1) to (30), wherein each —R$^{YB}$, if present, is independently —CF$_3$, —CHF$_2$, —CH$_2$F, or —CH$_2$CF$_3$.

(34) A compound according to any one of (1) to (30), wherein each —R$^{YB}$, if present, is independently —CF$_3$ or —CHF$_2$.

(35) A compound according to any one of (1) to (30), wherein each —R$^{YB}$, if present, is independently —CF$_3$.

The Group —R$^{YC}$

(36) A compound according to any one of (1) to (35), wherein each —R$^{YC}$, if present, is independently saturated aliphatic hydroxy-C$_{1-4}$alkyl.

(37) A compound according to any one of (1) to (35), wherein each —R$^{YC}$, if present, is independently —CH$_2$OH, —CH$_2$CH$_2$OH, —CH$_2$CH$_2$CH$_2$OH, —CH(CH$_3$)$_2$OH, or —CH$_2$CH$_2$CH$_2$CH$_2$OH.

(38) A compound according to any one of (1) to (35), wherein each —R$_{YC}$, if present, is independently —CH$_2$OH, —CH$_2$CH$_2$OH, —CH$_2$CH$_2$CH$_2$OH, or —CH$_2$CH$_2$CH$_2$CH$_2$OH.

(39) A compound according to any one of (1) to (35), wherein each —R$^{YC}$, if present, is independently —CH$_2$OH, —CH$_2$CH$_2$OH or —CH$_2$CH$_2$CH$_2$OH.

(40) A compound according to any one of (1) to (35), wherein each —R$^{YC}$, if present, is independently —CH$_2$OH.

The Group -J-

(41) A compound according to any one of (1) to (40), wherein each of -J$^1$, -J$^2$, -J$^3$, and -J$^4$ is —H.

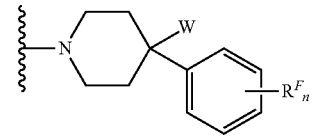

(42) A compound according to any one of (1) to (40), wherein each of -J$^2$ and -J$^4$ is —H; and -J$^1$ and -J$^3$ taken together form —CH$_2$— or —CH$_2$CH$_2$—.

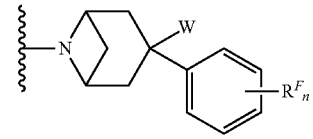

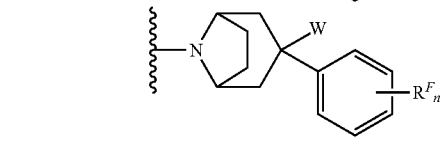

(43) A compound according to any one of (1) to (40), wherein each of -J$^2$ and -J$^4$ is —H; and -J$^1$ and -J$^3$ taken together form —CH$_2$—.

(44) A compound according to any one of (1) to (40), wherein each of -J$^2$ and -J$^4$ is —H; and -J$^1$ and -J$^3$ taken together form —CH$_2$CH$_2$—.

(45) A compound according to any one of (1) to (40), wherein each of -J$^1$ and -J$^3$ is —H; and -J$^2$ and -J$^4$ taken together form —CH$_2$— or —CH$_2$CH$_2$—.

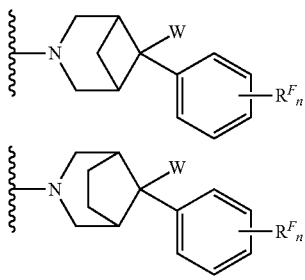

(46) A compound according to any one of (1) to (40), wherein each of -J$^1$ and -J$^3$ is —H; and -J$^2$ and -J$^4$ taken together form —CH$_2$—.

(47) A compound according to any one of (1) to (40), wherein each of -J$^1$ and -J$^3$ is —H; and -J$^2$ and -J$^4$ taken together form —CH$_2$CH$_2$—.

(48) A compound according to any one of (1) to (40), wherein each of -J$^2$ and -J$^3$ is —H; and -J$^1$ and -J$^4$ taken together form —CH$_2$— or —CH$_2$CH$_2$—.

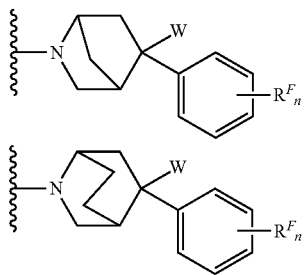

(49) A compound according to any one of (1) to (40), wherein each of -J$^2$ and -J$^3$ is —H; and -J$^1$ and -J$^4$ taken together form —CH$_2$—.

(50) A compound according to any one of (1) to (40), wherein each of -J$^2$ and -J$^3$ is —H; and -J$^1$ and -J$^4$ taken together form —CH$_2$CH$_2$—.

The Group —R$^N$

(51) A compound according to any one of (1) to (50), wherein —R$^N$ is independently —H.

(52) A compound according to any one of (1) to (50), wherein —R$^N$ is independently —R$^{NN}$.

The Group —R$^{NN}$

(53) A compound according to any one of (1) to (52), wherein —R$^{NN}$, if present, is independently saturated aliphatic C$_{1-4}$alkyl.

(54) A compound according to any one of (1) to (52), wherein —R$^{NN}$, if present, is independently -Me, -Et, -nPr, -iPr, -nBu, -iBu, or -tBu.

(55) A compound according to any one of (1) to (52), wherein —R$^{NN}$, if present, is independently -Me or -Et.

The Groups —R$^{B1}$ and —R$^{B2}$

(56) A compound according to any one of (1) to (55), wherein:
—R$^{B1}$ is independently —H or —R$^{BB}$; and
—R$^{B2}$ is independently —H.

(57) A compound according to any one of (1) to (55), wherein:
—R$^{B1}$ is independently —H; and
—R$^{B2}$ is independently —H or —R$^{BB}$.

(58) A compound according to any one of (1) to (55), wherein:
—R$^{B1}$ is independently —H; and
—R$^{B2}$ is independently —H.

(59) A compound according to any one of (1) to (55), wherein:
—R$^{B1}$ is independently —R$^{BB}$; and
—R$^{B2}$ is independently —R$^{BB}$.

The Group —R$^{BB}$

(60) A compound according to any one of (1) to (59), wherein each —R$^{BB}$, if present, is independently —R$^{BB1}$ or —R$^{BB2}$.

(61) A compound according to any one of (1) to (59), wherein each —R$^{BB}$, if present, is independently —R$^{BB1}$ or —R$^{BB3}$.

(62) A compound according to any one of (1) to (59), wherein each —R$^{BB}$, if present, is independently —R$^{BB2}$ or —R$^{BB}$.

(63) A compound according to any one of (1) to (59), wherein each —R$^{BB}$, if present, is independently —R$^{BB}$.

(64) A compound according to any one of (1) to (59), wherein each —R$^{BB}$, if present, is independently —R$^{BB2}$.

(65) A compound according to any one of (1) to (59), wherein each —R$^{BB}$, if present, is independently —R$^{BB3}$.

The Group —R$^{BB1}$

(66) A compound according to any one of (1) to (65), wherein each —R$^{BB1}$, if present, is independently saturated aliphatic C$_{1-4}$alkyl, and is optionally substituted with one or more substituents selected from —F, —OH, —OR$^{BBB}$, —OCH$_2$F, —OCHF$_2$, —OCF$_3$, —NH$_2$, —NHR$^{BBB}$, and —NR$^{BBB}$$_2$.

(67) A compound according to any one of (1) to (65), wherein each —R$^{BB1}$, if present, is independently saturated aliphatic C$_{1-4}$alkyl, and is optionally substituted with one or more substituents selected from —F, —OH, —OR$^{BBB}$, —OCH$_2$F, —OCHF$_2$, and —OCF$_3$.

(68) A compound according to any one of (1) to (65), wherein each —R$^{BB1}$, if present, is independently saturated aliphatic C$_{1-4}$alkyl, and is optionally substituted with one or more substituents selected from —F, —OH, and —OR$^{BBB}$.

(69) A compound according to any one of (1) to (65), wherein each —R$^{BB1}$, if present, is independently unsubstituted saturated aliphatic C$_{1-4}$alkyl.

(70) A compound according to any one of (1) to (65), wherein each —R$^{BB1}$, if present, is independently -Me, -Et, -nPr, -iPr, -nBu, -iBu, or -tBu.

(71) A compound according to any one of (1) to (65), wherein each —R$^{BB1}$, if present, is independently -Me or -Et.

(72) A compound according to any one of (1) to (65), wherein each —R$^{BB1}$, if present, is independently -Me.

The Group —R$^{BB2}$

(73) A compound according to any one of (1) to (72), wherein each —R$^{BB2}$, if present, is independently —F, —Cl, or —Br.

(74) A compound according to any one of (1) to (72), wherein each —R$^{BB2}$, if present, is independently —F or —Cl.

(75) A compound according to any one of (1) to (72), wherein each —R$^{BB2}$, if present, is independently —F.

(76) A compound according to any one of (1) to (72), wherein each —R$^{BB2}$, if present, is independently —Cl.

The Group —R$^{BBB}$

(77) A compound according to any one of (1) to (76), wherein each —R$^{BBB}$, if present, is independently -Me, -Et, -nPr, -iPr, -nBu, -iBu, or -tBu.

(78) A compound according to any one of (1) to (76), wherein each —R$^{BBB}$, if present, is independently -Me or -Et.

The Index n

(79) A compound according to any one of (1) to (78), wherein n is independently 0, 1, 2, or 3.

(80) A compound according to any one of (1) to (78), wherein n is independently 0, 1, or 2.

(81) A compound according to any one of (1) to (78), wherein n is independently 0 or 1.

(82) A compound according to any one of (1) to (78), wherein n is independently 0.

(83) A compound according to any one of (1) to (78), wherein n is independently 1, 2, or 3.

(84) A compound according to any one of (1) to (78), wherein n is independently 1 or 2.

(85) A compound according to any one of (1) to (78), wherein n is independently 1.

(86) A compound according to any one of (1) to (78), wherein n is independently 2.

(87) A compound according to any one of (1) to (78), wherein n is independently 3.

(88) A compound according to any one of (1) to (78), wherein n is independently 4.

(89) A compound according to any one of (1) to (78), wherein n is independently 5.

The Group —$R^F$

(90) A compound according to any one of (1) to (89), wherein each —$R^F$, if present, is independently —$R^Z$, —F, —Cl, —Br, —I, —$CF_3$, —OH, —$OR^Z$, —$OCF_3$, —$SR^Z$, —$S(=O)_2R^Z$, or —CN.

(91) A compound according to any one of (1) to (89), wherein each —$R^F$, if present, is independently —F, —Cl, -Me, -Et, —OH, —OMe, —OEt, —$CF_3$, —$OCF_3$, or —CN.

(92) A compound according to any one of (1) to (89), wherein each —$R^F$, if present, is independently —F, —Cl, —$CF_3$, —OMe, or —CN.

(93) A compound according to any one of (1) to (89), wherein each —$R^F$, if present, is independently —F, —Cl, or —$CF_3$.

The Group —$R^Z$

(94) A compound according to any one of (1) to (93), wherein each —$R^Z$, if present, is independently saturated aliphatic $C_{1-4}$alkyl, and is optionally substituted with one or more substituents selected from —F, —Cl, —OH, —$OR^{ZZ}$, —$OCH_2F$, —$OCHF_2$, and —$OCF_3$.

(95) A compound according to any one of (1) to (93), wherein each —$R^Z$, if present, is independently saturated aliphatic $C_{1-4}$alkyl, and is optionally substituted with one or more substituents selected from —F, —Cl, —OH, and —$OR^{ZZ}$.

(96) A compound according to any one of (1) to (93), wherein each —$R^Z$, if present, is independently unsubstituted saturated aliphatic $C_{1-4}$alkyl.

(97) A compound according to any one of (1) to (93), wherein each —$R^Z$, if present, is independently -Me, -Et, -nPr, -iPr, -nBu, -iBu, or -tBu.

(98) A compound according to any one of (1) to (93), wherein each —$R^Z$, if present, is independently -Me or -Et.

The Group —$R^{ZZ}$

(99) A compound according to any one of (1) to (90), (94), and (95), wherein each —$R^{ZZ}$, if present, is independently -Me, -Et, -nPr, -iPr, -nBu, -iBu, or -tBu.

(100) A compound according to any one of (1) to (90), (94), and (95), wherein each —$R^{ZZ}$, if present, is independently -Me or -Et.

Some Preferred Substituted Phenyl Groups (101) A compound according to any one of (1) to (78), wherein the group:

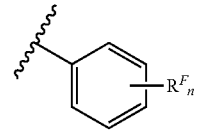

is:

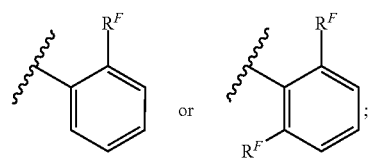

wherein:
each —$R^F$ is independently —$R^Z$, —F, —Cl, —Br, —I, —$CF_3$, —OH, —$OR^Z$, —$OCF_3$, —$SR^Z$, —$S(=O)_2R^Z$, or —CN; and each —$R^Z$ is independently saturated aliphatic $C_{1-4}$alkyl, and is optionally substituted with one or more substituents selected from —F, —Cl, —OH, —$OR^{ZZ}$, —$OCH_2F$, —$OCHF_2$, and —$OCF_3$; wherein each —Ru is independently saturated aliphatic $C_{1-4}$alkyl.

(102) A compound according to (101), wherein each —$R^F$, if present, is independently —$R^Z$, —F, —Cl, —Br, —I, —$CF_3$, —OH, —$OR^Z$, —$OCF_3$, or —CN.

(103) A compound according to (101), wherein each —$R^F$, if present, is independently —F, —Cl, -Me, -Et, —OH, —OMe, —OEt, —$CF_3$, —$OCF_3$, or —CN.

(104) A compound according to (101), wherein each —$R^F$, if present, is independently —F, —Cl, —$CF_3$, —OMe, or —CN.

(105) A compound according to (101), wherein each —$R^F$, if present, is independently —F, —Cl, or —$CF_3$.

(106) A compound according to (101), wherein each —$R^F$, if present, is independently —F, —Cl, or -Me.

(107) A compound according to (101) or (102), wherein each —$R^Z$, if present, is independently saturated aliphatic $C_{1-4}$alkyl, and is optionally substituted with one or more substituents selected from —F, —Cl, —OH, —$OR^{ZZ}$, —$OCH_2F$, —$OCHF_2$, and —$OCF_3$.

(108) A compound according to (101) or (102), wherein each —$R^Z$, if present, is independently saturated aliphatic $C_{1-4}$alkyl, and is optionally substituted with one or more substituents selected from —F, —OH, and —$OR^{ZZ}$.

(109) A compound according to (101) or (102), wherein each —$R^Z$, if present, is independently unsubstituted saturated aliphatic $C_{1-4}$alkyl.

(110) A compound according to (101) or (102), wherein each —$R^Z$, if present, is independently -Me, -Et, -nPr, -iPr, -nBu, -iBu, or -tBu.

(111) A compound according to (101) or (102), wherein each —$R^Z$, if present, is independently -Me or -Et.

(112) A compound according to any one of (101), (102), (107), and (108), wherein each —Ru, if present, is independently -Me, -Et, -nPr, -iPr, -nBu, -iBu, or -tBu.

(113) A compound according to any one of (101), (102), (107), and (108), wherein each —$R^{ZZ}$, if present, is independently -Me or -Et.

Molecular Weight (114) A compound according to any one of (1) to (113), wherein has a molecular weight of from 337 to 1200.

(115) A compound according to (114), wherein the bottom of the range is 350, 360, 375, 400, or 425.

(116) A compound according to (114) or (115), wherein the top of the range is 1100, 1000, 900, 800, 700, 600, 500, or 450.

(117) A compound according to any one of (1) to (113), wherein the compound has a molecular weight of from 350 to 450.

Examples of Some Specific Embodiments (118) A compound according to (1), selected from compounds of the following formulae and pharmaceutically acceptable salts, hydrates, and solvates thereof:

| Compound No. | Synthesis No. | Structure |
|---|---|---|
| AA-01 | 1 | 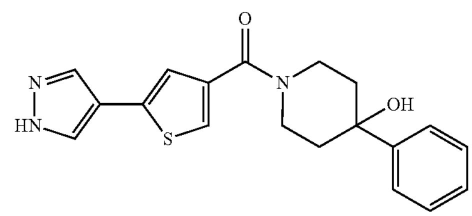 |
| AA-02 | 1 | 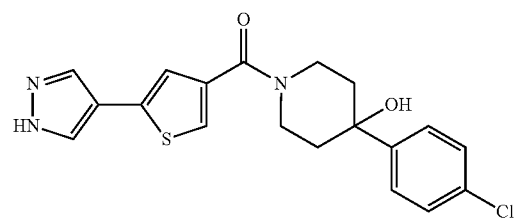 [SMILES: O=C(c1csc(-c2cn[nH]c2)c1)N1CCC(O)(c2ccc(Cl)cc2)CC1] |
| AA-03 | 1 | 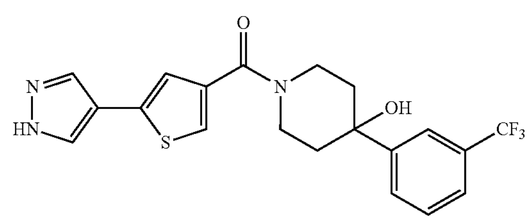 [SMILES: O=C(c1csc(-c2cn[nH]c2)c1)N1CCC(O)(c2cccc(C(F)(F)F)c2)CC1] |
| AA-04 | 1 | 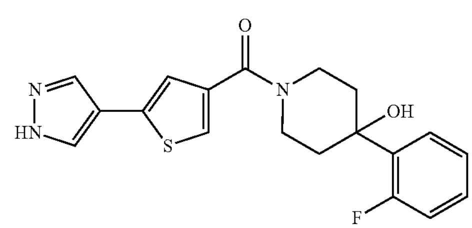 [SMILES: O=C(c1csc(-c2cn[nH]c2)c1)N1CCC(O)(c2ccccc2F)CC1] |
| AA-05 | 1 | 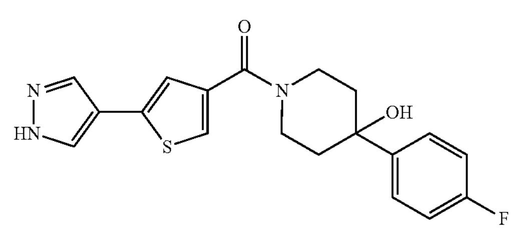 [SMILES: O=C(c1csc(-c2cn[nH]c2)c1)N1CCC(O)(c2ccc(F)cc2)CC1] |

-continued
| Compound No. | Synthesis No. | Structure |
|---|---|---|
| AA-06 | 1 | 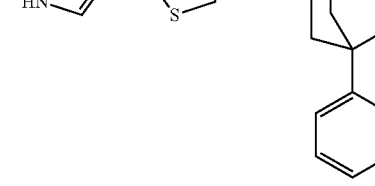 |
| AA-07 | 1 | 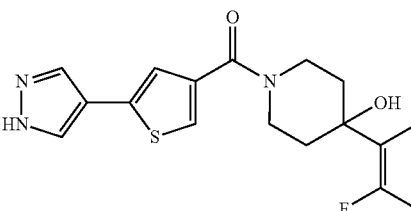 |
| AA-08 | 1 | 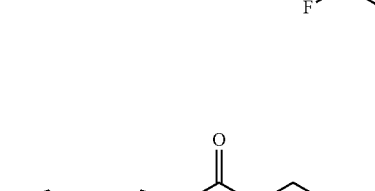 |
| AA-09 | 1 | 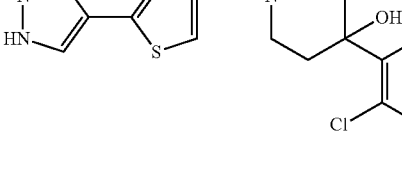 |
| AA-10 | 1 | 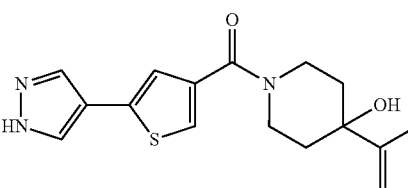 |
| AA-11 | 1 | 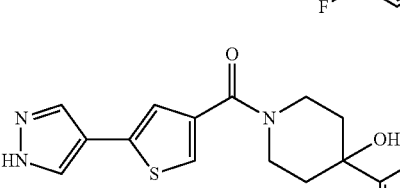 |

-continued
| Compound No. | Synthesis No. | Structure |
|---|---|---|
| AA-12 | 1 | 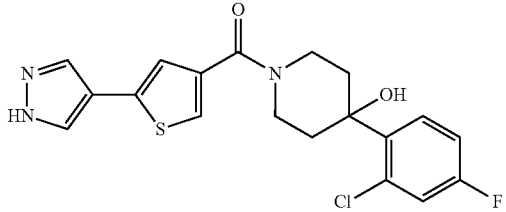 [SMILES: O=C(c1csc(-c2cn[nH]c2)c1)N1CCC(O)(c2ccc(F)cc2Cl)CC1] |
| AA-13 | 1 | 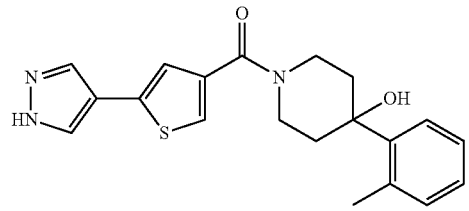 [SMILES: Cc1ccccc1C1(O)CCN(C(=O)c2csc(-c3cn[nH]c3)c2)CC1] |
| AA-14 | 1 | 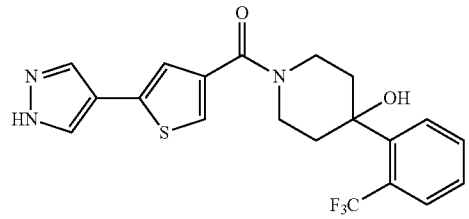 |
| AA-15 | 1 | 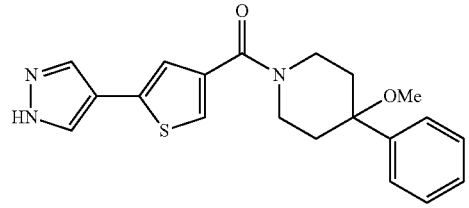 |
| AA-16 | 1 | 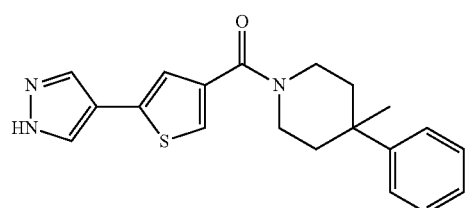 |
| AA-17 | 1 | 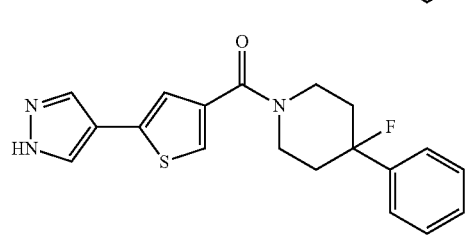 |
| AA-18 | 1 | 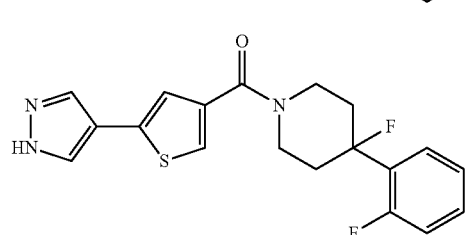 |

-continued

| Compound No. | Synthesis No. | Structure |
|---|---|---|
| AA-19 | 1 | 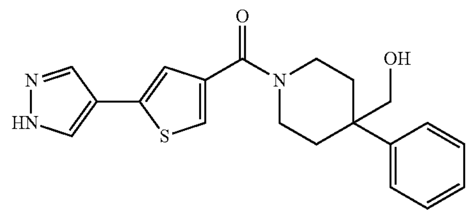 [SMILES: O=C(c1csc(-c2cn[nH]c2)c1)N1CCC(CO)(c2ccccc2)CC1] |
| AA-20 | 1 | 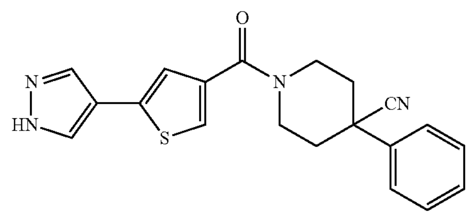 [SMILES: N#CC1(c2ccccc2)CCN(C(=O)c2csc(-c3cn[nH]c3)c2)CC1] |
| AA-21 | 1 | 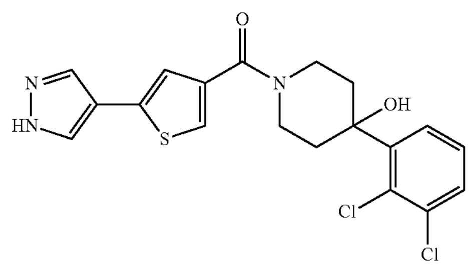 [SMILES: O=C(c1csc(-c2cn[nH]c2)c1)N1CCC(O)(c2cccc(Cl)c2Cl)CC1] |
| AA-22 | 1 | 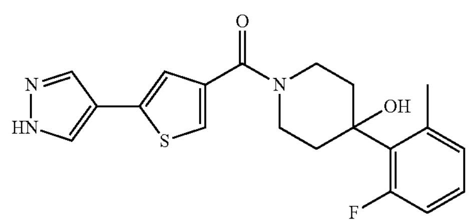 [SMILES: Cc1cccc(F)c1C1(O)CCN(C(=O)c2csc(-c3cn[nH]c3)c2)CC1] |
| AA-23 | 1 | 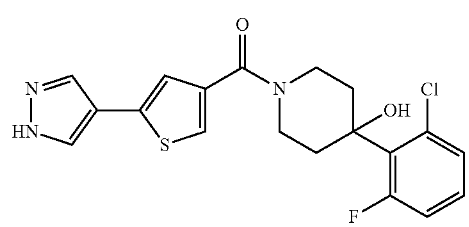 [SMILES: O=C(c1csc(-c2cn[nH]c2)c1)N1CCC(O)(c2c(F)cccc2Cl)CC1] |
| AA-24 | 1 | 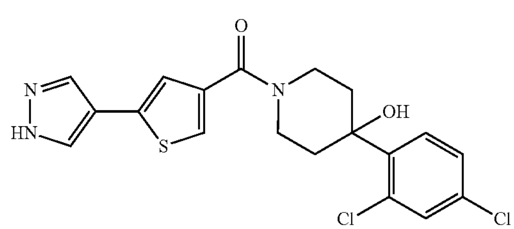 [SMILES: O=C(c1csc(-c2cn[nH]c2)c1)N1CCC(O)(c2ccc(Cl)cc2Cl)CC1] |

-continued
| Compound No. | Synthesis No. | Structure |
|---|---|---|
| AA-25 | 1 | 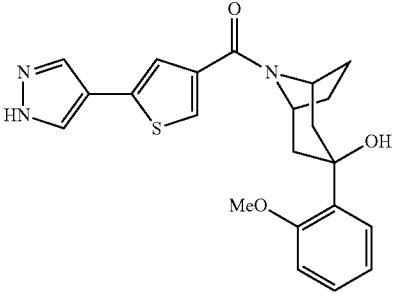 [SMILES: COc1ccccc1C1(O)CC2CCC(C1)N2C(=O)c1csc(-c2cn[nH]c2)c1] |
| AA-26 | 1 | 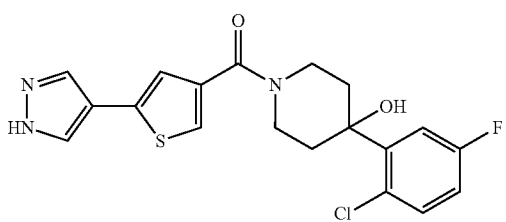 [SMILES: O=C(c1csc(-c2cn[nH]c2)c1)N1CCC(O)(c2cc(F)ccc2Cl)CC1] |
| AA-27 | 1 | 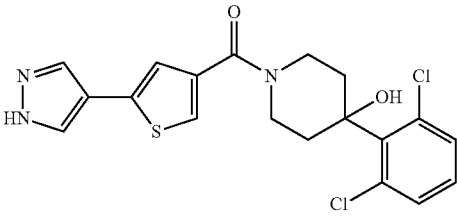 [SMILES: O=C(c1csc(-c2cn[nH]c2)c1)N1CCC(O)(c2c(Cl)cccc2Cl)CC1] |
| AA-28 | 1 | 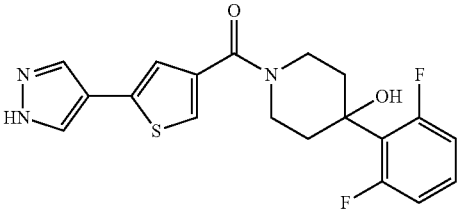 [SMILES: O=C(c1csc(-c2cn[nH]c2)c1)N1CCC(O)(c2c(F)cccc2F)CC1] |
| AA-29 | 1 | 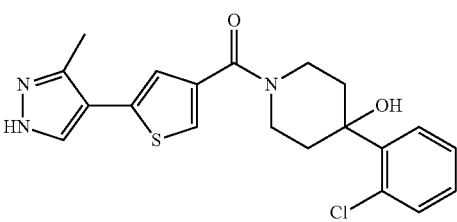 [SMILES: Cc1n[nH]cc1-c1cc(C(=O)N2CCC(O)(c3ccccc3Cl)CC2)cs1] |
| AA-30 | 1 | 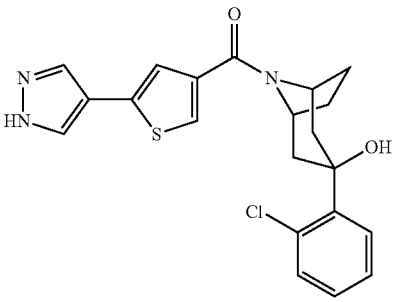 [SMILES: O=C(c1csc(-c2cn[nH]c2)c1)N1C2CCC1CC(O)(c1ccccc1Cl)C2] |

-continued
| Compound No. | Synthesis No. | Structure |
|---|---|---|
| AA-31 | 1 | 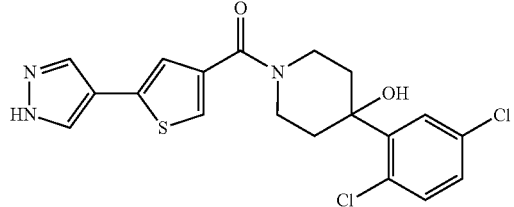 [SMILES: O=C(c1csc(-c2cn[nH]c2)c1)N1CCC(O)(c2cc(Cl)ccc2Cl)CC1] |
| AA-32 | 1 | 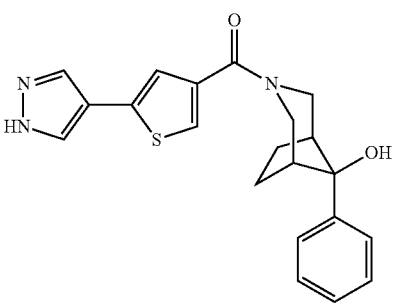 [SMILES: O=C(c1csc(-c2cn[nH]c2)c1)N1CC2CCC(C1)C2(O)c1ccccc1] |
| AA-33 | 1 | 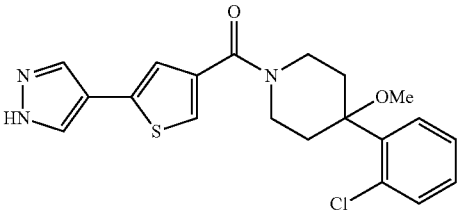 [SMILES: COC1(c2ccccc2Cl)CCN(C(=O)c2csc(-c3cn[nH]c3)c2)CC1] |
| AA-34 | 1 | 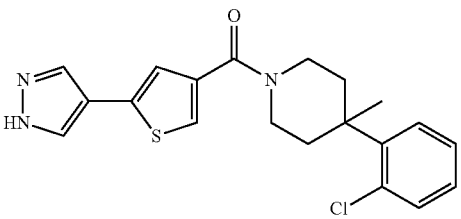 [SMILES: CC1(c2ccccc2Cl)CCN(C(=O)c2csc(-c3cn[nH]c3)c2)CC1] |
| AA-35 | 1 | 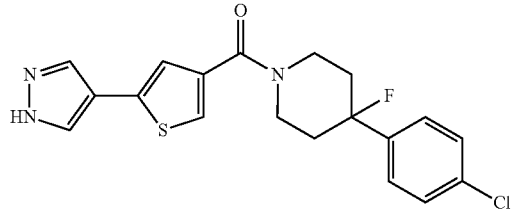 [SMILES: O=C(c1csc(-c2cn[nH]c2)c1)N1CCC(F)(c2ccc(Cl)cc2)CC1] |
| AA-36 | 1 | 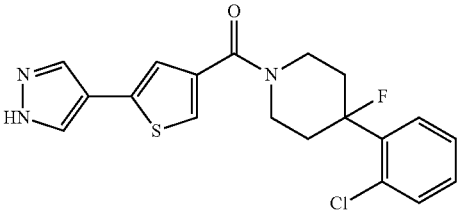 [SMILES: O=C(c1csc(-c2cn[nH]c2)c1)N1CCC(F)(c2ccccc2Cl)CC1] |

-continued
| Compound No. | Synthesis No. | Structure |
|---|---|---|
| AA-37 | 1 | 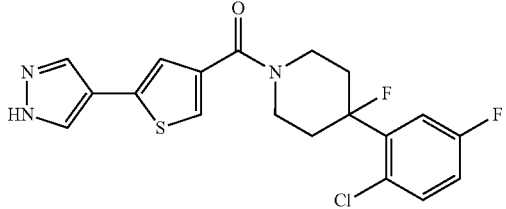 [SMILES: O=C(c1csc(-c2cn[nH]c2)c1)N1CCC(F)(c2cc(F)ccc2Cl)CC1] |
| AA-38 | 1 | 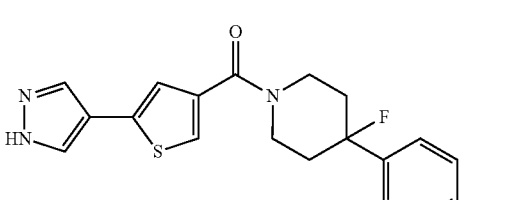 |
| AA-39 | 43 | 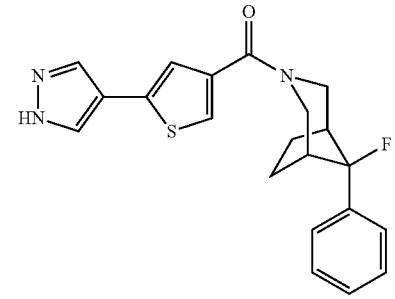 [SMILES: O=C(c1csc(-c2cn[nH]c2)c1)N1CC2CCC(C1)C2(F)c1ccccc1] |
| AA-40 | 1 | 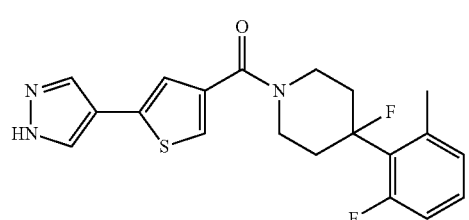 |
| AA-41 | 1 | 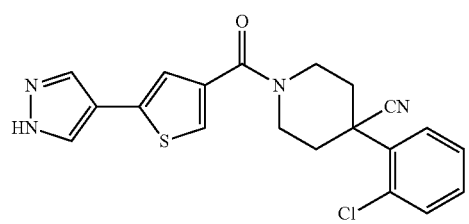 [SMILES: N#CC1(c2ccccc2Cl)CCN(C(=O)c2csc(-c3cn[nH]c3)c2)CC1] |

(119) A compound according to (1), selected from compounds of the following formulae and pharmaceutically acceptable salts, hydrates, and solvates thereof:
| Compound No. | Synthesis No. | Structure |
|---|---|---|
| BB-01 | 1 | 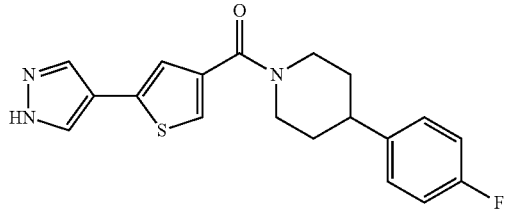 [SMILES: O=C(c1csc(-c2cn[nH]c2)c1)N1CCC(c2ccc(F)cc2)CC1] |
| BB-02 | 1 | 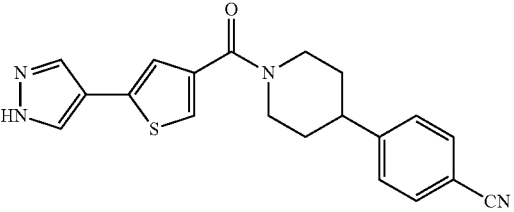 |
| BB-03 | 1 | 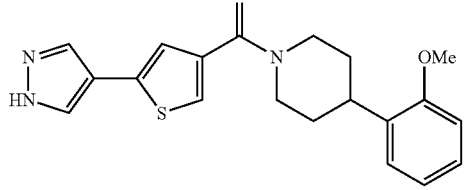 |
| BB-04 | 1 | 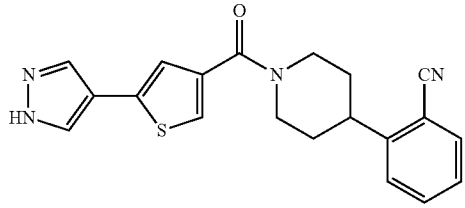 [SMILES: N#Cc1ccccc1C1CCN(C(=O)c2csc(-c3cn[nH]c3)c2)CC1] |
| BB-05 | 1 | 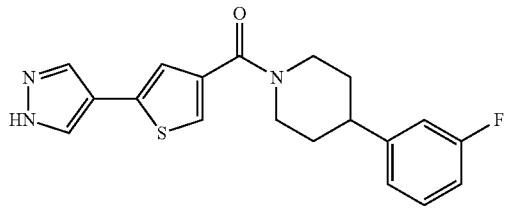 [SMILES: O=C(c1csc(-c2cn[nH]c2)c1)N1CCC(c2cccc(F)c2)CC1] |
| BB-06 | 1 | 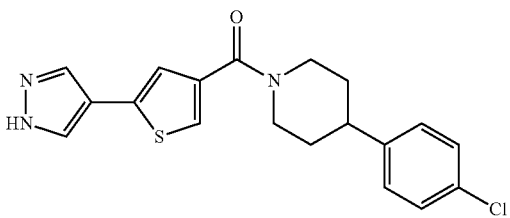 [SMILES: O=C(c1csc(-c2cn[nH]c2)c1)N1CCC(c2ccc(Cl)cc2)CC1] |

-continued
| Compound No. | Synthesis No. | Structure |
|---|---|---|
| BB-07 | 1 | 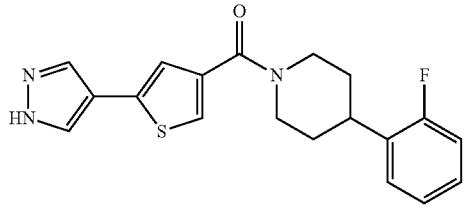 |
| BB-08 | 1 | 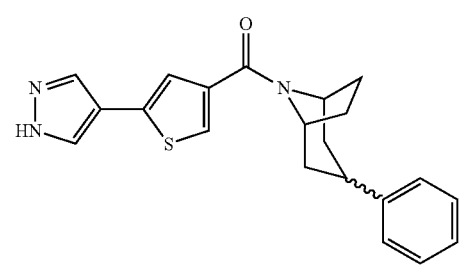 [SMILES: O=C(c1csc(-c2cn[nH]c2)c1)N1C2CCC1CC(c1ccccc1)C2] |
| BB-09 | 1 | 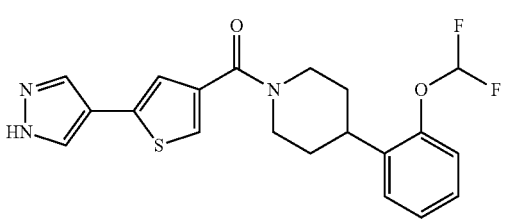 [SMILES: O=C(c1csc(-c2cn[nH]c2)c1)N1CCC(c2ccccc2OC(F)F)CC1] |
| BB-10 | 1 | 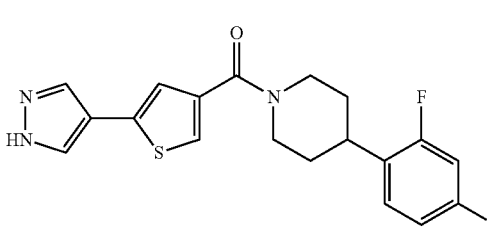 |
| BB-11 | 1 | 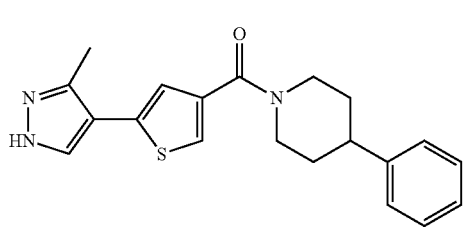 [SMILES: Cc1n[nH]cc1-c1cc(C(=O)N2CCC(c3ccccc3)CC2)cs1] |
| BB-12 | 1 | 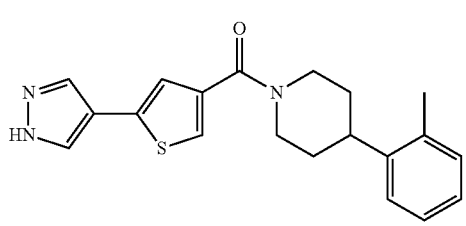 [SMILES: Cc1ccccc1C1CCN(C(=O)c2csc(-c3cn[nH]c3)c2)CC1] |
| BB-13 | 1 | 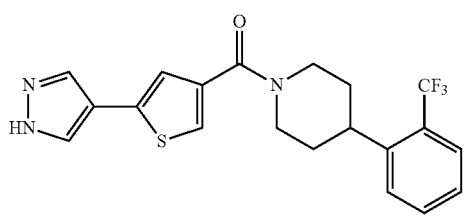 |

| Compound No. | Synthesis No. | Structure |
|---|---|---|
| BB-14 | 1 | 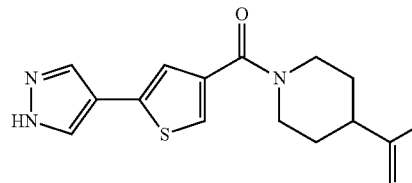 |
| BB-15 | 1 | 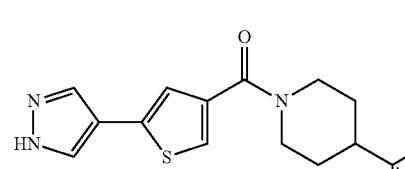 |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., —W, —Y, $Y^1$, —$Y^2$, —$Y^3$, —$Y^4$, —$Y^5$, —$Y^{2A}$, —$Y^{2B}$, —$Y^{2C}$, —$Y^{3A}$, —$Y^{3B}$, —$Y^{3C}$, —$R^{YA}$, —$R^{YB}$, —$R^{YC}$, -$J^1$, -$J^2$, -$J^3$, -$J^4$, —$R^N$, —$R^{NN}$, —$R^{B1}$, —$R^{B2}$, —$R^{BB}$, —$R^{BB1}$, —$R^{BB2}$, —$R^{BB3}$, —$R^{BBB}$, n, —$R^F$, —$R^Z$, —$R^{ZZ}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to PPPT compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate).

In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

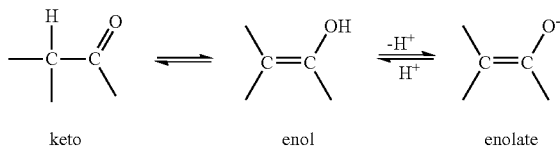

keto          enol          enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, —OAc).

For example, an aldehyde or ketone group may be protected as an acetal (R—CH(OR)$_2$) or ketal (R$^{2C}$(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyl amide (—NHCH$_2$C$_6$H$_5$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: a C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of PPPT compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising a PPPT compound, as described herein, and a pharmaceutically acceptable carrier, diluent, or excipient.

Another aspect of the present invention pertains to a method of preparing a composition (e.g., a pharmaceutical composition) comprising admixing a PPPT compound, as described herein, and a pharmaceutically acceptable carrier, diluent, or excipient.

Uses

The PPPT compounds, as described herein, are useful, for example, in the treatment of disorders (e.g., diseases) that are ameliorated by the inhibition of 11β-hydroxysteroid dehydrogenase type 1 (11β-HSD1), as described herein.

Use in Methods of Inhibiting 11β-Hydroxysteroid Dehydrogenase Type 1 (11β-HSD1)

One aspect of the present invention pertains to a method of inhibiting 11β-hydroxysteroid dehydrogenase type 1 in a cell, in vitro or in vivo, comprising contacting the cell with an effective amount of a PPPT compound, as described herein.

Suitable assays for determining 11β-hydroxysteroid dehydrogenase type 1 inhibition are described herein and/or are known in the art.

In one embodiment, the method is performed in vitro.

In one embodiment, the method is performed in vivo.

In one embodiment, the PPPT compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits 11β-hydroxysteroid dehydrogenase type 1. For example, suitable assays are described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a PPPT compound, as described herein, for use in a method of treatment of the human or animal body by therapy.

Use in the Manufacture of Medicaments

Another aspect of the present invention pertains to use of a PPPT compound, as described herein, in the manufacture of a medicament for use in treatment.

In one embodiment, the medicament comprises the PPPT compound.

Methods of Treatment

Another aspect of the present invention pertains to a method of treatment comprising administering to a patient in need of treatment a therapeutically effective amount of a PPPT compound, as described herein, preferably in the form of a pharmaceutical composition.

Disorders Treated—Disorders Ameliorated by the Inhibition of 11β-Hydroxysteroid Dehydrogenase Type 1

In one embodiment (e.g., of use in methods of therapy, of use in the manufacture of medicaments, of methods of treatment), the treatment is treatment or prevention of a disorder (e.g., a disease) that is ameliorated by the inhibition of 11β-hydroxysteroid dehydrogenase type 1.

Disorders Treated—Disorders Characterised by Up-Regulation of 11β-HSD1 etc.

In one embodiment (e.g., of use in methods of therapy, of use in the manufacture of medicaments, of methods of treatment), the treatment is treatment or prevention of a disorder (e.g., a disease) that is characterised by one or more of: up-regulation of 11β-HSD1; up-regulation of glucocorticoid receptor mediated pathways; elevated PEPCK levels; other biochemical markers pertaining to glucocorticoid excess and insulin resistance.

Disorders Treated

In one embodiment (e.g., of use in methods of therapy, of use in the manufacture of medicaments, of methods of treatment), the treatment is treatment or prevention of one or more of the following:

(1) Cushing's syndrome;
(2) type 2 diabetes and impaired glucose tolerance;
(3) insulin resistance syndromes such as myotonic dystrophy, Prader Willi, lipodystrophies, polycystic ovary syndrome, gastrointestinal diabetes, etc.;

(4) obesity and being overweight;
(5) lipid disorders including dyslipidaemia;
(6) atherosclerosis and its sequelae, including myocardial infarction and peripheral vascular disease;
(7) Metabolic Syndrome;
(8) steatohepatitis/fatty liver and non-alcoholic fatty liver disease;
(9) cognitive impairment in type 2 diabetes, glucose intolerance and ageing, and in psychotic disorders and pre-schizophrenia;
(10) dementias such as Alzheimer's disease, multi-infarct dementia, dementia with Lewy bodies, fronto-temporal dementia (including Pick's disease), progressive supranuclear palsy, Korsakoffs syndrome, Binswanger's disease, HIV-associated dementia, Creutzfeldt-Jakob disease (CJD), multiple sclerosis, motor neurone disease, Parkinson's disease, Huntington's disease, Niemann-Pick disease type C, normal pressure hydrocephalus, and Down's syndrome;
(11) mild cognitive impairment (cognitive impairment, no dementia);
(12) β-cell dysfunction in pancreatic disease;
(13) glaucoma;
(14) anxiety;
(15) depression and other affective disorders; typical (melancholic) and atypical depression; dysthymia; post-partum depression; bipolar affective disorder; drug-induced affective disorders; anxiety; posttraumatic stress disorder; panic; phobias;
(16) delirium and acute confusional state;
(17) inflammatory disease;
(18) osteoporosis;
(19) myocardial infarction, for example, to prevent left ventricular dysfunction after myocardial infarction; and
(20) stroke, for example, to limit ischaemic neuronal loss after cardiovascular accident.

In one embodiment (e.g., of use in methods of therapy, of use in the manufacture of medicaments, of methods of treatment), the treatment is treatment or prevention of one or more of the following:
(1) hyperglycaemia;
(2) glucose intolerance and impaired glucose tolerance;
(3) insulin resistance;
(4) hyperlipidaemia;
(5) hypertriglyceridaemia;
(6) hypercholesterolaemia;
(7) low HDL levels;
(8) high LDL levels;
(9) vascular restenosis;
(10) abdominal obesity;
(11) neurodegenerative disease;
(12) retinopathy;
(13) neuropathy;
(14) hypertension; and
(15) other diseases where insulin resistance is a component.

In one embodiment (e.g., of use in methods of therapy, of use in the manufacture of medicaments, of methods of treatment), the treatment is treatment or prevention of an adverse effect of glucocorticoids used to treat inflammatory diseases, such as asthma, chronic obstructive pulmonary disease, skin diseases, rheumatoid arthritis and other arthropathies, inflammatory bowel disease, and giant cell arthritis/polymyalgia rheumatica.

In one embodiment (e.g., of use in methods of therapy, of use in the manufacture of medicaments, of methods of treatment), the treatment is treatment or prevention of metabolic syndrome, which includes disorders such as type 2 diabetes and obesity, and associated disorders including insulin resistance, hypertension, lipid disorders and cardiovascular disorders such as ischaemic (coronary) heart disease.

In one embodiment (e.g., of use in methods of therapy, of use in the manufacture of medicaments, of methods of treatment), the treatment is treatment or prevention of a CNS disorder (e.g., a CNS disease) such as mild cognitive impairment and early dementia, including Alzheimer's disease.

Treatment

The term "treatment," as used herein in the context of treating a disorder, pertains generally to treatment and therapy, whether of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of metabolic syndrome, reducing the incidence of metabolic syndrome, alleviating the symptoms of metabolic syndrome, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the PPPT compounds described herein include the following:

(1) insulin and insulin analogues;
(2) insulin sensitising agents, for example: PPAR-γ agonists; PPAR-α agonists; PPAR-α/γ dual agonists; biguanides;
(3) incretin-based therapies and incretin mimetics;
(4) sulfonylureas and other insulin secretogogues;
(5) α-glucosidase inhibitors;
(6) glucagon receptor antagonists;
(7) GLP-1, GLP-1 analogues, and GLP-receptor agonists;
(8) GIP, GIP mimetics, and GIP receptor agonists;
(9) PACAP, PACAP mimetics, and PACAP receptor δ agonists;
(10) agents that suppress hepatic glucose output, such as metformin;
(11) agents designed to reduce the absorption of glucose from the intestine, such as acarbose;
(12) phosphotyrosine phosphatase 1B inhibitors;
(13) glucose 6-phosphatase inhibitors;
(14) glucokinase activators;
(15) glycogen phosphorylase inhibitors;
(16) fructose 1,6-biphosphatase inhibitors;
(17) SIRT1 activators;
(18) SGLT2 inhibitors;
(19) glutamine:fructose-6-phosphate amidotransferase inhibitors;
(20) anti-obesity agents, including: orilistat, pramlintide, sibutramine, fenfluramine, phentermine, dexfenfluramine, cannabinoid CB1 receptor antagonists or inverse agonists such as rimonobant, ghrelin antagonists, oxyntomodulin, neuropeptide $Y^1$ or $Y^5$ antagonists, 5-$HT_{1B}$ receptor agonists, 5-$HT_{2C}$ receptor agonists, 5-$HT_{1B/2C}$ receptor dual agonists, melanocortin receptor agonists, and melanin-concentrating hormone receptor antagonists, bupropion, naltrexone, topiramate, growth hormone analogues, and β3 agonists;
(21) anti-dyslipidaemia agents, including: HMG-CoA reductase inhibitors, PPAR-α agonists, PPAR-α/γ dual agonists, bile acid sequestrants, ileal bile acid absorption inhibitors, acyl CoA:cholesterol acyltransferase inhibitors, cholesterol absorption inhibitors, cholesterol ester transfer protein inhibitors, nicotinyl alcohol and its analogues, and anti-oxidants;
(22) anti-inflammatory agents, including: non-steroidal anti-inflammatory drugs such as aspirin; and steroidal anti-inflammatory agents such as hydrocortisone and dexamethasone;
(23) anti-hypertensive agents, including: β-blockers such as atenolol and inderal; calcium antagonists such as nifedipine; ACE inhibitors such as lisinopril, aptopril and captopril; angiotensin receptor antagonists such as candesartan, losartan and cilexetil; diuretic agents such as furosemide and benzthiazide; α-antagonists; centrally acting agents such as clonidine, methyl dopa, and indapamide; renin inhibitors; and vasodilators such as hydralazine;
(24) dipeptidyl peptidase IV (DPP-IV) inhibitors such as sitagliptin and saxagliptin;
(25) acetylcholinesterase inhibitors, including: donezepil hydrochloride, rivastigmine and galanthamine;
(26) NMDA receptor blockers, including memantine hydrochloride;
(27) Histamine H3 antagonists;
(28) 5-$HT_6$ receptor antagonists;
(29) α7 receptor agonists; and
(30) γ-secretase modulators, including tarenflurbil.

Other Uses

The PPPT compounds described herein may also be used as cell culture additives to inhibit 11β-hydroxysteroid dehydrogenase type 1 (11β-HSD1), etc.

The PPPT compounds described herein may also be used as part of an in vitro assay, for example, in order to determine whether a candidate host is likely to benefit from treatment with the compound in question.

The PPPT compounds described herein may also be used as a standard, for example, in an assay, in order to identify other active compounds, other 11β-hydroxysteroid dehydrogenase type 1 (11β-HSD1) inhibitors, etc.

Kits

One aspect of the invention pertains to a kit comprising (a) a PPPT compound as described herein, or a composition comprising a PPPT compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The PPPT compound or pharmaceutical composition comprising the PPPT compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the PPPT compound to be administered alone, it is preferable to present it as a pharmaceutical formulation (e.g., composition, preparation, medicament) comprising at least one PPPT compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one PPPT compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the PPPT compounds, and compositions comprising the PPPT compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular PPPT compound, the route of administration, the time of administration, the rate of excretion of the PPPT compound, the duration of the treatment, other drugs, compounds, and/or materials used in combination, the severity of the disorder, and the species, sex, age, weight, condition, general health, and prior medical history of the patient. The amount of PPPT compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the PPPT compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

Analytical Method 1:

The system consisted of a Hewlett Packard HP1100 LC system and a Higgins Clipeus 5 µm C18 100×3.0 mm column maintained at 40° C. Detection was achieved using a Waters Quattro Micro triple quadrupole mass spectrometer (electrospray, positive ion and negative ion), a DAD UV detector and a Sedex ELS 85 evaporative light scattering detector. Mobile Phase A: 0.1% aqueous formic acid. Mobile Phase B: 0.1% formic acid in MeOH. Flow rate 1 mL/min: Gradient: 0-1 min 15% B; 1-13 min 15-95% B; 13-20 min 95% B; 20-22 min 95-15% B; 22-25 min 15% B.

Analytical Method 2:

The system consisted of a Waters Acquity HPLC system and an Acquity BEH C18 1.7 μm 100×2.1 mm column, maintained at 40° C. Detection was achieved using a Waters Micromass ZQ2000 quadrupole mass spectrometer (electrospray, positive ion and negative ion), a PDA UV detector. Mobile Phase A: 0.1% aqueous formic acid, Mobile Phase B: 0.1% formic acid in MeCN. Flow rate 0.4 mL/min: Gradient: 0-0.4 min 5% B; 0.4-6.0 min 5-95% B; 6-6.8 min 95% B; 6.8-7.0 min 95-5% B; 7-8 min 5% B.

Analytical Method 3:

The system consisted of a Waters Acquity HPLC system and a Higgins Clipeus 5 μm C18 100×3.0 mm column, maintained at 40° C. Detection was achieved using a Waters Micromass ZQ2000 quadrupole mass spectrometer (electrospray, positive ion and negative ion), a PDA UV detector. Mobile Phase A: 0.1% aqueous formic acid, Mobile Phase B: 0.1% formic acid in MeOH. Flow rate 1 mL/min: Gradient: 0-1 min 15% B; 1-13 min 15-95% B; 13-20 min 95% B; 20-22 min 95-15% B; 22-25 min 15% B.

Analytical Method 4:

The system consisted of a Hewlett Packard 1050 LC system and a Luna 3 μm C18(2) 30×4.6 mm column. Detection was achieved using a Finnigan AQA single quadrupole mass spectrometer (electrospray, positive ion), a UV diode array detector and a Sedex ELS 65 evaporative light scattering detector. Mobile Phase A: 0.1% aqueous formic acid, Mobile Phase B: 0.1% formic acid in MeOH. Flow rate 2 mL/min: Gradient: 0-0.5 min 5% B; 0.5-4.5 min 5-95% B; 4.5-5 min 95% B; 5.5-6.0 min 95-5% B.

NMR Analysis

Proton NMR spectra were obtained using a Varian Unity Inova 400 spectrometer operating at 400 MHz.

Abbreviations

Bn=Benzyl.

DAST=Diethylaminosulphur trifluoride.

DCM=Dichloromethane.

DIPEA=Diisopropylethylamine.

DME=1,2-Dimethoxyethane.

DMF=Dimethylformamide.

HATU=(O-(7-azabenzotriazol-1-yl)-N,N,N',N'-tetramethyluroniumhexafluoro-phosphate).

HCl=Hydrochloric acid.

IMS=Industrial methylated spirit.

Pearlman's catalyst=Palladium hydroxide on carbon.

R.T.=Retention time.

SM=Starting material.

TFA=Trifluoroacetic acid.

THF=Tetrahydrofuran.

s=singlet.

d=doublet.

t=triplet.

m=multiplet.

q=quartet.

Compounds were named using Autonom.

Compounds containing chiral centres were prepared as racemic mixtures, unless stated otherwise.

Synthesis 1

(4-Hydroxy-4-phenyl-piperidin-1-yl)-[5-(1H-pyrazol-4-yl)-thiophen-3-yl]-methanone (AA-01)

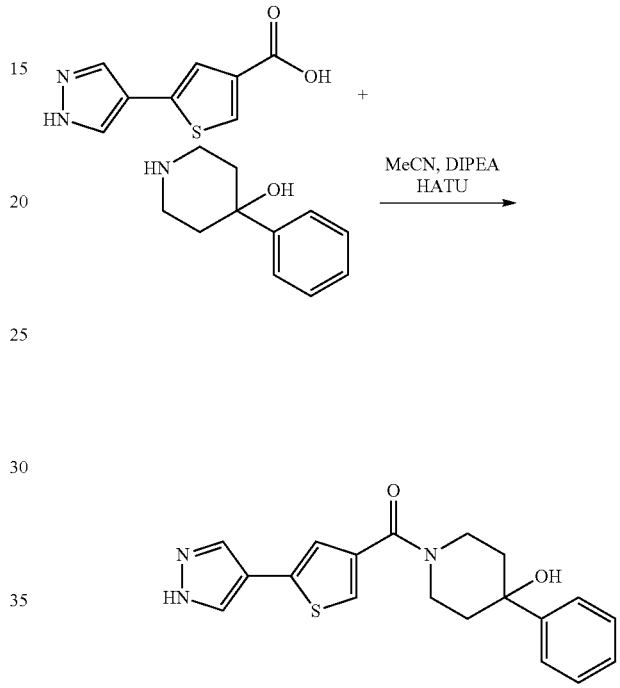

5-(1H-Pyrazol-4-yl)-thiophene-3-carboxylic acid (0.04 g, 0.2 mmol) and 4-phenyl-piperidin-4-ol (0.041 g, 0.23 mmol) were dissolved in acetonitrile (3 mL). HATU (0.24 mmol) and diisopropylethylamine (0.077 mL, 0.45 mmol) were added and the reaction mixture was stirred. After 1 hour the solvent was evaporated under vacuum and the residue stirred with aqueous sodium hydroxide (1 N, 3 mL) for 0.5 hours. The mixture was diluted with ethyl acetate and washed with brine, dried over magnesium sulphate, filtered and the solvent evaporated under vacuum. The residue was purified by flash chromatography on silica eluting with ethyl acetate. The fractions containing the desired product were concentrated under vacuum to give the title compound (0.041 g) as a white solid.

LCMS m/z 354.2 [M+H]$^+$ R.T.=8.94 min (Analytical Method 1). $^1$H NMR (400 MHz, d6-DMSO): δ 13.0 (s, 1H), 8.2 (s, 1H), 7.8 (s, 1H), 7.6 (s, 1H), 7.5 (d, 2H), 7.3 (m, 3H), 7.2 (t, 1H), 5.2 (s, 1H), 4.4-3.2 (m broad, 4H), 1.8-2.0 (m broad, 2H), 1.5-1.8 (m broad 2H).

The following compounds were prepared using methods analogous to those used to prepare (4-hydroxy-4-phenyl-piperidin-1-yl)-[5-(1H-pyrazol-4-yl)-thiophen-3-yl]-methanone. In some cases the product was purified by preparative HPLC on a C18 cartridge, eluting with 40%-70% methanol/water with 0.1% formic acid; the fractions containing the desired product were concentrated under vacuum and further lyophilised from methanol and water to give the title compound.

| Cmpd. No. | Structure | Analytical Method | R.T. (min) | MS [m/z] [M + H]+ |
|---|---|---|---|---|
| AA-02 | 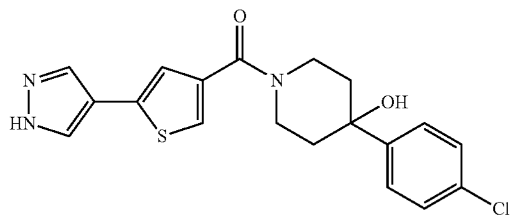 [SMILES: O=C(c1csc(-c2cn[nH]c2)c1)N1CCC(O)(c2ccc(Cl)cc2)CC1] | 1 | 10.03 | 388.04 |
| AA-03 | 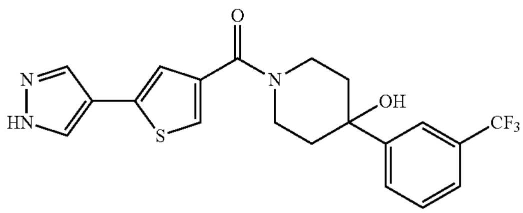 [SMILES: O=C(c1csc(-c2cn[nH]c2)c1)N1CCC(O)(c2cccc(C(F)(F)F)c2)CC1] | 1 | 10.27 | 422.05 |
| AA-04 | 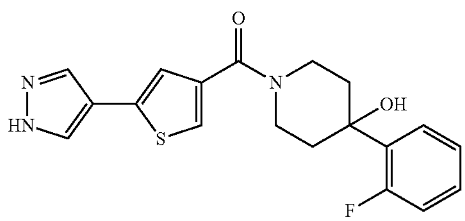 [SMILES: O=C(c1csc(-c2cn[nH]c2)c1)N1CCC(O)(c2ccccc2F)CC1] | 2 | 3.47 | 372.1 |
| AA-05 | 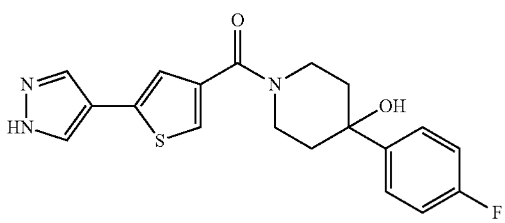 [SMILES: O=C(c1csc(-c2cn[nH]c2)c1)N1CCC(O)(c2ccc(F)cc2)CC1] | 1 | 9.14 | 372.1 |
| AA-06 | 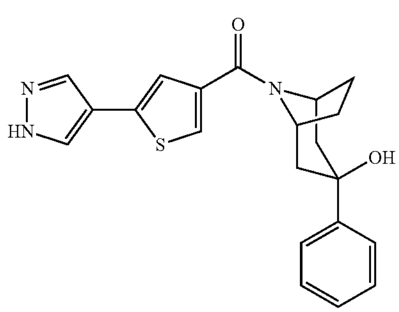 [SMILES: O=C(c1csc(-c2cn[nH]c2)c1)N1C2CCC1CC(O)(c1ccccc1)C2] | 2 | 3.50 | 380.20 |
| AA-07 | 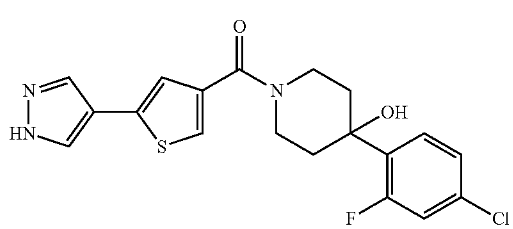 | 2 | 3.93 | 406.01 |

-continued

| Cmpd. No. | Structure | Analytical Method | R.T. (min) | MS [m/z] [M + H]⁺ |
|---|---|---|---|---|
| AA-08 | 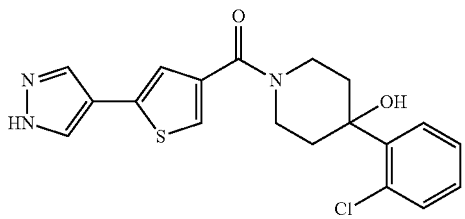 | 2 | 3.68 | 388.04 |
| AA-09 | 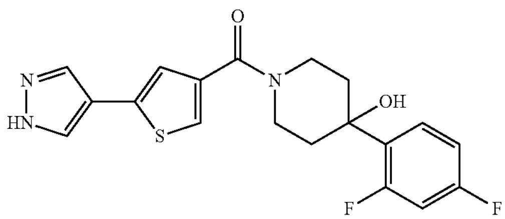 | 2 | 3.62 | 390.07 |
| AA-10 | 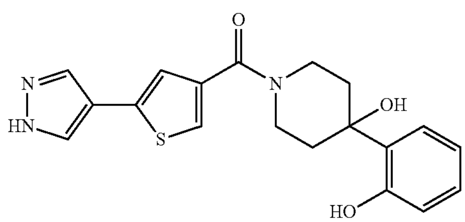 [SMILES: O=C(c1csc(-c2cn[nH]c2)c1)N1CCC(O)(c2ccccc2O)CC1] | 2 | 3.30 | 370.0 |
| AA-11 | 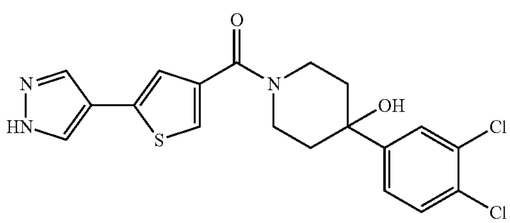 [SMILES: O=C(c1csc(-c2cn[nH]c2)c1)N1CCC(O)(c2ccc(Cl)c(Cl)c2)CC1] | 2 | 4.15 | 422.0 |
| AA-12 | 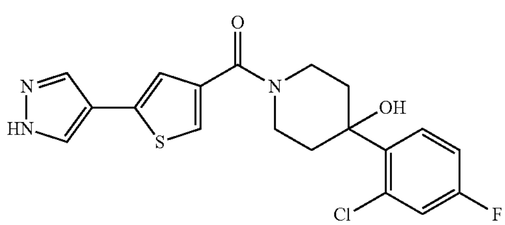 [SMILES: O=C(c1csc(-c2cn[nH]c2)c1)N1CCC(O)(c2ccc(F)cc2Cl)CC1] | 2 | 3.82 | 406.0 |
| AA-13 | 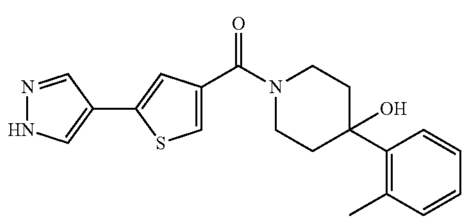 [SMILES: Cc1ccccc1C1(O)CCN(C(=O)c2csc(-c3cn[nH]c3)c2)CC1] | 2 | 3.69 | 368.11 |
| AA-14 | 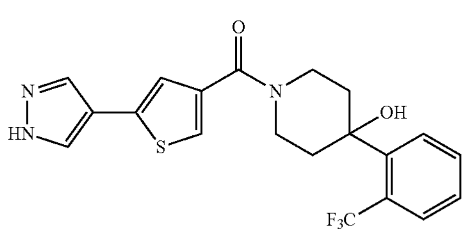 [SMILES: O=C(c1csc(-c2cn[nH]c2)c1)N1CCC(O)(c2ccccc2C(F)(F)F)CC1] | 2 | 3.89 | 422.1 |

-continued

| Cmpd. No. | Structure | Analytical Method | R.T. (min) | MS [m/z] [M + H]+ |
|---|---|---|---|---|
| AA-15 | 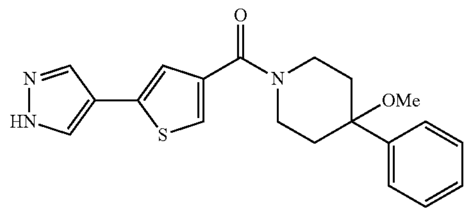 [SMILES: COC1(c2ccccc2)CCN(C(=O)c2csc(-c3cn[nH]c3)c2)CC1] | 1 | 10.62 | 368.1 |
| AA-16 | 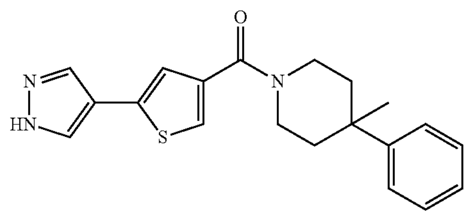 [SMILES: CC1(c2ccccc2)CCN(C(=O)c2csc(-c3cn[nH]c3)c2)CC1] | 2 | 4.42 | 352.1 |
| AA-17 | 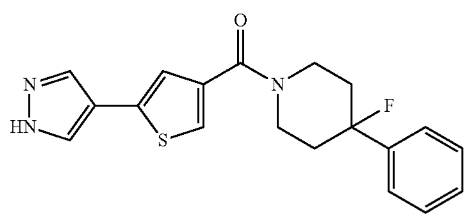 [SMILES: O=C(c1csc(-c2cn[nH]c2)c1)N1CCC(F)(c2ccccc2)CC1] | 3 | 10.66 | 356.1 |
| AA-18 | 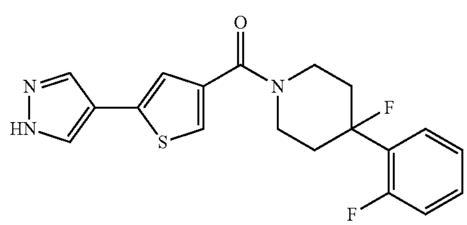 | 2 | 4.28 | 374.1 |
| AA-19 | 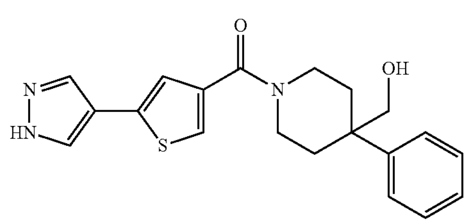 [SMILES: O=C(c1csc(-c2cn[nH]c2)c1)N1CCC(CO)(c2ccccc2)CC1] | 2 | 9.17 | 368.1 |
| AA-20 | 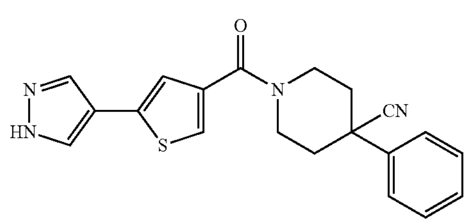 [SMILES: N#CC1(c2ccccc2)CCN(C(=O)c2csc(-c3cn[nH]c3)c2)CC1] | 3 | 9.59 | 363.1 |
| BB-01 | 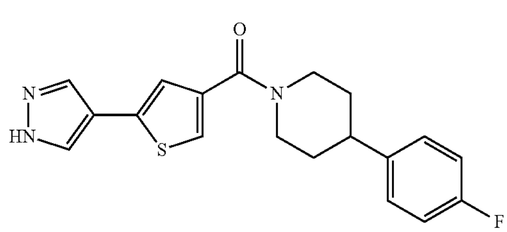 [SMILES: O=C(c1csc(-c2cn[nH]c2)c1)N1CCC(c2ccc(F)cc2)CC1] | 3 | 10.62 | 356.1 |

-continued

| Cmpd. No. | Structure | Analytical Method | R.T. (min) | MS [m/z] [M + H]+ |
|---|---|---|---|---|
| BB-02 | 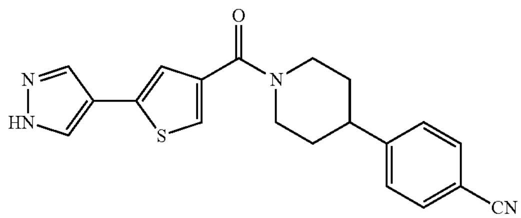 [SMILES: N#Cc1ccc(C2CCN(C(=O)c3csc(-c4cn[nH]c4)c3)CC2)cc1] | 3 | 9.37 | 363.1 |
| BB-03 | 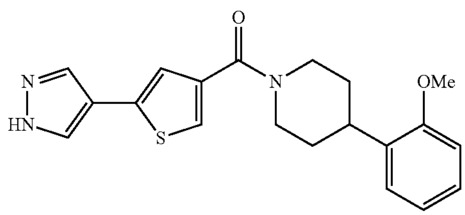 [SMILES: COc1ccccc1C1CCN(C(=O)c2csc(-c3cn[nH]c3)c2)CC1] | 1 | 10.96 | 368.4 |
| BB-04 | 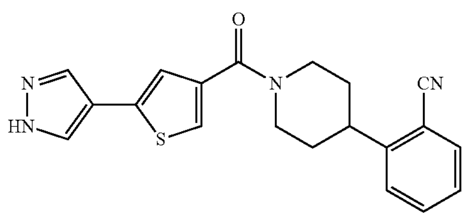 [SMILES: N#Cc1ccccc1C1CCN(C(=O)c2csc(-c3cn[nH]c3)c2)CC1] | 2 | 3.94 | 363.11 |
| BB-05 | 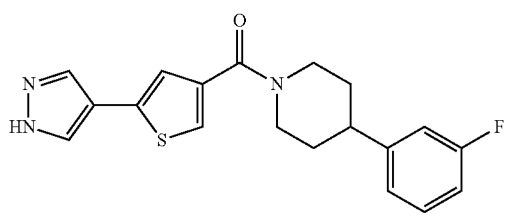 [SMILES: O=C(c1csc(-c2cn[nH]c2)c1)N1CCC(c2cccc(F)c2)CC1] | 1 | 10.75 | 356.25 |
| BB-06 | 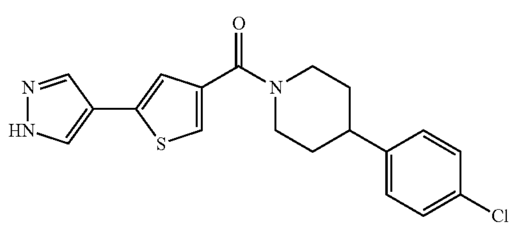 [SMILES: O=C(c1csc(-c2cn[nH]c2)c1)N1CCC(c2ccc(Cl)cc2)CC1] | 2 | 4.63 | 372.17 |
| BB-07 | 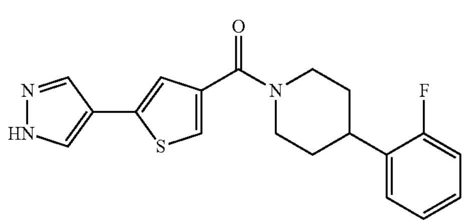 | 2 | 4.32 | 356.15 |

-continued

| Cmpd. No. | Structure | Analytical Method | R.T. (min) | MS [m/z] [M + H]+ |
|---|---|---|---|---|
| BB-08 | 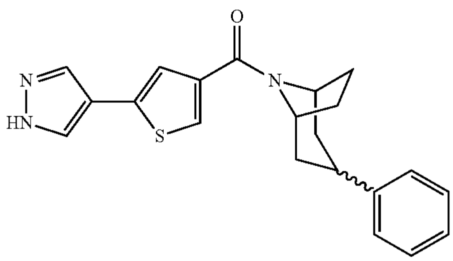 [SMILES: O=C(c1csc(-c2cn[nH]c2)c1)N1C2CCC1CC(c1ccccc1)C2] | 2 | 4.38 & 4.41 | 364.12 |
| BB-09 | 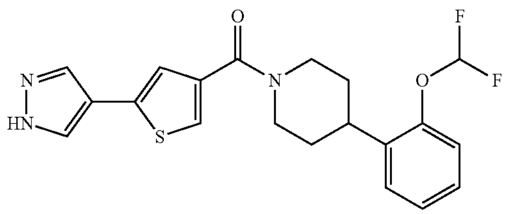 [SMILES: O=C(c1csc(-c2cn[nH]c2)c1)N1CCC(c2ccccc2OC(F)F)CC1] | 2 | 4.36 | 404.8 |
| BB-10 | 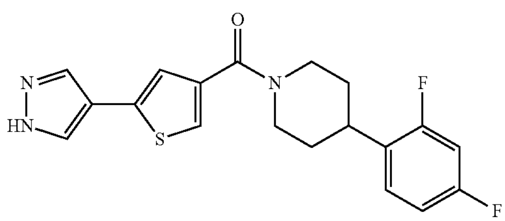 [SMILES: O=C(c1csc(-c2cn[nH]c2)c1)N1CCC(c2ccc(F)cc2F)CC1] | 2 | 4.42 | 374.1 |
| BB-11 | 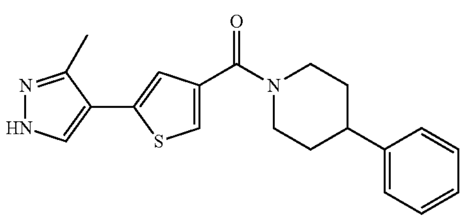 [SMILES: Cc1n[nH]cc1-c1cc(C(=O)N2CCC(c3ccccc3)CC2)cs1] | 1 | 11.09 | 352.2 |
| AA-22 | 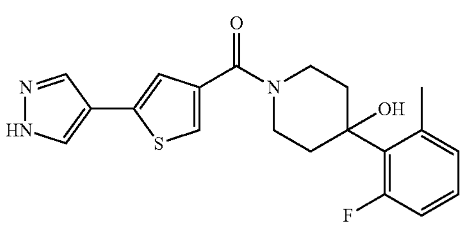 [SMILES: Cc1cccc(F)c1C1(O)CCN(C(=O)c2csc(-c3cn[nH]c3)c2)CC1] | 2 | 3.80 | 386.1 |
| AA-23 | 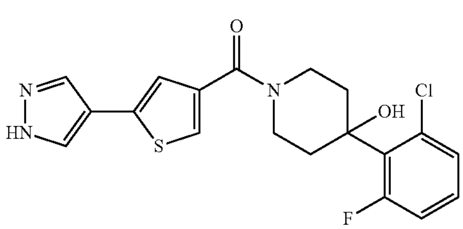 [SMILES: O=C(c1csc(-c2cn[nH]c2)c1)N1CCC(O)(c2c(F)cccc2Cl)CC1] | 2 | 3.69 | 406.0 |

-continued

| Cmpd. No. | Structure | Analytical Method | R.T. (min) | MS [m/z] [M + H]+ |
|---|---|---|---|---|
| AA-26 | 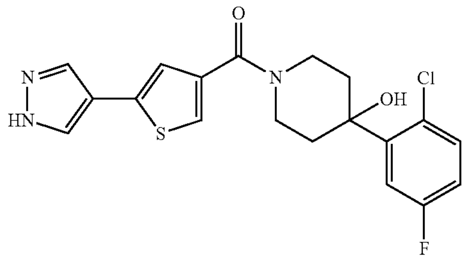 [SMILES: O=C(c1csc(-c2cn[nH]c2)c1)N1CCC(O)(c2cc(F)ccc2Cl)CC1] | 2 | 3.81 | 406.0 |
| AA-37 | 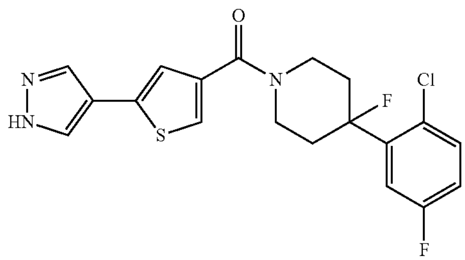 [SMILES: O=C(c1csc(-c2cn[nH]c2)c1)N1CCC(F)(c2cc(F)ccc2Cl)CC1] | 2 | 4.58 | 407.9 |
| AA-40 | 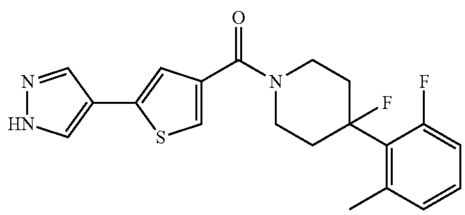 [SMILES: Cc1cccc(F)c1C1(F)CCN(C(=O)c2csc(-c3cn[nH]c3)c2)CC1] | 2 | 4.60 | 388.0 |
| AA-36 | 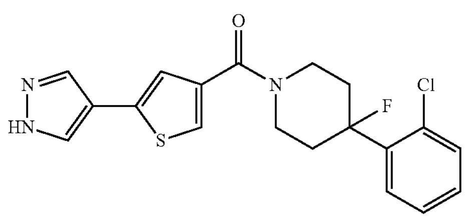 [SMILES: O=C(c1csc(-c2cn[nH]c2)c1)N1CCC(F)(c2ccccc2Cl)CC1] | 2 | 4.45 | 390.0 |
| AA-38 | 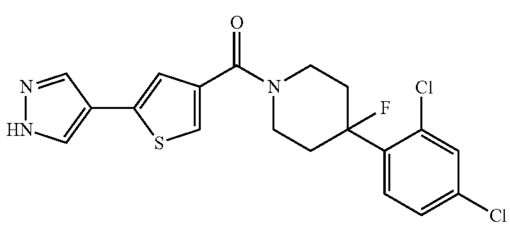 [SMILES: O=C(c1csc(-c2cn[nH]c2)c1)N1CCC(F)(c2ccc(Cl)cc2Cl)CC1] | 2 | 4.98 | 423.9 |
| AA-35 | 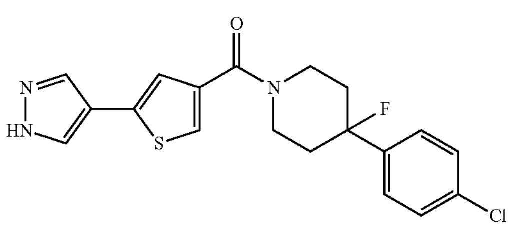 [SMILES: O=C(c1csc(-c2cn[nH]c2)c1)N1CCC(F)(c2ccc(Cl)cc2)CC1] | 2 | 4.63 | 390.0 |

| Cmpd. No. | Structure | Analytical Method | R.T. (min) | MS [m/z] [M + H]+ |
|---|---|---|---|---|
| AA-31 | 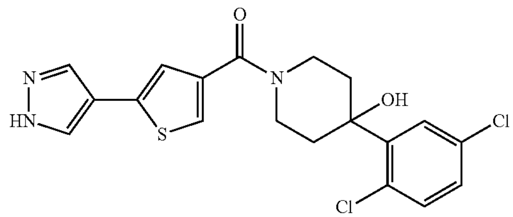 [SMILES: O=C(c1csc(-c2cn[nH]c2)c1)N1CCC(O)(c2cc(Cl)ccc2Cl)CC1] | 2 | 4.08 | 421.9 |
| AA-28 | 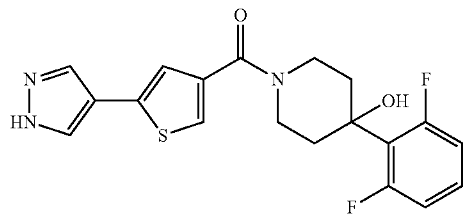 | 2 | 3.46 | 390.0 |
| AA-27 | 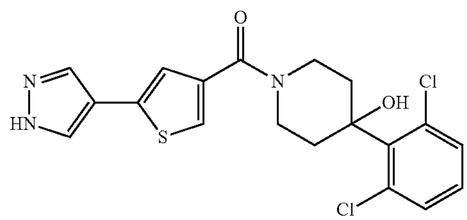 [SMILES: O=C(c1csc(-c2cn[nH]c2)c1)N1CCC(O)(c2c(Cl)cccc2Cl)CC1] | 2 | 3.88 | 421.9 |
| AA-24 | 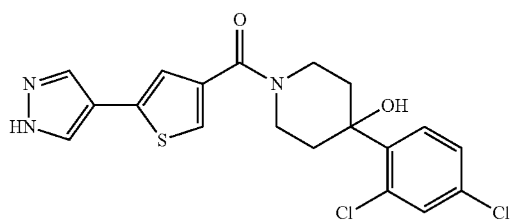 [SMILES: O=C(c1csc(-c2cn[nH]c2)c1)N1CCC(O)(c2ccc(Cl)cc2Cl)CC1] | 2 | 4.10 | 421.9 |
| AA-21 | 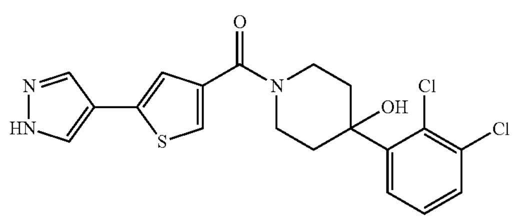 [SMILES: O=C(c1csc(-c2cn[nH]c2)c1)N1CCC(O)(c2cccc(Cl)c2Cl)CC1] | 2 | 3.96 | 421.9 |
| AA-29 | 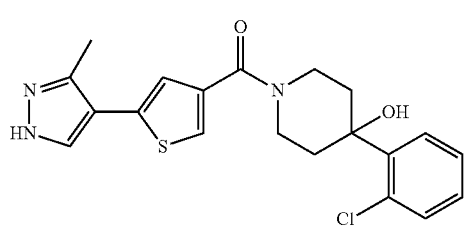 [SMILES: Cc1n[nH]cc1-c1cc(C(=O)N2CCC(O)(c3ccccc3Cl)CC2)cs1] | 2 | 3.77 | 402.0 |
| BB-13 | 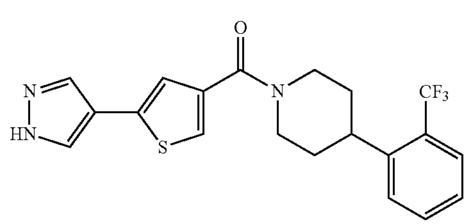 [SMILES: O=C(c1csc(-c2cn[nH]c2)c1)N1CCC(c2ccccc2C(F)(F)F)CC1] | 2 | 4.69 | 406.0 |

-continued

| Cmpd. No. | Structure | Analytical Method | R.T. (min) | MS [m/z] [M + H]⁺ |
|---|---|---|---|---|
| BB-12 | 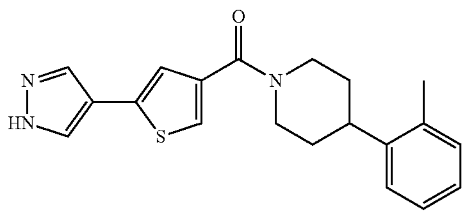 [SMILES: Cc1ccccc1C1CCN(C(=O)c2csc(-c3cn[nH]c3)c2)CC1] | 2 | 4.45 | 352.1 |
| BB-15 | 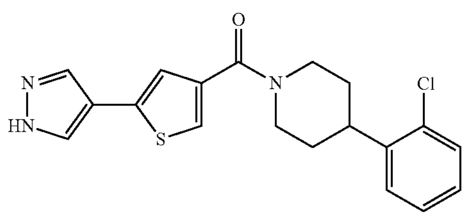 | 2 | 4.62 | 372.0 |
| BB-14 | 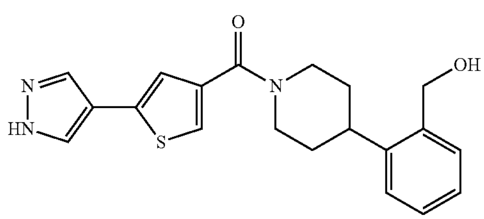 [SMILES: O=C(c1csc(-c2cn[nH]c2)c1)N1CCC(c2ccccc2CO)CC1] | 2 | 3.38 | 368.1 |
| AA-34 | 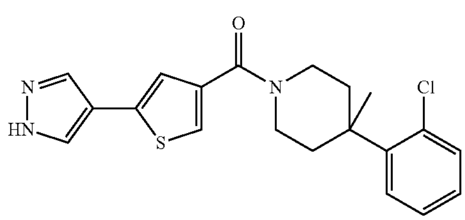 [SMILES: CC1(c2ccccc2Cl)CCN(C(=O)c2csc(-c3cn[nH]c3)c2)CC1] | 2 | 4.73 | 386.0 |
| AA-33 | 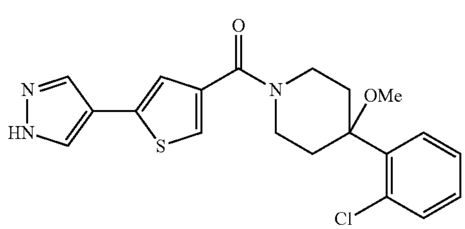 [SMILES: COC1(c2ccccc2Cl)CCN(C(=O)c2csc(-c3cn[nH]c3)c2)CC1] | 2 | 4.36 | 401.9 |
| AA-41 | 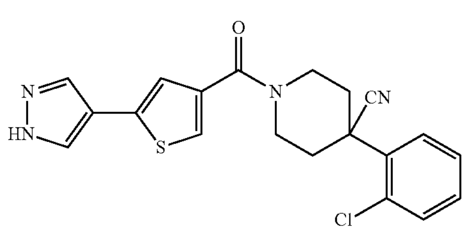 [SMILES: N#CC1(c2ccccc2Cl)CCN(C(=O)c2csc(-c3cn[nH]c3)c2)CC1] | 2 | 4.10 | 396.9 |

| Cmpd. No. | Structure | Analytical Method | R.T. (min) | MS [m/z] [M + H]+ |
|---|---|---|---|---|
| AA-25 | 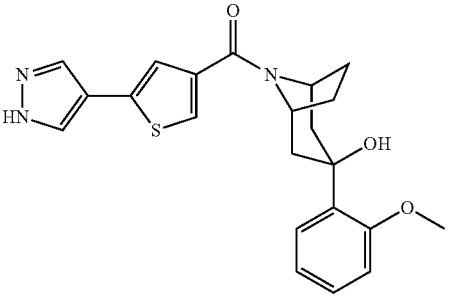 [SMILES: COc1ccccc1C1(O)CC2CCC(C1)N2C(=O)c1csc(-c2cn[nH]c2)c1] | 2 | 3.54 | 410.1 |
| AA-30 | 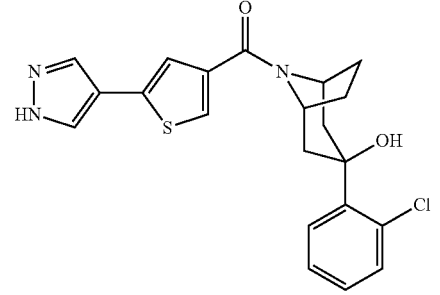 [SMILES: O=C(c1csc(-c2cn[nH]c2)c1)N1C2CCC1CC(O)(c1ccccc1Cl)C2] | 2 | 3.65 | 414.0 |
| AA-32 | 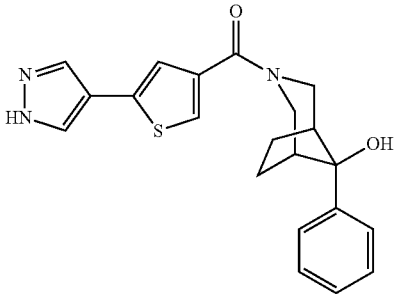 [SMILES: O=C(c1csc(-c2cn[nH]c2)c1)N1CC2CCC(C1)C2(O)c1ccccc1] | 2 | 3.67 | 380.1 |

Additional $^1$H NMR data for several of the above compounds is given below:

| Cmpd. No. | $^1$H NMR (400 MHz, d6-DMSO) δ: |
|---|---|
| AA-04 | 13.1 (s, 1H), 8.1 (s broad, 1H), 7.8 (m broad, 1H), 7.7 (t, 1H), 7.55 (s, 1H), 7.3 (m, 2H), 7.2 (t, 1H), 7.1 (m, 1H), 5.4 (s, 1H), 4.4-3.8 (m, 2H), 3.7-3.1 (m broad, 2H), 2.2-2.0 (m, broad, 2H), 1.8-1.6 (m broad, 2H). |
| AA-06 | 13.1 (s, 1H), 8.15 (s broad, 1H), 7.9 (s broad, 1H), 7.7 (s, 1H), 7.4 (m, 3H), 7.3 (t, 2H), 7.2 (t, 1H), 5.1 (s, 1H), 4.6-4.4 (m broad, 2H), 2.4-1.8 (m broad, 8H). |
| AA-07 | 13.1 (s, 1H), 8.1 (s broad, 1H), 7.8 (s broad, 1H), 7.7 (t, 1H), 7.6 (s, 1H), 7.2-7.4 (m, 3H), 5.5 (s broad, 1H), 4.4-3.1 (m broad, 4H), 2.2-2.0 (m, 2H) 1.7-1.5 (m broad, 2H). |
| AA-08 | 13.1 (s, 1H), 8.1 (s, 1H), 7.8 (m, 2H), 7.6 (s, 1H), 7.4 (m, 2H), 7.3 (m, 2H), 5.4 (s, 1H), 4.4 (m, 2H), 3.9-3.1 (m broad, 4H), 1.8-1.6 (m broad, 2H). |
| AA-14 | 13.1 (s, 1H), 8.1 (s, 1H), 7.8 (m, 3H), 7.6 (m, 2H), 7.5 (t, 1H), 7.2 (s, 1H), 5.25 (s, 1H), 4.4-3.1 (m broad, 4H), 2.2-1.7 (m broad, 4H). |
| AA-16 | 13.1 (s, 1H), 8.1 (s, 1H), 7.8 (s, 1H), 7.5 (s, 1H), 7.4 (m, 2H), 7.3 (t, 2H), 7.25 (s, 1H), 7.2 (t, 1H), 3.7-3.4 (m broad, 4H), 2.1 (m broad, 2H), 1.7 (m broad, 2H), 1.1 (s, 3H). |
| BB-04 | 13.1 (s, 1H), 8.1 (s broad, 1H), 7.8 (m broad, 2H), 7.7 (t, 1H), 7.6 (m, 2H), 7.4 (t, 1H), 7.3 (s, 1H), 4.6-4.1 (m broad, 2H), 3.4-2.8 (m broad, 3H), 1.9-1.6 (m broad, 4H). |

The following piperidines used in the syntheses of analogues listed above were commercially available:

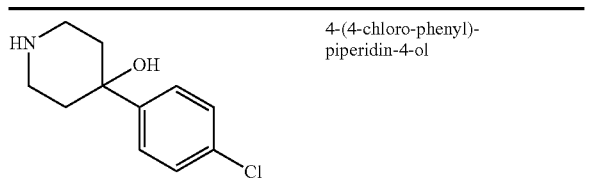 4-(4-chloro-phenyl)-piperidin-4-ol

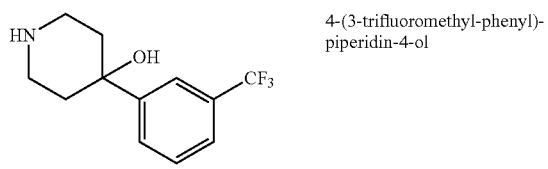 4-(3-trifluoromethyl-phenyl)-piperidin-4-ol

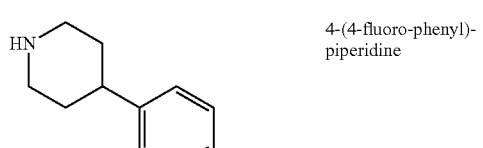 4-(4-fluoro-phenyl)-piperidine

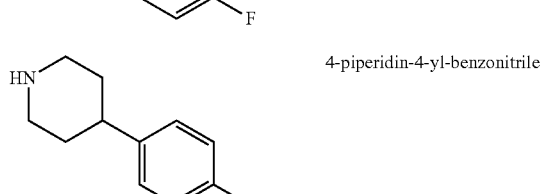 4-piperidin-4-yl-benzonitrile

 4-(2-methoxy-phenyl)-piperidine

 4-(3-fluoro-phenyl)-piperidine

 4-(2-fluoro-phenyl)-piperidine

 4-(2-trifluoromethyl-phenyl)-piperidin-4-ol

 4-phenyl-piperidine-4-carbonitrile

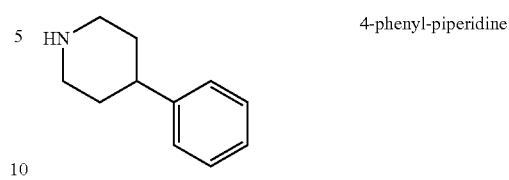 4-phenyl-piperidine

Other piperidines were prepared using the methods described below.

Synthesis 2

4-(2,4-Difluoro-phenyl)-4-hydroxy-piperidine-1-carboxylic acid tert-butyl ester

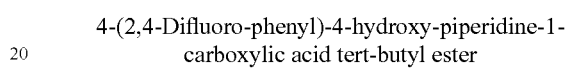

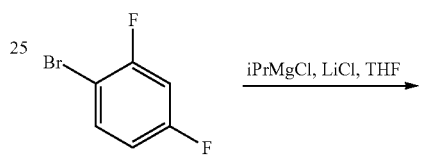

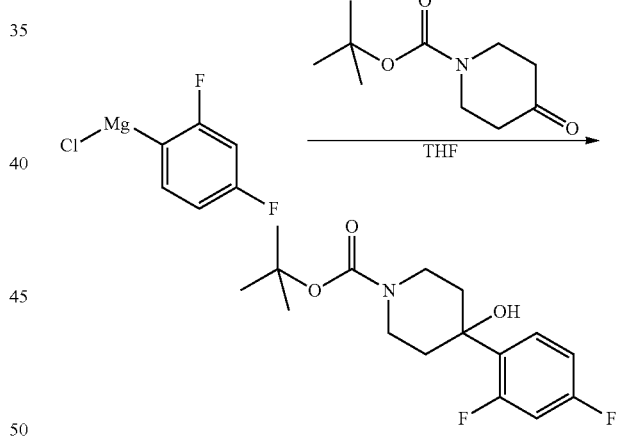

1-Bromo-2,4-difluoro-benzene (0.67 g, 3.5 mmol) was dissolved in THF (5 mL) and cooled to 0° C. Isopropylmagnesium chloride lithium chloride complex in THF (1.3 M, 2.5 mL, 3.2 mmol) was added. The mixture was stirred for 0.5 hours then added dropwise to a solution of 4-oxo-piperidine-1-carboxylic acid tert-butyl ester (0.5 g, 2.5 mmol) in THF (10 mL) that had been cooled to −78° C. The mixture was allowed to warm to room temperature then cooled to −78° C. and a solution of saturated aqueous ammonium chloride was added and the mixture extracted into ethyl acetate, dried over magnesium sulphate, filtered and the solvent removed by evaporation under vacuum. The residue was purified by flash chromatography on silica eluting with 0-50% ethyl acetate/hexane. The fractions containing the desired product were concentrated under vacuum to give the title compound (0.7 g)

as a clear, colourless oil. LCMS m/z 314.3 [M+H]+. R.T.=4.65 min (Analytical Method 4).

Synthesis 3

4-(2,4-Difluoro-phenyl)-piperidin-4-ol

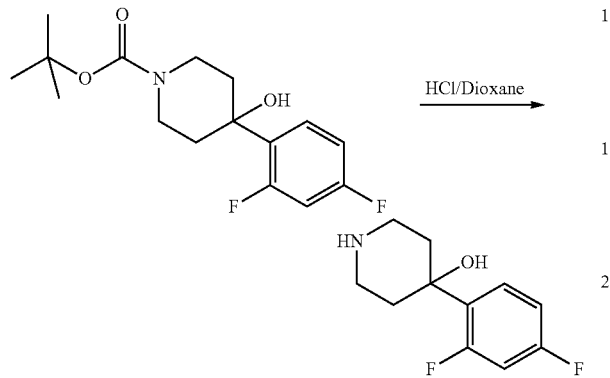

4-(2,4-Difluoro-phenyl)-4-hydroxy-piperidine-1-carboxylic acid tert-butyl ester (0.2 g) was dissolved in a solution of hydrogen chloride in dioxane (4 N, 1 mL). The mixture was stirred for 1 hour and the solvent removed by evaporation under vacuum. The solid was triturated from ether to afford the title compound as a pale yellow solid (0.08 g). LCMS m/z 214.25 [M+H]+. R.T.=1.06 min (Analytical Method 4).

The following substituted piperidines were made by methods analogous to those used to prepare 4-(2,4-difluoro-phenyl)-piperidin-4-ol from 4-oxo-piperidine-1-carboxylic acid tert-butyl ester:

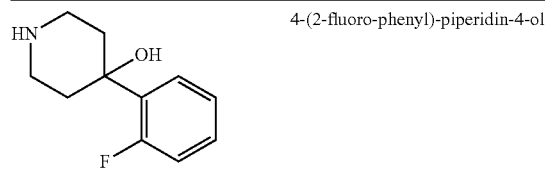

4-(2-fluoro-phenyl)-piperidin-4-ol

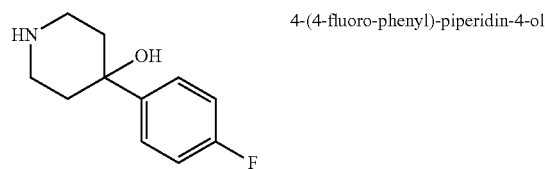

4-(4-fluoro-phenyl)-piperidin-4-ol

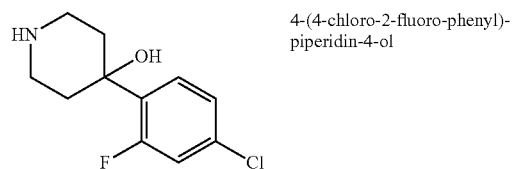

4-(4-chloro-2-fluoro-phenyl)-piperidin-4-ol

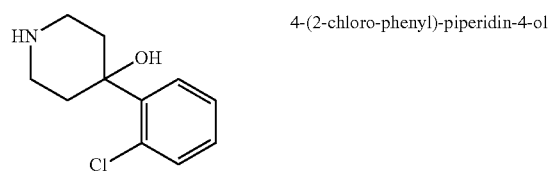

4-(2-chloro-phenyl)-piperidin-4-ol

-continued

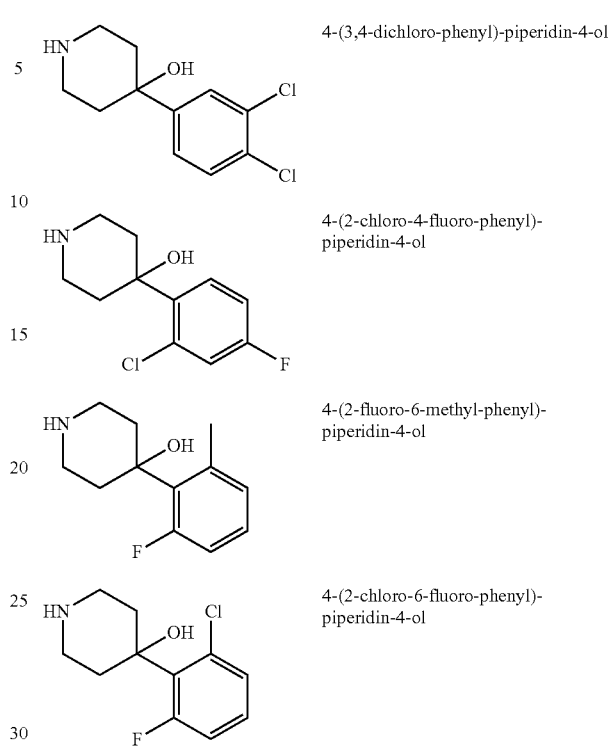

4-(3,4-dichloro-phenyl)-piperidin-4-ol 4-(2-chloro-4-fluoro-phenyl)-piperidin-4-ol 4-(2-fluoro-6-methyl-phenyl)-piperidin-4-ol 4-(2-chloro-6-fluoro-phenyl)-piperidin-4-ol 4-(2-chloro-5-fluoro-phenyl)-piperidin-4-ol

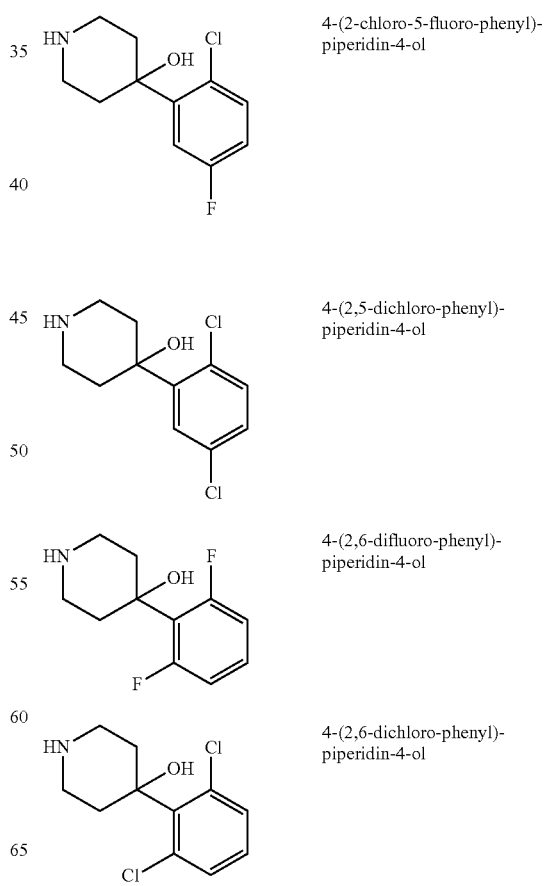

4-(2,5-dichloro-phenyl)-piperidin-4-ol 4-(2,6-difluoro-phenyl)-piperidin-4-ol 4-(2,6-dichloro-phenyl)-piperidin-4-ol

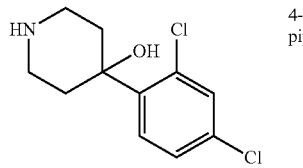

4-(2,4-dichloro-phenyl)-piperidin-4-ol

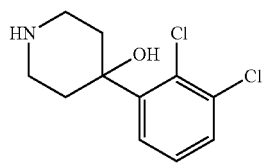

4-(2,3-dichloro-phenyl)-piperidin-4-ol

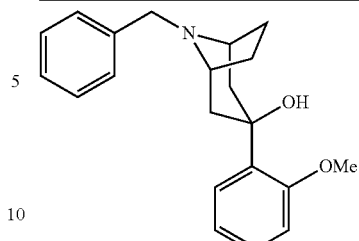

8-benzyl-3-(2-methoxy-phenyl)-8-aza-bicyclo[3.2.1]octan-3-ol

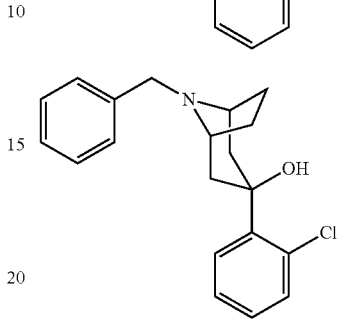

8-benzyl-3-(2-chloro-phenyl)-8-aza-bicyclo[3.2.1]octan-3-ol

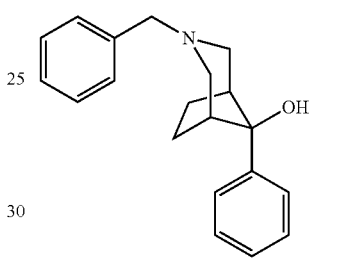

3-benzyl-8-phenyl-3-aza-bicyclo[3.2.1]octan-8-ol

Synthesis 4

8-Benzyl-3-phenyl-8-aza-bicyclo[3.2.1]octan-3-ol

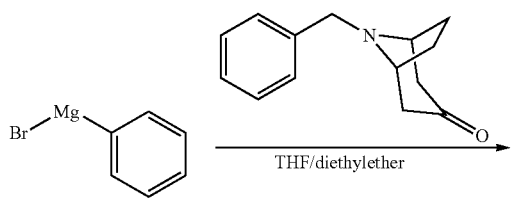

A solution of phenylmagnesium bromide in ether (3 M, 2.3 mL) was added dropwise to a solution of 8-benzyl-8-aza-bicyclo[3.2.1]octan-3-one (1.0 g, 4.6 mmol) in THF (20 mL) that had been cooled to 0° C. The mixture was stirred for 3 hours and a solution of saturated aqueous ammonium chloride was added and the products extracted into diethyl ether, dried over sodium sulphate, filtered and the solvent removed by evaporation under vacuum. The residue was purified by flash chromatography on silica eluting with 10-30% ethyl acetate/hexane. The fractions containing the desired product were concentrated under vacuum to give the title compound (0.5 g) as an oil. LCMS m/z 294.4 [M+H]$^+$. R.T.=2.59 min (Analytical Method 4).

The following compounds were made by methods analogous to those used to prepare 8-benzyl-3-phenyl-8-aza-bicyclo[3.2.1]octan-3-ol:

Synthesis 5

3-Phenyl-8-aza-bicyclo[3.2.1]octan-3-ol

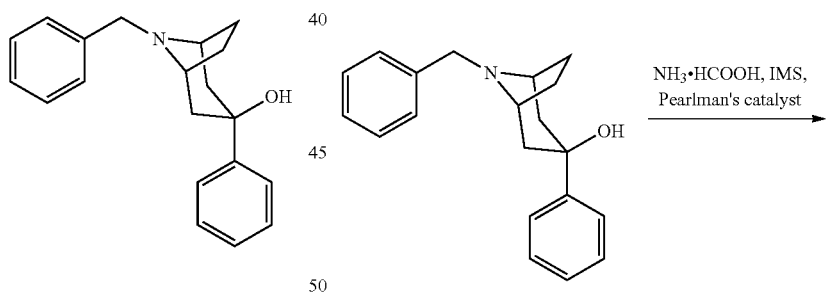

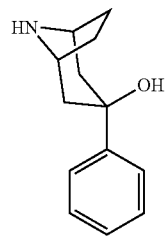

8-Benzyl-3-phenyl-8-aza-bicyclo[3.2.1]octan-3-ol (0.24 g, 0.84 mmol) was dissolved in IMS (4.5 mL) and water (0.5 mL). Ammonium formate (0.5 g) and Pearlman's catalyst (0.12 g) were added. The mixture was heated to reflux for 0.5 hour, filtered and the solution concentrated to give an oil which was purified by chromatography on an SCX cartridge eluting with ammonia (2 M) in methanol. The fractions containing the desired product were concentrated under vacuum to give the title compound (0.13 g) as an oil.

LCMS m/z 204.3 [M+H]⁺. R.T.=0.36 min (Analytical Method 4).

The following compounds were made by methods analogous to those used to prepare 3-phenyl-8-aza-bicyclo[3.2.1]octan-3-ol:

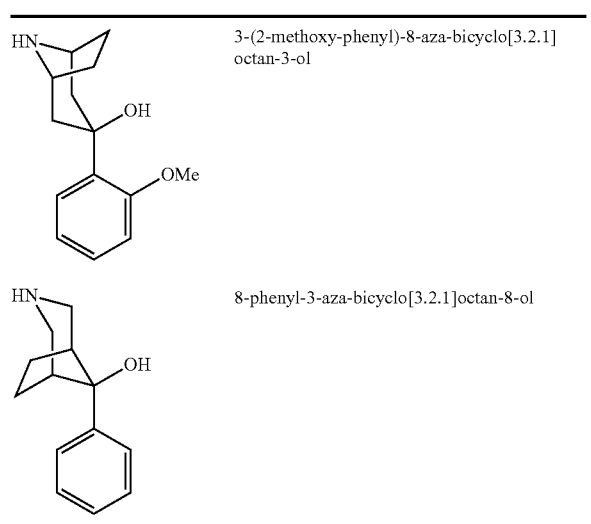

Synthesis 6

4-Methoxy-4-phenyl-piperidine-1-carboxylic acid tert-butyl ester

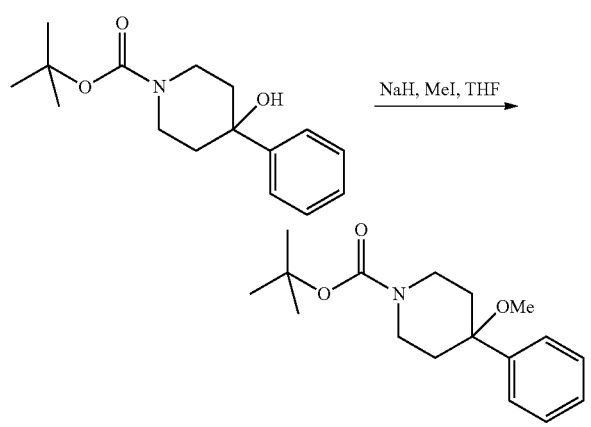

4-Hydroxy-4-phenyl-piperidine-1-carboxylic acid tert-butyl ester (0.5 g, 1.8 mmol) was dissolved in dry THF (15 mL) and sodium hydride (60% disp. in mineral oil; 0.076 g, 1.9 mmol) added and the mixture stirred for 1 hour. Methyl iodide (0.16 mL; 2.7 mmol) was then added and the mixture stirred overnight. Brine was added and the product extracted into ethyl acetate, dried over sodium sulphate, filtered and the solvent removed by evaporation. The residue was purified by flash chromatography on silica eluting with 0-10% ethyl acetate/hexane. The fractions containing the desired product were concentrated under vacuum to give the title compound as a clear colourless oil (0.35 g).

LCMS m/z 292.4 [WH]⁺. R.T.=4.86 min (Analytical Method 4).

Synthesis 7

4-Methoxy-4-phenyl-piperidine

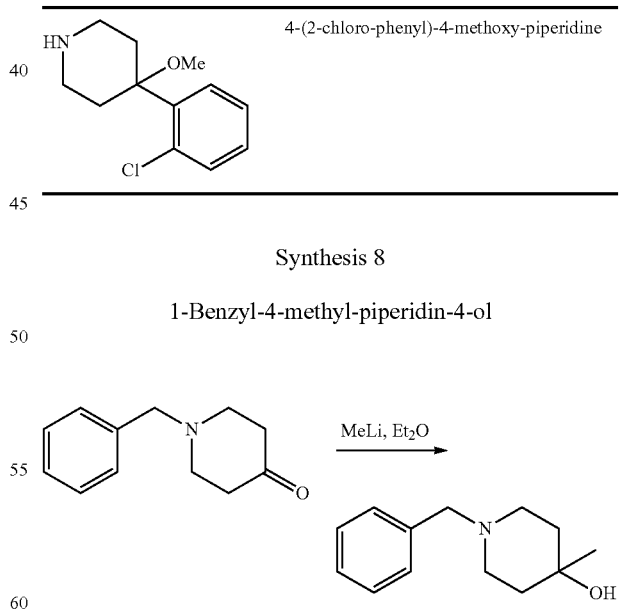

4-Methoxy-4-phenyl-piperidine-1-carboxylic acid tert-butyl ester (0.35 g) was dissolved in a solution of hydrogen chloride in dioxane (4 N, 3 mL). The mixture was stirred for 1 hour and the solvent removed by evaporation under vacuum. The solid was triturated from ether to afford the title compound as a white solid (0.25 g). LCMS m/z 192.2[M+H]⁺. R.T.=1.96 min (Analytical Method 4).

The following substituted piperidine was made by methods analogous to those used to prepare 4-methoxy-4-phenyl-piperidine:

Synthesis 8

1-Benzyl-4-methyl-piperidin-4-ol

1-Benzyl-4-piperidine (1.0 g, 5.2 mmol) was dissolved in dry diethyl ether (10 mL) and cooled to −78° C. Methyl lithium in diethyl ether (1.6 M; 4.6 mL, 7.4 mmol) was added and the mixture stirred for 1.5 hours. The mixture was diluted with water and the products extracted into diethyl ether, dried over magnesium sulphate, filtered and the solvent removed by evaporation under vacuum. The residue was purified by flash chromatography on silica eluting with 0-10% ethyl acetate/methanol. The fractions containing the desired product were concentrated under vacuum to give the title compound as a yellow oil (0.35 g). LCMS m/z 206.27[M+H]$^+$. R.T.=0.83 min (Analytical Method 4).

Synthesis 9

1-Benzyl-4-(4-bromo-phenyl)-4-methyl-piperidine

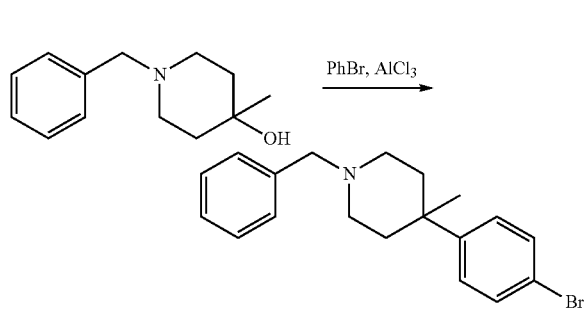

To a solution of 1-benzyl-4-methyl-piperidin-4-ol (0.4 g, 1.95 mmol) in bromobenzene (1.2 mL) was added aluminium trichloride (0.39 g, 2.9 mmol). The mixture was then heated to 100° C. for 14 hours and left standing at room temperature for 48 hours. Aqueous sodium hydroxide (1 N, 30 mL) was added and the products extracted into ethyl acetate, dried over magnesium sulphate, filtered and the solvent removed by evaporation under vacuum. The residue was purified by flash chromatography on silica eluting with 0-25% ethyl acetate/hexane. The fractions containing the desired product were concentrated under vacuum to give the title compound as a brown oil (0.5 g). LCMS m/z 344.5 [M+H]$^+$. R.T.=3.13 min (Analytical Method 4).

Synthesis 10

4-Methyl-4-phenyl-piperidine hydrochloride

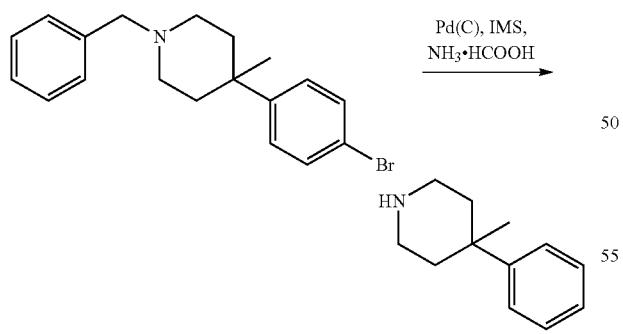

1-Benzyl-4-(4-bromo-phenyl)-4-methyl-piperidine (0.35 g, 1.0 mmol) was dissolved in IMS (20 mL) and palladium on carbon (10%; 0.15 g) in water (2 mL) was added under nitrogen. Ammonium formate (0.63 g, 10 mmol) was added and the mixture heated at reflux for 0.5 hour. The mixture was allowed to cool, filtered and the solvent removed by evaporation under vacuum. The residue was treated with a solution of hydrogen chloride in dioxane (4 M; 0.5 mL) followed by trituration from diethylether to give the title compound as a white solid (0.095 g). LCMS m/z 176.2 [M+H]$^+$. R.T.=2.21 min (Analytical Method 4).

Synthesis 11

1-Benzyl-4-phenyl-piperidin-4-ol

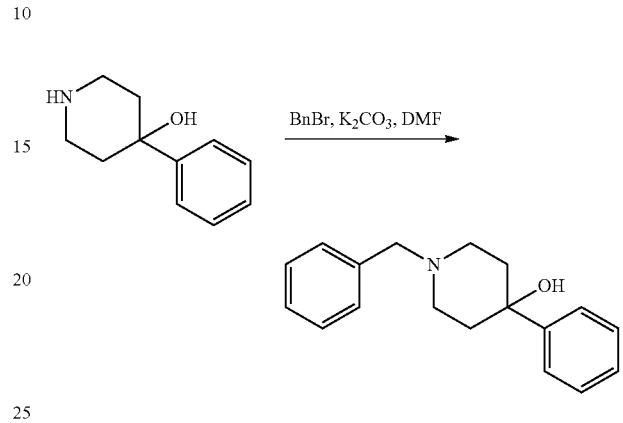

4-Hydroxy-4-phenylpiperidine (0.5 g, 2.8 mmol), benzylbromide (0.5 g, 3 mmol) and potassium carbonate (0.8 g, 6 mmol) were dissolved in DMF (5 mL) and stirred for 2 hours. The mixture was diluted with ethyl acetate and washed with a solution of saturated aqueous sodium carbonate solution then dried over magnesium sulphate, filtered and the solvent removed by evaporation under vacuum. The resulting solid was recrystallised from pentane to give the title compound as a white solid (0.47 g). LCMS m/z 268.3 [M+H]$^+$. R.T.=2.37 min (Analytical Method 4).

Synthesis 12

1-Benzyl-4-fluoro-4-phenyl-piperidine

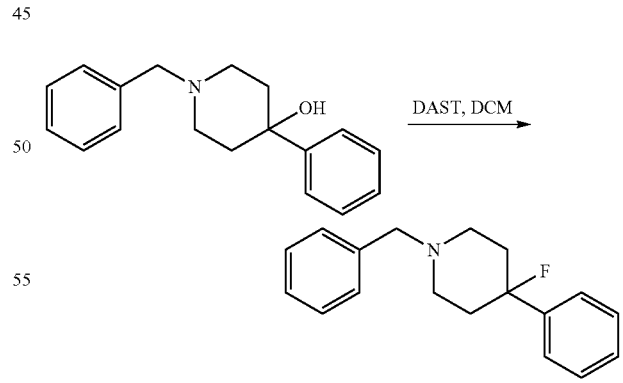

1-Benzyl-4-phenyl-piperidin-4-ol (0.45 g, 1.69 mmol) in DCM (20 mL) was cooled to −78° C. Diethylaminosulphur trifluoride (2 mmol) was added and the mixture stirred for 0.5 hour and allowed to warm to room temperature. The mixture was diluted with DCM and washed with water, dried over magnesium sulphate, filtered and the solvent removed by evaporation under vacuum. The oil was used without further purification. LCMS m/z 270.3 [M+H]⁺. R.T.=2.87 min (Analytical Method 4).

Synthesis 13

1-Benzyl-4-phenyl-piperidin-4-ol

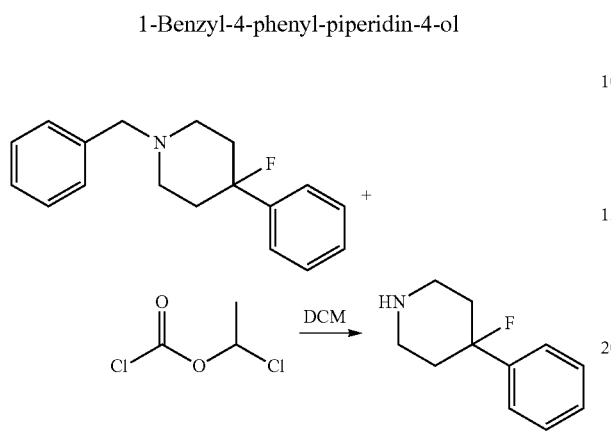

To 1-benzyl-4-fluoro-4-phenyl-piperidine (0.22 g) in dry DCM (5 mL) was added 1-chloroethylchloroformate (1 mmol). The mixture was stirred for 1 hour and then methanol (5 mL) was added and the mixture stirred overnight. The solvent was removed under vacuum, and the resulting solid triturated from diethyl ether to give the title compound as a white solid (0.12 g). LCMS m/z 180.1 [M+H]⁺. R.T.=2.27 min (Analytical Method 4).

Synthesis 14

4-Fluoro-4-(2-fluoro-phenyl)-piperidine-1-carboxylic acid tert-butyl ester

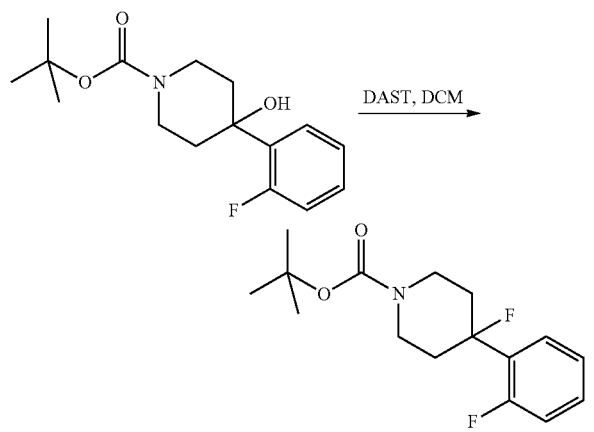

4-(2-Fluoro-phenyl)-4-hydroxy-piperidine-1-carboxylic acid tert-butyl ester (0.5 g, 1.69 mmol) in DCM (20 mL) was cooled to −78° C. Diethylaminosulphur trifluoride (2 mmol) was added and the mixture stirred for 0.5 hour and allowed to warm to room temperature. The mixture was diluted with DCM and washed with water then dried over magnesium sulphate, filtered and the solvent removed by evaporation under vacuum to give the title compound as a brown oil which was used without further purification. LCMS m/z 298.3 [M+H]⁺. R.T.=4.97 min (Analytical Method 4).

Synthesis 15

4-Fluoro-4-(2-fluoro-phenyl)-piperidine hydrochloride

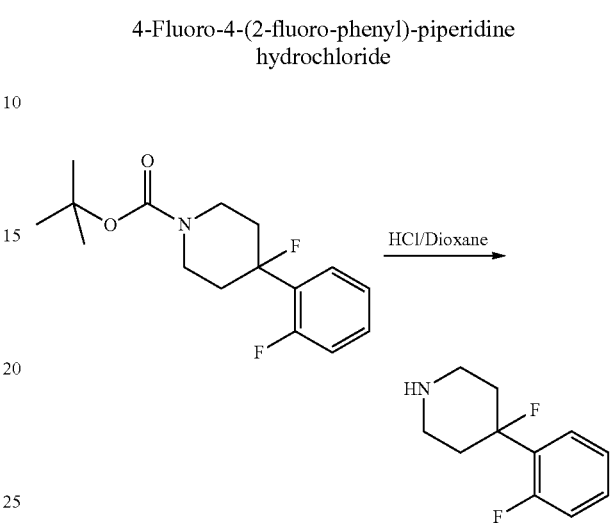

4-Fluoro-4-(2-fluoro-phenyl)-piperidine-1-carboxylic acid tert-butyl ester (0.4 g, 1.35 mmol) was dissolved in a solution of hydrogen chloride in dioxane (4 M, 3 mL) and the mixture stirred for 1 hour. The solvent was evaporated under vacuum, and the resulting solid triturated from diethyl ether to give the title compound as a pale yellow solid (0.26 g) which was used without further purification.

The following substituted piperidines were made by methods analogous to those used to prepare 4-fluoro-4-(2-fluoro-phenyl)-piperidine hydrochloride from 4-fluoro-4-(2-fluoro-phenyl)-piperidine-1-carboxylic acid tert-butyl ester:

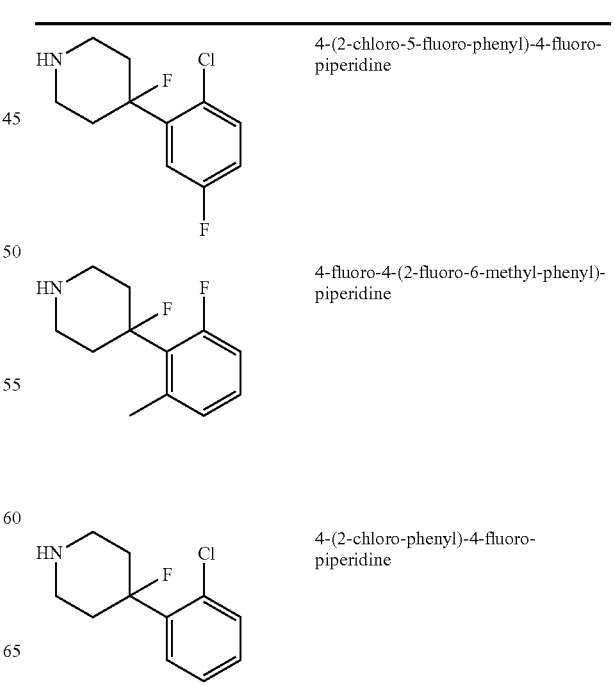

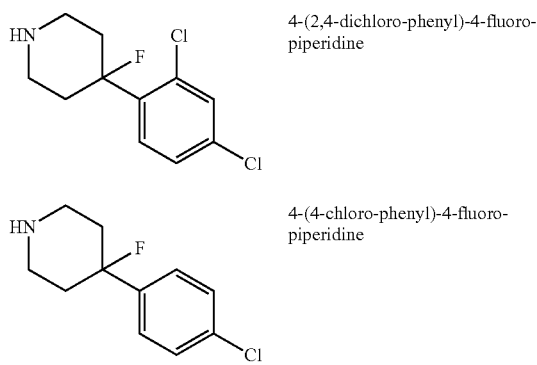

Synthesis 16

4-(2-Cyano-phenyl)-3,6-dihydro-2H-pyridine-1-carboxylic acid tert-butyl ester

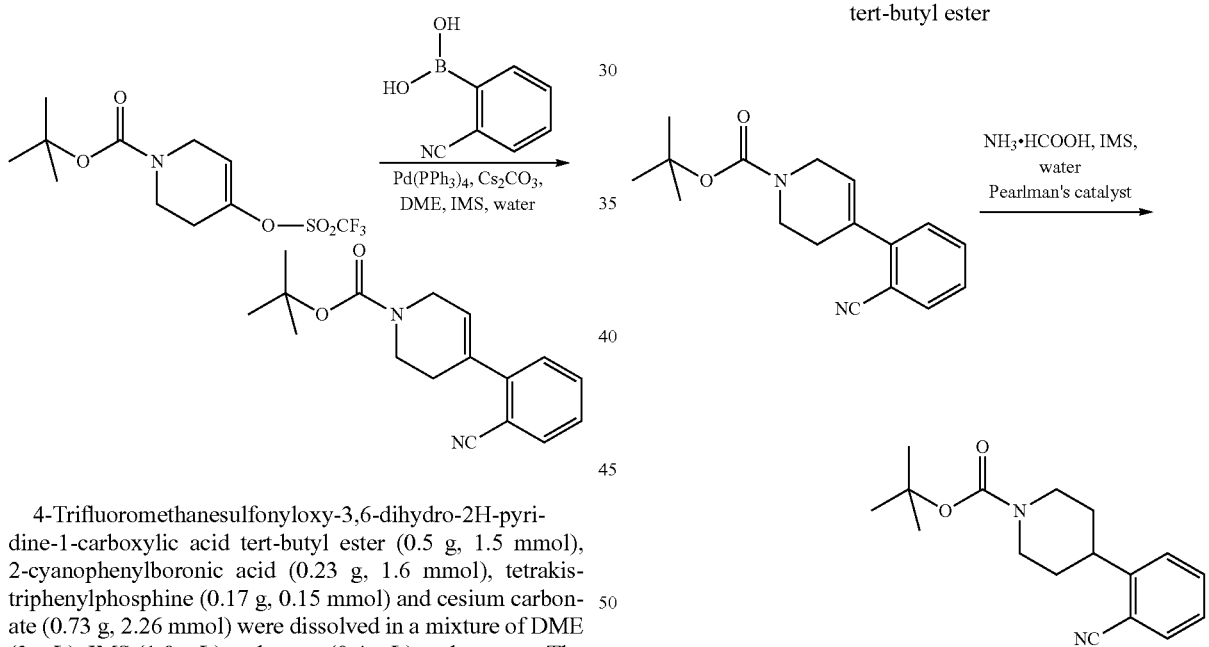

4-Trifluoromethanesulfonyloxy-3,6-dihydro-2H-pyridine-1-carboxylic acid tert-butyl ester (0.5 g, 1.5 mmol), 2-cyanophenylboronic acid (0.23 g, 1.6 mmol), tetrakistriphenylphosphine (0.17 g, 0.15 mmol) and cesium carbonate (0.73 g, 2.26 mmol) were dissolved in a mixture of DME (3 mL), IMS (1.0 mL) and water (0.4 mL) under argon. The mixture was heated by microwave irradiation to 120° C. for 0.3 hours then diluted with water. The products were extracted into DCM, dried over magnesium sulphate, filtered and the solvent removed by evaporation under vacuum. The residue was purified by flash chromatography on silica eluting with 0-20% ethyl acetate/hexane. The fractions containing the desired product were concentrated under vacuum to give the title compound as a yellow oil (0.22 g). LCMS m/z 261.2 [M+H]+. R.T.=4.59 min (Analytical Method 4).

The following substituted piperidines were made by methods analogous to those used to prepare 4-(2-cyano-phenyl)-3,6-dihydro-2H-pyridine-1-carboxylic acid tert-butyl ester from 4-trifluoromethanesulfonyloxy-3,6-dihydro-2H-pyridine-1-carboxylic acid tert-butyl ester:

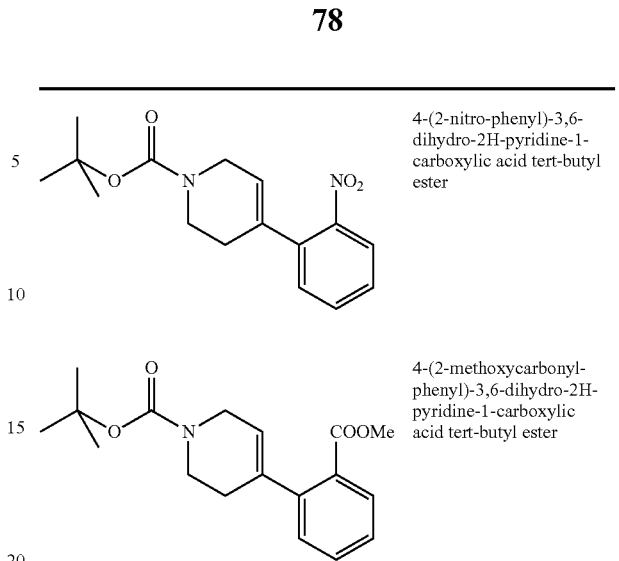

Synthesis 17

4-(2-Cyano-phenyl)-piperidine-1-carboxylic acid tert-butyl ester 4-(2-Cyano-phenyl)-3,6-dihydro-2H-pyridine-1-carboxylic acid tert-butyl ester (0.2 g) was dissolved in IMS (15 mL) and palladium on carbon (10%; 0.08 g) in water (0.5 mL) was added. Ammonium formate (0.3 g) was added and the mixture heated at reflux for 0.5 hour. The mixture was allowed to cool, filtered and the solvent removed by evaporation to give the title compound as a clear colourless oil (0.15 g). LCMS m/z 287.3[M+H]+. R.T.=4.63 min (Analytical Method 4).

The following substituted piperidine was made by methods analogous to those used to prepare 4-(2-cyano-phenyl)-piperidine-1-carboxylic acid tert-butyl ester from 4-(2-cyano-phenyl)-3,6-dihydro-2H-pyridine-1-carboxylic acid tert-butyl ester:

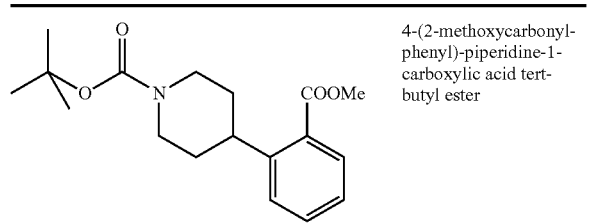

4-(2-methoxycarbonyl-phenyl)-piperidine-1-carboxylic acid tert-butyl ester

Synthesis 18

2-Piperidin-4-yl-benzonitrile

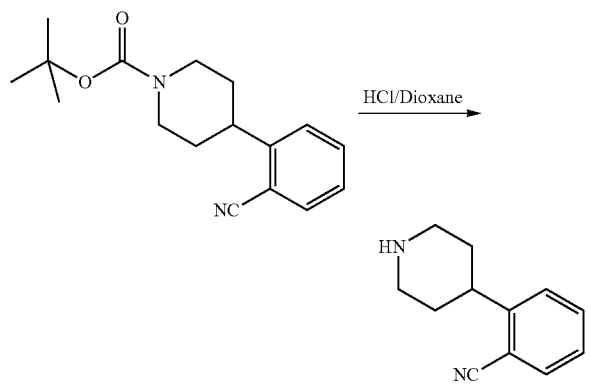

4-(2-Cyano-phenyl)-piperidine-1-carboxylic acid tert-butyl ester (0.15 g) was dissolved in a solution of hydrogen chloride in dioxane (4 M, 2 mL) and the mixture stirred for 1 hour. The solvent was evaporated under vacuum, and the resulting solid triturated from diethyl ether to give the title compound as a grey solid (0.1 g). LCMS m/z 187.2[M+H]$^+$. R.T.=1.90 min (Analytical Method 4).

The following substituted piperidines were made by analogous methods to those used to prepare 2-piperidin-4-yl-benzonitrile from 4-trifluoromethanesulfonyloxy-3,6-dihydro-2H-pyridine-1-carboxylic acid tert-butyl ester:

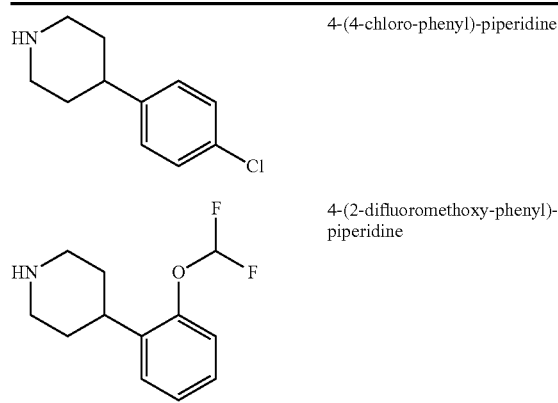

4-(4-chloro-phenyl)-piperidine 4-(2-difluoromethoxy-phenyl)-piperidine

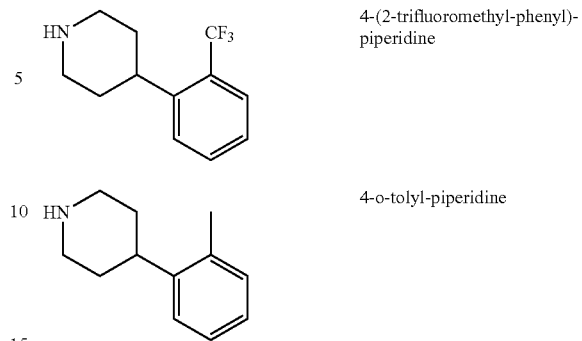

4-(2-trifluoromethyl-phenyl)-piperidine 4-o-tolyl-piperidine

8-Benzyl-3-phenyl-8-aza-bicyclo[3.2.1]oct-2-ene

Synthesis 19

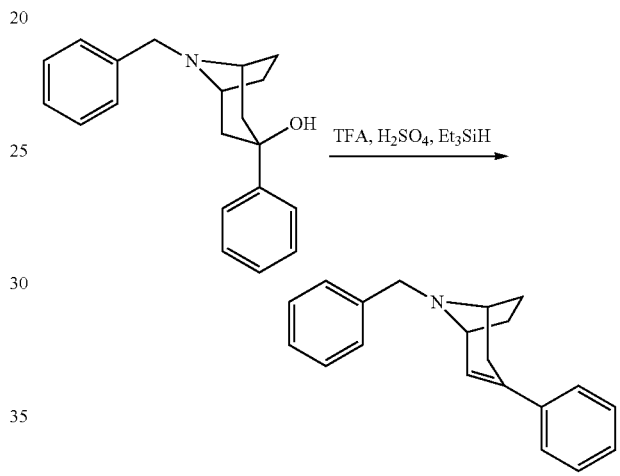

8-Benzyl-3-phenyl-8-aza-bicyclo[3.2.1]octan-3-ol (0.1 g, 0.34 mmol) was dissolved in TFA (1 mL) and cooled to 0° C. Concentrated sulphuric acid (0.054 mL) was added and the mixture stirred for 1 hour, then triethylsilane (0.17 mL) was added. After 2 hours the mixture was allowed to warm to room temperature, and then to stand for 60 hours. The mixture was concentrated under vacuum and diluted with a solution of saturated aqueous sodium carbonate. The products were extracted into DCM, dried over magnesium sulphate, filtered and the solvent removed by evaporation under vacuum to give the title compound as a colourless oil. LCMS m/z 276.5 [M+H]$^+$. R.T.=2.94 min (Analytical Method 4).

Synthesis 20

3-Phenyl-8-aza-bicyclo[3.2.1]octane

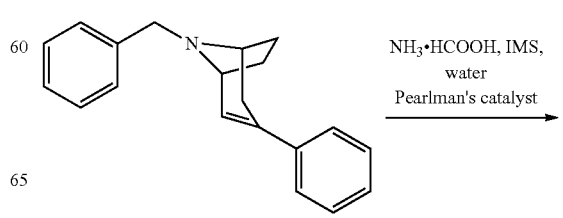

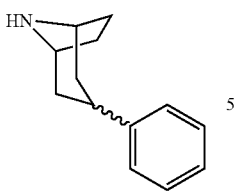

8-Benzyl-3-phenyl-8-aza-bicyclo[3.2.1]oct-2-ene (0.1 g) was dissolved in IMS (5 mL) and water (0.5 mL). Ammonium formate (0.21 g) and Pearlman's catalyst (0.02 g) were added and the mixture heated to 90° C. for 1 hour. After cooling, the mixture was filtered and concentrated under vacuum. The residue was purified on an SCX cartridge, eluting with aqueous ammonia (2 M) and methanol. The fractions containing the desired product were concentrated under vacuum to give the title compound as a colourless oil. LCMS m/z 188.4 [M+H]$^+$. R.T.=2.22 min (Analytical Method 4).

4-(2,4-Difluoro-phenyl)-1,2,3,6-tetrahydro-pyridine

Synthesis 21

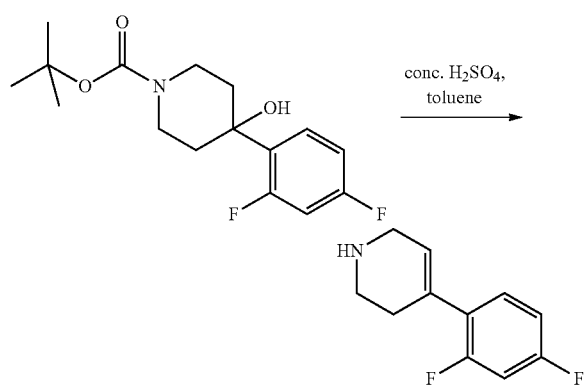

4-(2,4-Difluoro-phenyl)-4-hydroxy-piperidine-1-carboxylic acid tert-butyl ester (0.4 g) was dissolved in toluene (10 mL). Concentrated sulphuric acid (0.3 mL) was added and the mixture was heated at reflux for 2 hours and then allowed to stand at room temperature overnight. A solution of aqueous sodium hydroxide (1 N, 30 mL) was added and the products extracted into ethyl acetate. The organic solution was dried with magnesium sulphate, filtered and the solvent removed by evaporation under vacuum to give the title compound as a dark oil (0.2 g) which was used without further purification. LCMS m/z 196.1 [M+H]$^+$. R.T.=2.12 min (Analytical Method 4).

Synthesis 22

4-(2,4-Difluoro-phenyl)-piperidine hydrochloride

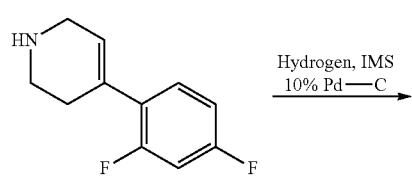

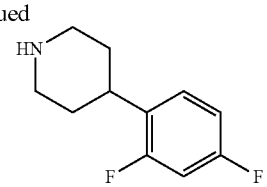

4-(2,4-Difluoro-phenyl)-1,2,3,6-tetrahydro-pyridine (0.2 g) was dissolved in ethanol (15 mL). Palladium on carbon (10%; 0.02 g) was added under nitrogen. The nitrogen atmosphere was replaced by hydrogen and the mixture stirred for 36 hours. The mixture was filtered and the solvent removed by evaporation under vacuum. The residue was dissolved in ethyl acetate and a solution of hydrogen chloride in dioxane (4 N, 1 mL) added. The resulting precipitate was isolated by filtration, washed with ether and dried under vacuum to give the title compound as a white solid (0.15 g). LCMS m/z 198.1[M+H]$^+$. R.T.=2.21 min (Analytical Method 4).

Synthesis 23

1-Benzyl-4-(2-benzyloxy-phenyl)-piperidin-4-ol

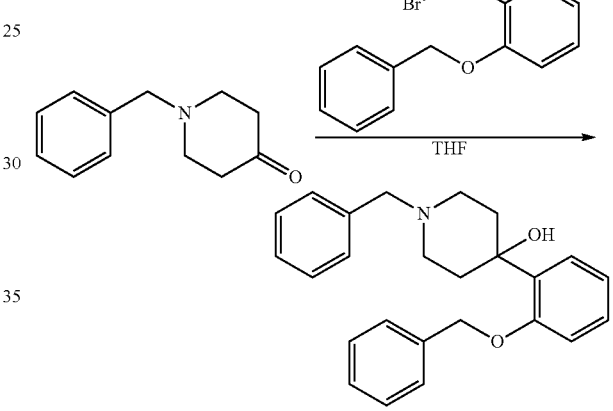

A solution of 1-benzyl-4-piperidone (0.5 g, 2.6 mmol) in THF (10 mL) was cooled to −78° C. and 2-(benzyloxy)phenyl magnesium bromide (3.2 mmol) was added. The mixture was stirred for 0.5 hours then allowed to warm to room temperature. Hydrochloric acid (1 N, 10 mL) was added carefully and the mixture stirred for 0.1 hour before adding a solution of aqueous sodium hydroxide (1 N, 30 mL). The products were extracted into ethyl acetate, dried over magnesium sulphate, filtered and the solvent removed by evaporation under vacuum. The residue was purified by flash chromatography on silica eluting with 0-50% ethyl acetate/hexane. The fractions containing the desired product were concentrated under vacuum to give the title compound (0.6 g) as a clear, colourless oil.

LCMS m/z 374.5 [M+H]$^+$. R.T.=3.44 min (Analytical Method 4).

Synthesis 24

4-(2-Hydroxy-phenyl)-piperidin-4-ol hydrochloride

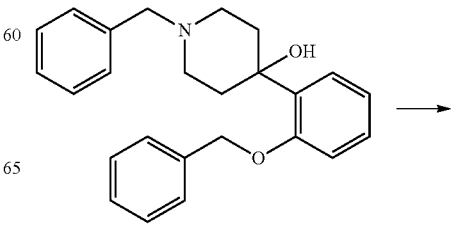

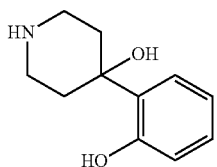 [SMILES: OC1(c2ccccc2Cl)CCNCC1]

1-Benzyl-4-(2-benzyloxy-phenyl)-piperidin-4-ol (0.6 g, 1.6 mmol) was dissolved in ethanol (30 mL) and a suspension of palladium on carbon (10%; 0.3 g) in water (5 mL) was added. Ammonium formate (1 g) was added and the mixture heated at reflux for 0.5 hour. The mixture was allowed to cool, filtered and the solvent removed by evaporation under vacuum. The residue was dissolved in diethyl ether and a solution of hydrogen chloride in dioxan (4 N, 1 mL) added. The resulting precipitate was isolated by filtration, washed with diethyl ether and dried under vacuum to give the title compound as a white solid (0.2 g). LCMS m/z 194.3 [M+H]$^+$. R.T.=0.35 min (Analytical Method 4).

Synthesis 25

(4-Phenyl-piperidin-4-yl)-methanol

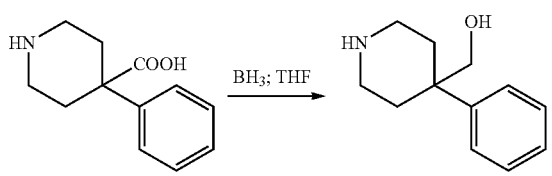 [SMILES: O=C(O)C1(c2ccccc2)CCNCC1 ; OCC1(c2ccccc2)CCNCC1]

4-Phenyl-piperidine-4-carboxylic acid (1.0 g, 2.7 mmol) was added to a solution of borane in THF (1 M, 15 mL). The mixture was then heated at reflux for 1 hour, and then methanol (3 mL) was carefully added dropwise. The mixture was heated at reflux for 1 hour and allowed to cool to room temperature and hydrochloric acid (1 N, 2 mL) was added and the mixture left to stand overnight. The solvent was then removed by evaporation under vacuum and the residue triturated with acetone. The resulting solid was isolated by filtration, washed with diethyl ether and dried under vacuum to afford the title compound as a white solid (0.37 g). LCMS m/z 192.2 [M+H]$^+$. R.T.=0.69 min (Analytical Method 4).

Synthesis 26

5-Bromo-thiophene-3-carboxylic acid

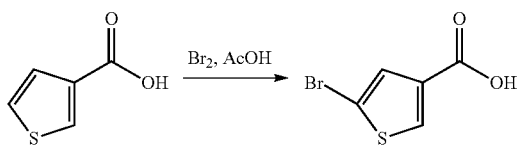 [SMILES: O=C(O)c1ccsc1 ; O=C(O)c1csc(Br)c1]

Thiophene-3-carboxylic acid (25 g, 195 mmol) was dissolved in acetic acid (200 mL). Bromine (10.4 mL, 200 mmol) was added slowly over the course of 0.5 hour. The mixture was stirred for a further 0.5 hour and then poured onto ice. After 0.5 hours the white precipitate that formed was collected by filtration. Recrystallisation from water gave the title compound as a white solid (13.7 g). $^1$H NMR (400 MHz, d$_6$-DMSO): δ 8.25 (s, 1H), 7.45 (s, 1H).

Synthesis 27

5-Bromo-thiophene-3-carboxylic acid methyl ester

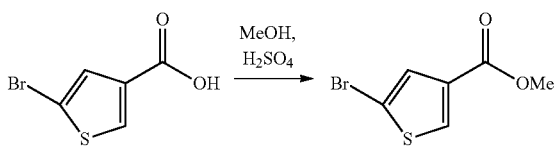 [SMILES: O=C(O)c1csc(Br)c1 ; COC(=O)c1csc(Br)c1]

5-Bromo-thiophene-3-carboxylic acid (13 g, 64 mmol) was dissolved in methanol (140 mL). Concentrated sulphuric acid (6.5 mL) was added and the mixture heated at reflux for 14 hours. The reaction was quenched by adding a solution of saturated aqueous sodium bicarbonate and most of the solvent was removed by evaporation under vacuum. The mixture was then diluted with a solution of saturated aqueous sodium bicarbonate and the product extracted with DCM. The organic solution was dried over sodium sulphate, filtered and the solvent removed by evaporation to give a white crystalline solid (13.2 g). $^1$H NMR (400 MHz, CDCl$_3$): δ 8.0 (s, 1H), 7.5 (s, 1H), 3.85 (s, 3H).

Synthesis 28

5-(1H-Pyrazol-4-yl)-thiophene-3-carboxylic acid methyl ester

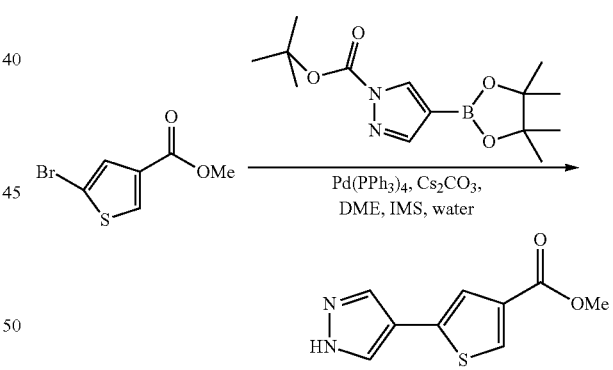

5-Bromo-thiophene-3-carboxylic acid methyl ester (6 g, 27 mmol) was dissolved in a mixture of DME (75 mL), IMS (25 mL) and water (12.5 mL). Caesium carbonate (13.2 g, 40 mmol) and 4-(4,4,5,5-tetramethyl-[1,3,2]dioxaborolan-2-yl)-pyrazole-1-carboxylic acid tert-butyl ester (9.2 g, 31 mmol) were added and the mixture stirred under argon. Palladium tetrakis-(triphenylphosphine) (3.1 g, 2.7 mmol) was then added and the mixture heated at 110° C. for 6 hours. The mixture was allowed to cool to room temperature and then diluted with water. The product was extracted into DCM and washed with brine, then dried over sodium sulphate, filtered and the solvent removed by evaporation under vacuum. The residue was triturated with diethyl ether to give the title compound as a pale yellow solid (3.01 g). LCMS m/z 209.1

[M+H]⁺. R.T.=3.72 min (Analytical Method 4). ¹H NMR (400 MHz, d6-DMSO): δ 8.2 (s, 1H), 8.15 (s, 1H), 7.85 (s, 1H), 7.5 (s, 1H), 3.8 (s, 3H).

Synthesis 29

5-(1H-Pyrazol-4-yl)-thiophene-3-carboxylic acid

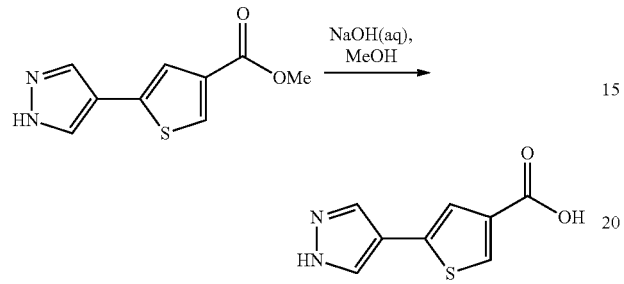

5-(1H-Pyrazol-4-yl)-thiophene-3-carboxylic acid methyl ester (2.8 g, 13.3 mmol) was dissolved in a mixture of methanol (18 mL) and a solution of aqueous sodium hydroxide (1 N, 18 mL) and the mixture stirred at 50° C. for 1.5 hours. The mixture was concentrated under vacuum and acidified with aqueous hydrochloric acid (1N). The resulting precipitate was isolated by filtration and washed with water before drying under vacuum to give the title compound as a white solid (1.77 g). LCMS m/z 195.1 [M+H]⁺. R.T.=3.23 min (Analytical Method 4). ¹H NMR (400 MHz, d6-DMSO): δ 8.1 (s, 1H), 8.0 (m, 2H), 7.45 (s, 1H).

The following substituted carboxylic acid was made by analogous methods to those used to prepare 5-(1H-pyrazol-4-yl)-thiophene-3-carboxylic acid from 5-bromo-thiophene-3-carboxylic acid methyl ester:

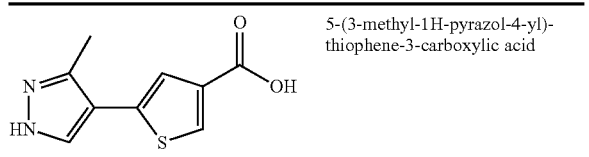

5-(3-methyl-1H-pyrazol-4-yl)-thiophene-3-carboxylic acid

Synthesis 30

4-(2-Nitro-phenyl)-1,2,3,6-tetrahydro-pyridine hydrochloride

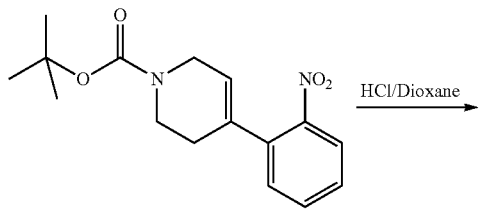

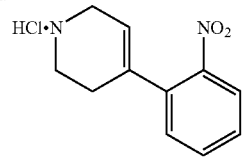

4-(2-Nitrophenyl)-3,6-dihydro-2H-pyridine-1-carboxylic acid tert-butyl ester (0.45 g) was dissolved in a solution of hydrogen chloride in dioxane (4 N, 4 mL). After stirring for 0.5 hour at 50° C., the solvent was removed by evaporation and the residue triturated with diethyl ether to give the title compound as a white solid (0.29 g). LCMS m/z 205.2 [M+H]⁺. R.T.=3.80 min (Analytical Method 4).

Synthesis 31

1-[4-(2-Nitro-phenyl)-3,6-dihydro-2H-pyridin-1-yl]ethanone

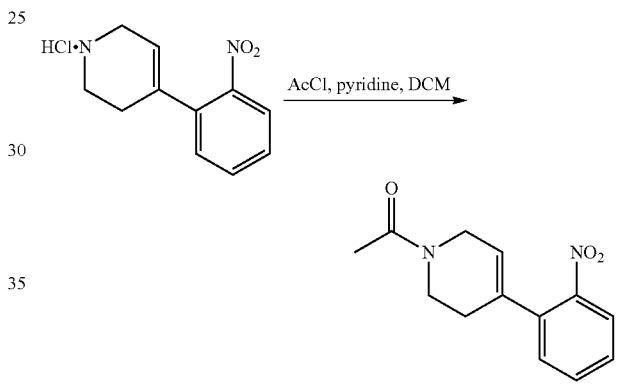

4-(2-Nitro-phenyl)-1,2,3,6-tetrahydro-pyridine hydrochloride (0.44 g, 1.8 mmol) was dissolved in a solution of pyridine (0.4 mL) and DCM (20 mL). Acetyl chloride (0.142 mL) was added and the mixture was stirred for 0.5 hours. The mixture was diluted with DCM (20 mL) and the organic solution washed with water then 1 N hydrochloric acid. The solution was dried with magnesium sulphate, filtered and the solvent removed by evaporation under vacuum to give the title compound as an orange oil (0.4 g). LCMS m/z 247.4 [M+H]⁺. R.T.=3.70 min (Analytical Method 4).

Synthesis 32

1-[4-(2-Amino-phenyl)-piperidin-1-yl]ethanone

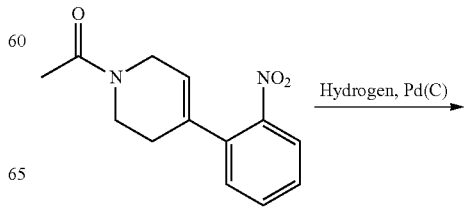

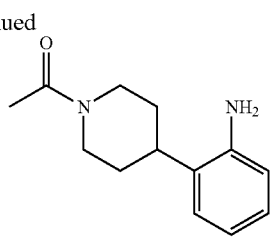

1-[4-(2-Nitro-phenyl)-3,6-dihydro-2H-pyridin-1-yl]ethanone (0.43 g, 1.8 mmol) was dissolved in a solution of ammonium formate (1.13 g, 18 mmol) in IMS (20 mL) and water (20 mL). Palladium on carbon (10% w/w, 0.2 g) was then added and the mixture heated at reflux for 1 hour. The solution was filtered and then the solvent removed by evaporation under vacuum. The residue was dissolved in ethyl acetate (50 mL) and the resulting solution washed with saturated aqueous sodium hydrogen carbonate solution, dried over magnesium sulphate, filtered and the solvent removed by evaporation under vacuum to give the title compound as a pale pink oil (0.3 g). LCMS m/z 219.38 [M+H]$^+$. R.T.=2.29 min (Analytical Method 4).

Synthesis 33

1-[4-(2-Chloro-phenyl)-piperidin-1-yl]-ethanone

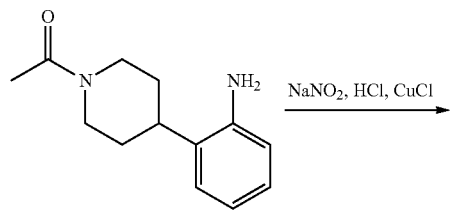

1-[4-(2-Amino-phenyl)-piperidin-1-yl]-ethanone (0.3 g, 1.38 mmol) was dissolved in a solution of hydrochloric acid (6 N, 6 mL) and cooled to 0° C. A solution of sodium nitrite (0.097 g, 1.4 mmol) in water (1 mL) was added drop wise and the mixture stirred for 1 hour. The resulting solution was added drop wise to a solution of copper (I) chloride (0.35 g, 3.5 mmol) in hydrochloric acid (6 N, 6 mL). The mixture was allowed to warm to room temperature, and was then diluted with water (20 mL) and the products extracted into ethyl acetate. The organic solution was washed with water (20 mL) then dried over magnesium sulphate, filtered and the solvent removed by evaporation under vacuum to give the title compound as an orange oil (0.2 g). LCMS m/z 238.2 [M+H]$^+$. R.T.=4.30 min (Analytical Method 4).

Synthesis 34

4-(2-Chloro-phenyl)-piperidine hydrochloride

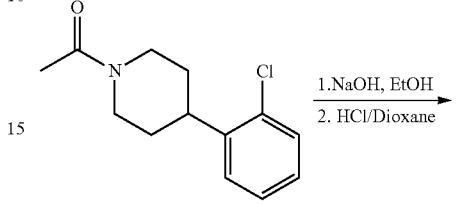

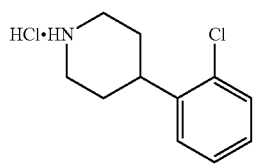

1-[4-(2-Chloro-phenyl)-piperidin-1-yl]-ethanone (0.2 g) was dissolved in a solution of aqueous sodium hydroxide (1 N, 5 mL) and ethanol (10 mL) and heated to 50° C. for 6 hours. The solvent was removed by evaporation under vacuum, and the products extracted into ethyl acetate, washed with water (20 mL) then dried over magnesium sulphate, filtered and the solvent removed by evaporation under vacuum. The residue was dissolved in a solution of hydrogen chloride in dioxane (4 N, 1 mL) and the solvent evaporated to give the title compound as a pale yellow solid (0.12 g). LCMS m/z 196.1 [M+H]$^+$. R.T.=2.46 min (Analytical Method 4).

Synthesis 35

4-(2-Hydroxymethyl-phenyl)-piperidine-1-carboxylic acid tert-butyl ester

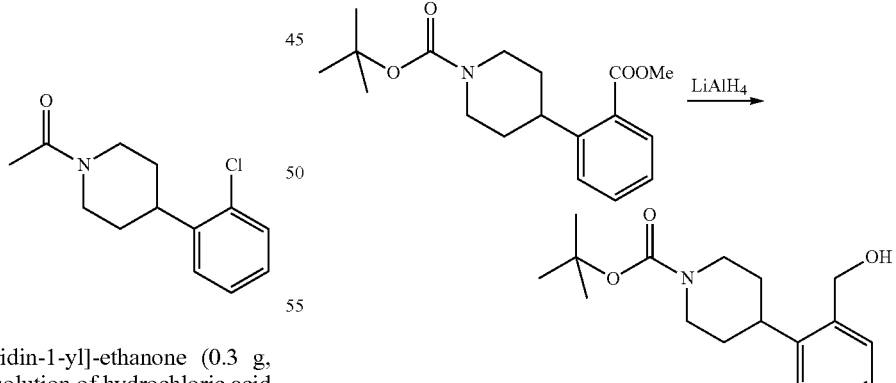

Lithium aluminium hydride (0.026 g, 0.7 mmol) was suspended in dry THF (1 mL) under a nitrogen atmosphere and cooled in an ice bath. A solution of 4-(2-methoxycarbonyl-phenyl)-piperidine-1-carboxylic acid tert-butyl ester (0.27 g, 0.7 mmol) in dry THF (2 mL) was added drop wise and the reaction mixture stirred for 1 hour. The reaction mixture was diluted with diethyl ether (5 mL) and quenched with hydrochloric acid (1 N, 5 mL). The organic solution was separated and washed with saturated aqueous sodium hydrogen carbonate (5 mL) and brine (5 mL), dried over magnesium sulphate, filtered and the solvent removed under vacuum to give the title compound as a colourless gum (0.13 g). LCMS m/z 292.0 [M+H]$^+$. R.T.=4.57 min (Analytical Method 4).

Synthesis 36

(2-Piperidin-4-yl-phenyl)-methanol hydrochloride

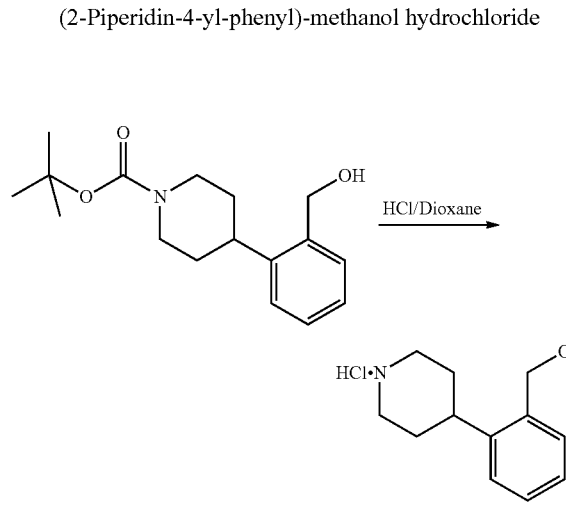

4-(4-(2-Hydroxymethyl-phenyl)-piperidine-1-carboxylic acid tert-butyl ester (0.13 g, 0.44 mmol) was dissolved in a solution of hydrogen chloride in dioxane (4 N, 2 mL). The mixture was stirred for 1 hour and the solvent removed by evaporation under vacuum. The solid was triturated from ether to afford the title compound as a white solid (0.08 g). LCMS m/z 192.2 [M+H]$^+$. R.T.=0.72 min (Analytical Method 4).

Synthesis 37

1-Benzyl-4-methyl-piperidin-4-ol

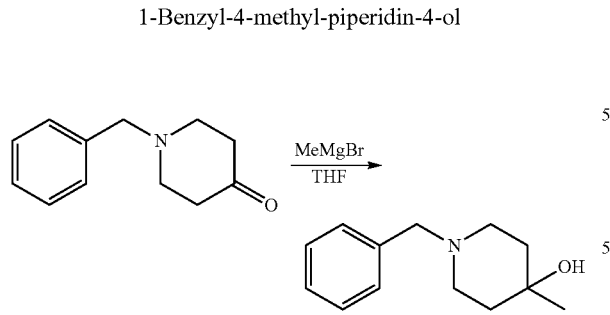

A solution of 1-benzyl-4-piperidone (26.5 mmol, 5 g) in THF (50 mL) was cooled to −15° C. and a solution of methyl magnesium bromide in ether (3 M, 22 mL) was added. The mixture was stirred for 0.5 hours then allowed to warm to room temperature. Saturated aqueous ammonium chloride (50 mL) was added and the products were extracted into ethyl acetate, dried over magnesium sulphate, filtered and the solvent removed by evaporation under vacuum to give the title compound as a pale yellow solid (5.0 g) that was used directly without further purification.

Synthesis 38

1-Benzyl-4-(2-chloro-phenyl)-4-methylpiperidine

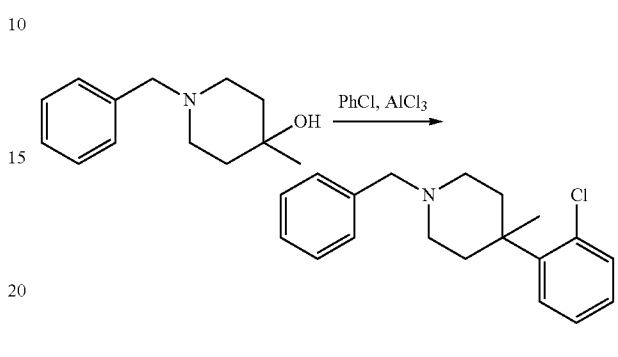

1-Benzyl-4-methyl-piperidin-4-ol (4.5 g) was dissolved in chlorobenzene (50 mL). Aluminium trichloride (15 g) was added portion wise and the mixture then heated at reflux for 0.5 hours. The mixture was then allowed to cool and poured over ice. The resulting solution was treated with sodium hydroxide until basic and the products extracted into ethyl acetate, dried over magnesium sulphate, filtered and the solvent removed by evaporation under vacuum. The residue was purified by silica chromatography eluting with a mixture of ethyl acetate and hexane. The fractions containing the desired products were combined and the solvent removed by evaporation to give a 4:1 mixture of the title compound and 1-benzyl-4-(4-chloro-phenyl)-4-methyl-piperidine which was used directly without further purification.

Synthesis 39

4-(2-Chloro-phenyl)-4-methyl-piperidine

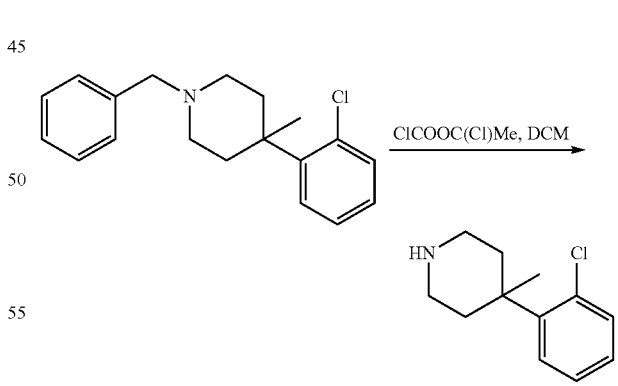

The mixture of 1-benzyl-4-(2-chloro-phenyl)-4-methylpiperidine and 1-benzyl-4-(4-chloro-phenyl)-4-methyl-piperidine (1.6 g) was dissolved in methanol (30 mL) and 1-chloroethylchloroformate (0.9 mL) was added. The mixture was heated at reflux for 10 minutes and allowed to cool. The solvent was removed by evaporation under vacuum and the residue precipitated from ethyl acetate with ether to give a 4:1 mixture of the title compound and 4-(4-chloro-phenyl)-4- methyl-piperidine which was used directly without further purification. LCMS m/z 210.2 [M+H]+. R.T.=2.64 min (Analytical Method 4).

Synthesis 40

4-(2-Chloro-phenyl)-4-cyano-piperidine-1-carboxylic acid tert-butyl ester

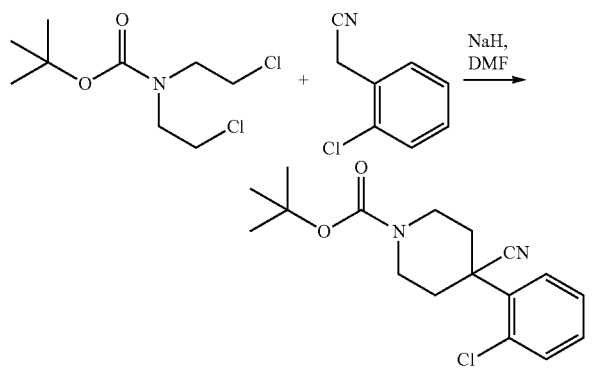

Sodium hydride (60% dispersion in mineral oil, 1.28 g, 45 mmol) was suspended in DMF (20 mL) and cooled in an ice bath under a nitrogen atmosphere. (2-Chloro-phenyl)-acetonitrile (1.77 g, 11.7 mmol) in DMF (5 mL) was added slowly, and the mixture stirred for 2 hours. Bis-(2-chloro-ethyl)-carbamic acid tert-butyl ester (3.3 g, 11.1 mmol) in DMF (5 mL) was then added and the mixture heated to 75° C. for 6 hours. The solvent was removed by evaporation under vacuum and the residue dissolved in ethyl acetate (50 mL), washed with water, then brine, dried over magnesium sulphate, filtered and the solvent removed by evaporation under vacuum. The residue was purified by silica chromatography eluting with a mixture of ethyl acetate and hexane. The fractions containing the desired products were combined and the solvent removed by evaporation to give the title compound as an orange gum (1.1 g). LCMS m/z 321.0 [M+H]+. R.T.=4.76 min (Analytical Method 4).

Synthesis 41

4-(2-Chloro-phenyl)-piperidine-4-carbonitrile hydrochloride

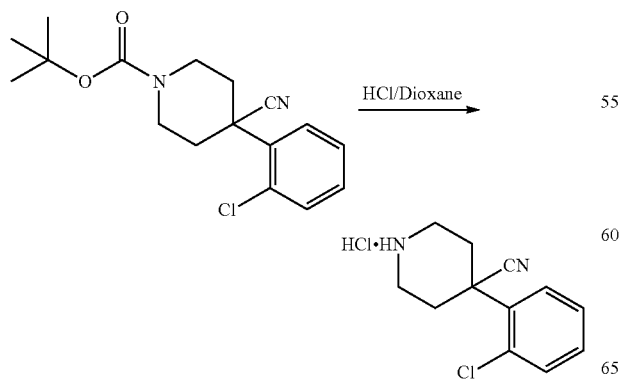

4-(2-Chloro-phenyl)-4-cyano-piperidine-1-carboxylic acid tert-butyl ester (0.25 g, 0.78 mmol) was dissolved in a solution of hydrogen chloride in dioxane (4 N, 1 mL). The mixture was stirred for 1 hour and the solvent removed by evaporation under vacuum. The solid was triturated from ether to afford the title compound as a yellow solid (0.178 g). LCMS m/z 221.2 [M+H]+. R.T.=2.18 min (Analytical Method 4).

Synthesis 42

3-(2-Chloro-phenyl)-8-aza-bicyclo[3.2.1]octan-3-ol

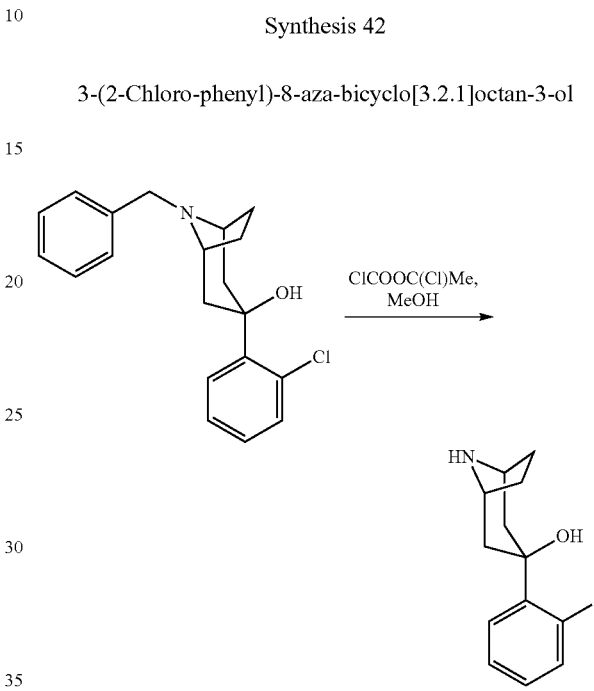

8-Benzyl-3-(2-chloro-phenyl)-8-aza-bicyclo[3.2.1]octan-3-ol (0.30 g, 0.93 mmol) was dissolved in methanol (5 mL) and 1-chloroethylchloroformate (0.14 mL) was added. The mixture was heated at reflux for 6 hours and allowed to cool. The solvent was removed by evaporation under vacuum and the residue precipitated from ethyl acetate with ether to give a white solid (0.12 g, 56%). LCMS m/z 287.2 [M+H]+. R.T.=1.96 min (Analytical Method 4).

Synthesis 43

(8-Fluoro-8-phenyl-3-aza-bicyclo[3.2.1]oct-3-yl)-[5-(1H-pyrazol-4-yl)-thiophen-3-yl]methanone (AA-39)

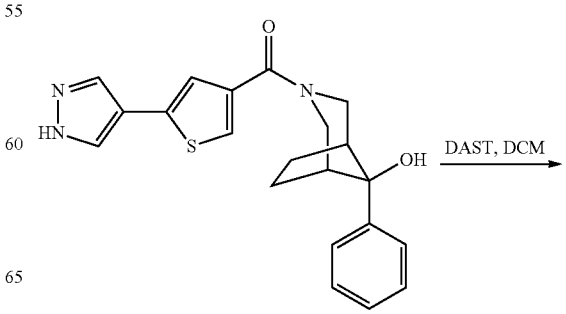

-continued

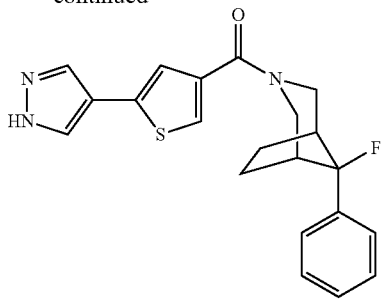

(8-Hydroxy-8-phenyl-3-aza-bicyclo[3.2.1]oct-3-yl)-[5-(1H-pyrazol-4-yl)-thiophen-3-yl]methanone (0.05 g, 0.12 mmol) in DCM (2 mL) was cooled to −78° C. under an atmosphere of nitrogen. Diethylaminosulphur trifluoride (0.05 mL) was added and the mixture stirred for 0.25 hour and allowed to warm to room temperature over 1 hour. The mixture was diluted with DCM and washed with water then dried over magnesium sulphate, filtered and the solvent removed by evaporation. The residue was purified by reverse phase HPLC and the fractions containing the desired products were combined and the solvent removed by lyophilisation to give the title compound as a white solid (0.02 g). LCMS m/z 382.1 [M+H]$^+$. RT.=4.25 min (Analytical Method 2).

Biological Methods

Cellular In Vitro 11β-HSD1 Enzyme Inhibition Assay

Compounds were assessed by a Scintillation Proximity Assay (SPA) performed according to the following protocol:

HEK293 cells were stably transfected with a construct containing the full-length gene coding for the human 11β-HSD1 enzyme to create HEK293/11β-HSD1 cells. Cells were routinely cultured in DMEM containing 10% calf foetal serum, 1% glutamine, and 1% penicillin and streptomycin. Prior to assay, cells were plated at 2×10$^4$ cells/well in 96-well poly-D-Lys coated flat-bottomed microplates and incubated in 5% $CO_2$, 95% $O_2$ at 37° C. for 24 hours. The media in each well was removed immediately before assay.

Compounds to be tested were dissolved in DMSO at 10 mM and serially diluted into water containing 10% DMSO. Diluted compounds at a volume of 10 μL were added to wells of a 96-well V-bottomed microplate. A solution of DMEM, 1% glutamine, 1% penicillin and streptomycin, and 22 nM tritiated cortisone was prepared and 90 μL added to each well of the assay plate. This solution (100 μL/well) was transferred to the plate containing the cells. The plate was then incubated in 5% $CO_2$, 95% $O_2$ at 37° C. for 2 hours.

Following this incubation, 50 μL of the assay solution was transferred to each well of a 96-well scintillation microplate. A mixture consisting of anti-mouse YSi SPA beads, pre-mixed with anti-cortisol antibody in assay buffer (50 mM Tris.HCl, pH 7.0; 300 mM NaCl; 1 mM EDTA, 5% glycerol) was prepared and 50 μL added to each well of the scintillation microplate. An adhesive strip was applied to the microplate and the plate gently shaken for at least 2 hours at room temperature, and then spun briefly on a low speed centrifuge. The plate was read on a scintillation counter suitable for 96-well microplates. For the calculation of percentage inhibition, a series of wells were added to the plate that represented the assay maximum and the assay minimum: one set that contained substrate without cells (minimum) and another set that contained substrate and cells without any compound (maximum).

The calculation of median inhibitory concentration (IC$_{50}$) values for the compounds was performed using GraphPad Prism® software. Dose-response curves for each compound were plotted as fractional inhibition and data fitted to the four parameter logistic equation.

Cellular In Vitro 11β-HSD2 Enzyme Inhibition Assay

For measurement of inhibition of 11β-HSD2, CHO cells stably transfected with the full-length gene coding for human 11β-HSD2 were used. Assays were carried out in 96-well microplates containing 1×10$^5$ cells/well. Controls and compounds were plated as above, so that the final DMSO concentration in each well was 1%. To initiate the assay, 90 μL of a solution of HAMS F-12 medium containing 1% glutamine, 1% penicillin and streptomycin, and 22 nM tritiated cortisol was added to each well of the assay plate. The plate was then incubated in 5% $CO_2$, 95% $O_2$ at 37° C. for 16 hours.

The assay solutions were transferred to glass tubes and 20 μL ethyl acetate added to each tube. Each tube was vortexed thoroughly and the upper layer containing the tritiated steroid transferred to a fresh glass tube. The solvent was evaporated by placing the tubes in a heating block at 65° C. under a stream of Nitrogen gas. 20 μL ethanol was added to each of the dried samples and vortexed briefly. Each sample was applied to a silica TLC plate and the plate dried. The plate was placed vertically in a glass tank containing 92% chloroform:8% ethanol and the solvent allowed to rise up the plate. The plate was dried, placed in an imaging cassette, and overlayed with a tritium imaging plate for 1-2 days. The amount of enzyme inhibition in each sample was determined by measuring the intensity of the substrate and product spots using a phosphoimager.

IC$_{50}$ values for inhibitors were determined as described for 11β-HSD1.

In Vitro Human Liver Microsomal Stability Assay

To predict in vivo metabolism of compounds, the stability of compounds incubated with human liver microsomes in vitro was determined. Human liver microsome preparations were stored at −80° C. and thawed on ice prior to use. The thawed microsomes were diluted to a concentration of 2 mg/mL in 50 mM sodium phosphate, pH 7.4. Reference and test compounds were prepared as 10 mM stocks in 100% DMSO and diluted to 1 mM in acetonitrile before use. Each compound was tested in triplicate as follows:

4 μL of test or reference compound was added to a well of a 24-well microplate and 0.5 mL of 4 mM NADPH added. The plate was then transferred to a shaker for 10 minutes at room temperature. 30 μL of the compound/NADPH solution was transferred to the well of a 96-well microplate and incubated at 37° C. for 5 minutes. 30 μL of human liver microsomes (pre-incubated at 37° C. for 5 minutes) was added to the well containing the compound/NADPH solution and the plate incubated for the selected period of time (typically 0 or 30 minutes). The reaction was stopped by adding 60 μL of ice cold 300 μM trichloroacetic acid. The plate was centrifuged at 1000 rpm for 5 minutes at room temperature and the supernatant transferred to the well of a new 96-well v-bottomed microplate for mass spectrometric analysis.

Samples were analyzed by TSQ Quantum Discovery Tandem Mass Spectrometer and Surveyor Liquid Chromatogram (Thermo, Hemel-Hempstead, UK). 10 μL of each sample was injected in a mobile phase consisting of 60%:40% methanol:5 mM ammonium acetate at a flow rate of 0.5 mL/minute. The column used was a BDS hypersil, C18, 50×2.1 mm with a 5 μm particle size.

Each compound was tuned with a spray voltage of 3000 V and a capillary temperature of 300° C. and values for tube lens, CID and product ions were determined.

The peak area for each compound was measured in triplicate for the 0 and 30 minute samples and the average of each was reported. The percentage remaining after 30 minutes was calculated as the average peak area of the sample after 30 minutes divided by the average peak area at 0 minutes. The RSD was 10% or lower for each compound.

Pharmacokinetics in Rat

The pharmacokinetics of certain compounds were determined following intravenous (1 mg/kg) and oral (10 mg/kg) administration to male Sprague Dawley rats. Dosing solution was prepared by mixing each compound with 2% DMSO, 38% PEG-400 and 60% (0.9%) NaCl. Solutions were passed through 0.2 µm filters prior to administration.

Following dosing and at appropriate time points, blood samples were taken from a lateral tail vein and transferred into a tube pre-treated with EDTA. Blood samples were analysed for parent compound by LCMS and the quantity of parent compound remaining determined. Non-compartmental analysis was applied to the data using WinNonlin™ software to determine the pharmacokinetic parameters for each compound.

Biological Data

Cellular In Vitro Enzyme Inhibition Data

The following compounds were tested using the cellular in vitro enzyme inhibition assays described above: AA-01 through AA-41, and BB-01 through BB-15, All of the compounds tested have an $IC_{50}$ for 11β-HSD1 of less than about 10 µM. Many of the compounds have an $IC_{50}$ for 11β-HSD1 of less than about 1 µM. Many of the compounds have an $IC_{50}$ for 11β-HSD1 of less than about 500 nM.

Generally, the $IC_{50}$ ratio for 11β-HSD2 to 11β-HSD1 is at least about five or greater, and in many cases ten or greater. For example, data for some of the compounds is shown in the following table.

TABLE 1

In vitro Enzyme Inhibition Data

| Compound No. | $IC_{50}$ for 11β-HSD1 (HEK293) | $IC_{50}$ for 11β-HSD2 (CHO) |
|---|---|---|
| AA-01 | 208 nM | >10,000 nM |
| AA-04 | 44 nM | >10,000 nM |
| AA-06 | 21 nM | >10,000 nM |
| AA-08 | 10 nM | >10,000 nM |
| AA-12 | 99 nM | >10,000 nM |
| AA-15 | 110 nM | >10,000 nM |
| AA-18 | 104 nM | >10,000 nM |
| AA-22 | 38 nM | >10,000 nM |
| AA-30 | 15 nM | >10,000 nM |
| AA-33 | 19 nM | >10,000 nM |
| AA-36 | 42 nM | >10,000 nM |
| AA-37 | 35 nM | >10,000 nM |
| BB-03 | 107 nM | >10,000 nM |
| BB-08 | 114 nM | >10,000 nM |
| BB-11 | 638 nM | >10,000 nM |

The following compounds have an $IC_{50}$ for 11β-HSD1 (HEK293) of less than or equal to 500 nM (0.5 µM): AA-01, AA-02, AA-04, AA-05, AA-06, AA-07, AA-08, AA-09, AA-11, AA-12, AA-13, AA-14, AA-15, AA-16, AA-18, AA-21, AA-22, AA-23, AA-24, AA-25, AA-26, AA-27, AA-28, AA-29, AA-30, AA-31, AA-33, AA-34, AA-36, AA-37, AA-38, AA-40, BB-03, BB-04, BB-05, BB-07, BB-08, BB-09, BB-12, BB-14 and BB-15.

The following compounds have an $IC_{50}$ for 11β-HSD1 (HEK293) of more than 500 nM (0.5 µM) and less than or equal to 1000 nM (1 µM): AA-03, AA-17, AA-32, AA-35, BB-01, BB-06, BB-10, BB-11 and BB-13.

The following compounds have an $IC_{50}$ for 11β-HSD1 (HEK293) of more than 1000 nM (1.0 µM) and less than or equal to 10 µM: AA-10, AA-19, AA-20, AA-39, AA-41 and BB-02.

Human Liver Microsomal Stability Data

Data for some of the compounds are shown in the following table.

TABLE 2

Human Liver Microsomal Stability Data

| Compound No. | % Parent Remaining at 30 min[a] |
|---|---|
| AA-01 | +++ |
| AA-02 | +++ |
| AA-04 | +++ |
| AA-05 | +++ |
| AA-06 | +++ |
| AA-07 | +++ |
| AA-08 | ++ |
| AA-09 | +++ |
| AA-15 | ++ |
| AA-16 | + |
| AA-17 | +++ |
| AA-18 | ++ |
| AA-22 | +++ |
| AA-30 | ++ |
| AA-33 | + |
| AA-36 | + |
| AA-37 | ++ |
| BB-01 | +++ |
| BB-03 | + |
| BB-04 | ++ |
| BB-05 | ++ |
| BB-06 | +++ |
| BB-07 | + |
| BB-08 | ++ |
| BB-13 | +++ |

[a]Parent remaining after 30 minutes: 0-30% +; 31-60% ++; 61-100% +++.

Compounds administered in vivo usually undergo metabolism, which occurs predominantly in the liver and to a lesser extent in the gut. Metabolism of compounds typically generates polar species that are cleared more rapidly from the body than the parent compound. One method of increasing the concentration of a compound in the body is to slow down its metabolism in the liver (and gut) and hence reduce its clearance from the body. If a compound is administered orally and metabolism in the gut wall occurs, slowing the metabolism of a compound may also increase its absorption through the intestine leading to increased oral bioavailability. Increasing the metabolic stability and lowering the clearance of a compound is desirable since it helps to maintain levels of the compound in the body and can prolong the duration of action of the compound.

Incubation of compounds with human liver microsomes is commonly used to predict the metabolism of compounds in vivo. Compounds with high microsomal stability are generally favoured since this often correlates with an improved pharmacokinetic profile in vivo.

The majority of the PPPT compounds tested in human microsomal stability assays have high microsomal stability (61-100% parent compound remaining). Fewer compounds have moderate microsomal stability (31-60% parent compound remaining) and fewer still have low microsomal stability (0-30%).

Rat Pharmacokinetic Data

Data for some of the compounds are shown in the following table:

TABLE 3

Rat Pharmacokinetic Data

| Compound No. | % F[b] |
|---|---|
| AA-01 | +++ |
| AA-02 | +++ |
| AA-04 | +++ |
| AA-06 | ++ |
| AA-08 | +++ |
| AA-17 | +++ |

[b]% Bioavailability (% F): 0-10% +; 11-30% ++; 31-100% +++

The bioavailability (% F) in rats of the majority of the PPPT compounds tested is greater than 30%.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

References

A number of publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Andrews, R. C., et al., 2003, "Effects of the 11beta-hydroxysteroid dehydrogenase inhibitor carbenoxolone on insulin sensitivity in men with type 2 diabetes," *J. Clin. Endocrinol. Metab.*, Vol. 88, pp. 285-291.

Christy, C., et al., 2003, "Glucocorticoid action in mouse aorta; localisation of 11β-hydroxysteroid dehydrogenase type 2 and effects on responses to glucocorticoids in vitro," *Hypertension*, Vol. 42, pp. 580-587.

Cooper, M. S., et al., 2000, "Expression and functional consequences of 11β-hydroxysteroid dehydrogenase activity in human bone," *Bone*, Vol. 27, pp. 375-381.

Eckhardt et al., 2010, "Aryl- and Heteroarylcarbonyl derivatives of substituted nortropanes, medicaments containing such compounds and their use", international patent publicaton number WO 2010/023161 A1 published 4 Mar. 2010.

Hadoke, P. W. F., et al., 2001, "Endothelial cell dysfunction in mice after transgenic knockout of type 2, but not type 1, 11β-hydroxysteroid dehydrogenase," *Circulation*, Vol. 104, pp. 2832-2837.

Kotelevtsev, Y. V., et al., 1997, "11β-Hydroxysteroid dehydrogenase type 1 knockout mice show attenuated glucocorticoid inducible responses and resist hyperglycaemia on obesity and stress," *Proc. Natl. Acad. Sci.*, Vol. 94, pp. 14924-14929

Masuzaki, H., et al., 2001, "A Transgenic Model of Visceral Obesity and the Metabolic Syndrome," *Science*, Vol. 294, pp. 2166-2170.

Moisan, M. P., et al., 1990, "11 beta-hydroxysteroid dehydrogenase bioactivity and messenger RNA expression in rat forebrain: localization in hypothalamus, hippocampus, and cortex," *Endocrinology*, Vol. 127, pp. 1450-1455.

Morton, N. M., et al., 2001, "Improved lipid and lipoprotein profile, hepatic insulin sensitivity, and glucose tolerance in 11β-hydroxysteroid dehydrogenase type 1 null mice," *J. Biol. Chem.*, Vol. 276, pp. 41293-41300.

Morton, N. M., et al., 2004, "Novel adipose tissue-mediated resistance to diet-induced visceral obesity in 11β-hydroxysteroid dehydrogenase type 1 deficient mice," *Diabetes*, Vol. 53, pp. 931-938.

Paterson, J. M., et al., 2004, "Metabolic syndrome without obesity: hepatic overexpression of 11β-hydroxysteroid dehydrogenase type 1 in transgenic mice," *Proc. Natl. Acad. Sci.*, Vol. 101, pp. 7088-7093).

Rask, E., et al., 2001, "Tissue-specific dysregulation of cortisol metabolism in human obesity," *J. Clin. Endocrinol. Metab.*, Vol. 86, pp. 1418-1421.

Rauz, S., et al., 2001, "Expression and putative role of 11 beta-hydroxysteroid dehydrogenase isozymes within the human eye," *Investigative Opthalmology & Visual Science*, Vol. 42, pp. 2037-2042.

Sandeep, T. C., et al., 2004, "11β-hydroxysteroid dehydrogenase inhibition improves cognitive function in healthy elderly men and type 2 diabetics," *Proc. Natl. Acad. Sci.*, Vol. 101, pp. 6734-6739.

Seckl, J. R., Walker, B. R., 2001, "11β-Hydroxysteroid dehydrogenase type 1-a tissue-specific amplifier of glucocorticoid action," *Endocrinology*, Vol. 142, pp. 1371-1376.

Small, G. R., et al., 2005, "Preventing local regeneration of glucocorticoids by 11β-hydroxysteroid dehydrogenase type 1 enhances angiogenesis," *Proc. Natl. Acad. Sci.*, Vol. 102, pp. 12165-12170.

Walker, B. R., et al., 1991, "11β-Hydroxysteroid dehydrogenase in vascular smooth muscle and heart: implications for cardiovascular responses to glucocorticoids," *Endocrinology*, Vol. 129, pp. 3305-3312.

Walker, B. R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, Vol. 80, pp. 3155-3139.

Yau, J. L. W., et al., 2001, "Lack of tissue glucocorticoid reactivation in 11β-hydroxysteroid dehydrogenase type 1 knockout mice ameliorates age-related learning impairments," *Proc. Natl. Acad. Sci.*, Vol. 98, pp. 4716-4721.

The invention claimed is:

1. A compound of the following formula, or a pharmaceutically acceptable salt thereof:

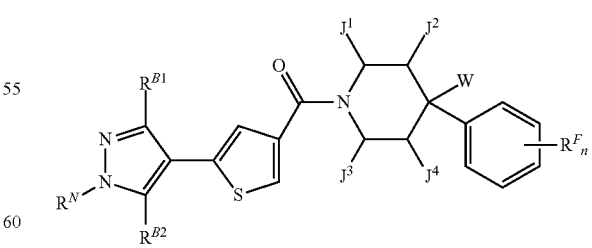

wherein:
—W is —Y;
—Y is independently —$Y^1$, —$Y^2$, —$Y^3$, —$Y^4$, or —$Y^5$;
—$Y^1$ is —OH;
—$Y^2$ is independently —$Y^{2A}$, —$Y^{2B}$, or —$Y^{2C}$;

—$Y^3$ is independently —$Y^{3A}$, —$Y^{3B}$, or —$Y^{3C}$;
—$Y^4$ is independently —F, —Cl, —Br, or —I;
—$Y^5$ is —CN;
wherein:
—$Y^{2A}$ is —$OR^{YA}$;
—$Y^{2B}$ is —$OR^{YB}$;
—$Y^{2C}$ is —$OR^{YC}$;
—$Y^{3A}$ is —$R^{YA}$;
—$Y^{3B}$ is —$R^{YB}$;
—$Y^{3C}$ is —$R^{YC}$;
wherein:
each —$R^{YA}$ is saturated aliphatic $C_{1-6}$alkyl;
each —$R^{YB}$ is saturated aliphatic halo-$C_{1-6}$alkyl;
each —$R^{YC}$ is saturated aliphatic hydroxy-$C_{1-6}$alkyl;
and wherein:
each of -$J^1$, -$J^2$, -$J^3$, and -$J^4$ is —H;
or each of -$J^2$ and -$J^4$ is —H; and -$J^1$ and -$J^3$ taken together form —$CH_2$— or —$CH_2CH_2$—;
or each of -$J^1$ and -$J^3$ is —H; and -$J^2$ and -$J^4$ taken together form —$CH_2$— or —$CH_2CH_2$—;
or each of -$J^2$ and -$J^3$ is —H; and -$J^1$ and -$J^4$ taken together form —$CH_2$— or —$CH_2CH_2$—;
and wherein:
—$R^N$ is independently —H or —$R^{NN}$;
—$R^{NN}$ is saturated aliphatic $C_{1-6}$alkyl;
and wherein:
—$R^{B1}$ is independently —H or —$R^{BB}$;
—$R^{B2}$ is independently —H or —$R^{BB}$;
wherein:
each —$R^{BB}$ is independently —$RB^{BB1}$, —$R^{BB2}$, or —$R^{BB3}$;
wherein:
each —$R^{BB1}$ is saturated aliphatic $C_{1-6}$alkyl, and is optionally substituted with one or more substituents selected from —F, —OH, —$OR^{BBB}$, —$OCH_2F$, —$OCHF_2$, —$OCF_3$, —$NH_2$, —$NHR^{BBB}$, and —$NR^{BBB}_2$; wherein each —$R^{BBB}$ is saturated aliphatic $C_{1-4}$alkyl;
each —$R^{BB2}$ is independently —F, —Cl, —Br, or —I;
each —$R^{BB3}$ is —CN;
and wherein:
n is independently 0, 1, 2, 3, 4, or 5;
each —$R^F$ is independently —$R^Z$, —F, —Cl, —Br, —I, —$CF_3$, —OH, —$OR^Z$, —$OCF_3$, —$SR^Z$, —$S(=O)_2R^Z$, or —CN; and
each —$R^Z$ is saturated aliphatic $C_{1-6}$alkyl, and is optionally substituted with one or more substituents selected from —F, —Cl, —OH, —$OR^{ZZ}$, —$OCH_2F$, —$OCHF_2$, and —$OCF_3$; wherein each —$R^{ZZ}$ is saturated aliphatic $C_{1-4}$alkyl.

2. A compound according to claim 1, wherein:
—$Y^1$ is —OH;
—$Y^2$ is —$^{2A}$;
—$Y^3$ is —$Y^{3A}$ or —$Y^{3C}$;
—$Y^4$ is —F; and
—$Y^5$ is —CN;
—$Y^{2A}$ is —$OR^{YA}$;
—$Y^{3A}$ is —$R^{YA}$;
—$Y^{3C}$ is —$R^{YC}$;
each —$R^{YA}$ is -Me; and
—$R^{Yc}$ is —$CH_2OH$.

3. A compound according to claim 2, wherein —Y is —$Y^1$ or —$Y^4$.

4. A compound according to claim 2, wherein:
each of -$J^1$, -$J^2$, -$J^3$, and -$J^4$ is —H; or
each of -$J^2$ and -$J^4$ is —H, and -$J^1$ and -$J^3$ taken together form —$CH_2CH_2$—; or
each of -$J^1$ and -$J^3$ is —H; and -$J^2$ and -$J^4$ taken together form —$CH_2CH_2$—.

5. A compound according to claim 3, wherein:
each of -$J^1$, -$J^2$, -$J^3$, and -$J^4$ is —H; or
each of -$J^2$ and -$J^4$ is —H, and -$J^1$ and -$J^3$ taken together form —$CH_2CH_2$—; or
each of -$J^1$ and -$J^3$ is —H; and -$J^2$ and -$J^4$ taken together form —$CH_2CH_2$—.

6. A compound according to claim 2, wherein:
each of -$J^1$, -$J^2$, -$J^3$, and -$J^4$ is —H.

7. A compound according to claim 3, wherein:
each of -$J^1$-$J^2$, -$J^3$, and -$J^4$ is —H.

8. A compound according to claim 2, wherein:
—$R^{NN}$ is saturated aliphatic $C_{1-4}$alkyl;
each —$R^{BB1}$ is unsubstituted saturated aliphatic $C_{1-4}$alkyl; and
each —$R^{BB2}$ is —F or —Cl.

9. A compound according to claim 8, wherein each —$R^{BB}$ is —$R^{BB1}$.

10. A compound according to claim 3, wherein:
—$R^{NN}$ is saturated aliphatic $C_{1-4}$alkyl; and
each —$R^{BB1}$ is unsubstituted saturated aliphatic $C_{1-4}$alkyl; and
each —$R^{BB2}$ is —F or —Cl.

11. A compound according to claim 10, wherein each —$R^{BB}$ is —$R^{BB1}$.

12. A compound according to claim 5, wherein:
—$R^{NN}$ is saturated aliphatic $C_{1-4}$alkyl;
each —$R^{BB1}$ is unsubstituted saturated aliphatic $C_{1-4}$alkyl; and
each —$R^{BB2}$ is —F or —Cl.

13. A compound according to claim 12, wherein each —$R^{BB}$ is —$R^{BB1}$.

14. A compound according to claim 2, wherein:
—$R^N$ is —H;
—$R^{B1}$ is —H; and
—$R^{B1}$ is —H.

15. A compound according to claim 3, wherein:
—$R^N$ is —H;
—$R^{B1}$ is —H; and
—$R^{B2}$ is —H.

16. A compound according to claim 5, wherein:
—$R^N$ is —H;
—$R^{B1}$ is —H; and
—$R^{B2}$ is —H.

17. A compound according to claim 2, wherein:
n is independently 0, 1, 2, or 3; and
each —$R^F$ is independently —F, —Cl, -Me, -Et, —OH, —OMe, —OEt, —$CF_3$, —$OCF_3$, or —CN.

18. A compound according to claim 2, wherein:
n is independently 0, 1, or 2; and
each —$R^F$ is independently —F, —Cl, -Me, -Et, —OH, —OMe, —OEt, —$CF_3$, —$OCF_3$, or —CN.

19. A compound according to claim 3, wherein:
n is independently 0, 1, or 2; and
each —$R^F$ is independently —F, —Cl, -Me, -Et, —OH, —OMe, —OEt, —$CF_3$, —$OCF_3$, or —CN.

20. A compound according to claim 5, wherein:
n is independently 0, 1, or 2; and
each —$R^F$ is independently —F, —Cl, -Me, -Et, —OH, —OMe, —OEt, —$CF_3$, —$OCF_3$, or —CN.

21. A compound according to claim 9, wherein:
n is independently 0, 1, or 2; and
each 13 $R^F$ is independently —F, —Cl, -Me, -Et, —OH, —OMe, —OEt, —$CF_3$, —$OCF_3$, or —CN.

22. A compound according to claim 11, wherein:

n is independently 0, 1, or 2; and each —R$^F$ is independently —F, —Cl, -Me, -Et, —OH, —OMe, —OEt, —CF$_3$, —OCF$_3$, or —CN.

23. A compound according to claim 13, wherein:

n is independently 0, 1, or 2; and each —R$^F$ is independently —F, —Cl, -Me, -Et, —OH, —OMe, —OEt, —CF$_3$, —OCF$_3$, or —CN.

24. A compound according to claim 14, wherein:

n is independently 0, 1, or 2; and each —R$^F$ is independently —F, —Cl, -Me, -Et, —OH, —OMe, —OEt, —CF$_3$, —OCF$_3$, or —CN.

25. A compound according to claim 15, wherein:

n is independently 0, 1, or 2; and each —R$^F$ is independently —F, —Cl, -Me, -Et, —OH, —OMe, —OEt, —CF$_3$, —OCF$_3$, or —CN.

26. A compound according to claim 16, wherein:

n is independently 0, 1, or 2; and each —R$^F$ is independently —F, —Cl, -Me, -Et, —OH, —OMe, —OEt, —CF$_3$, —OCF$_3$, or —CN.

27. A compound according to claim 1, selected from compounds of the following formulae or a pharmaceutically acceptable salt thereof:

(AA-11), (AA-12), (AA-13), (AA-14), (AA-15), (AA-16), (AA-17), (AA-18), (AA-19), (AA-20), (AA-21), (AA-22), (AA-23), (AA-24)

(AA-25)
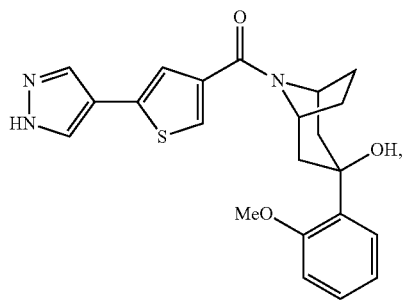
(AA-31)
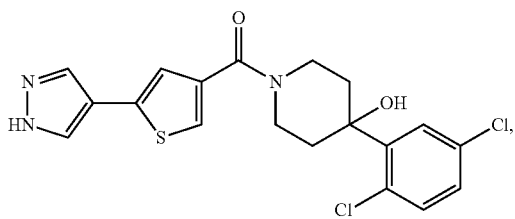
(AA-26)
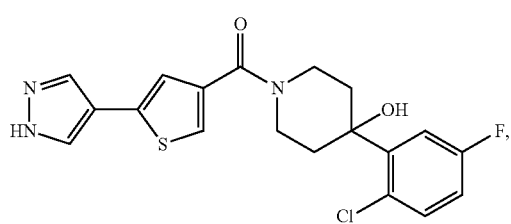
(AA-32)
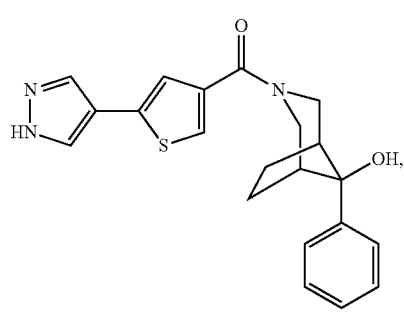
(AA-27)
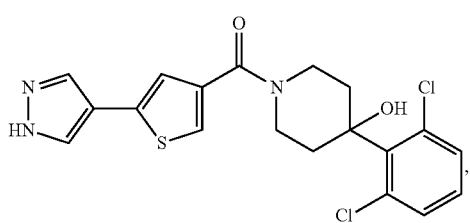
(AA-33)
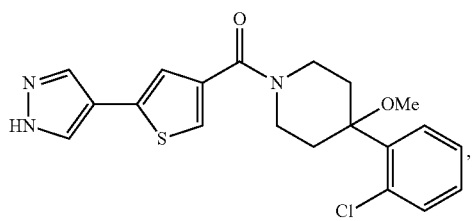
(AA-28)
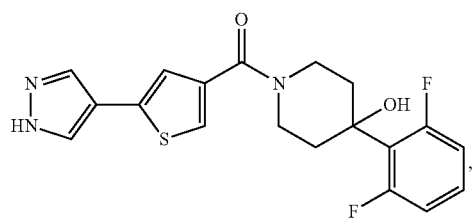
(AA-34)
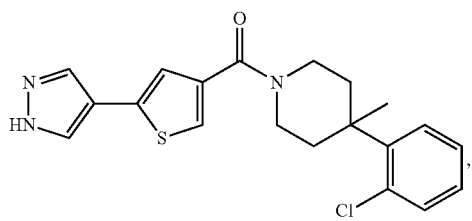
(AA-29)
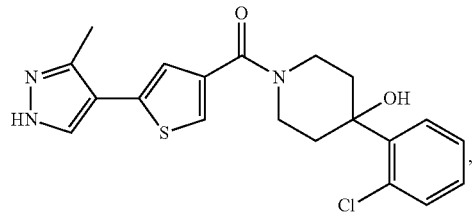
(AA-35)
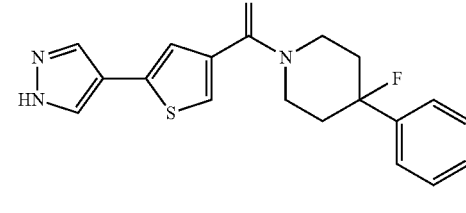
(AA-30)
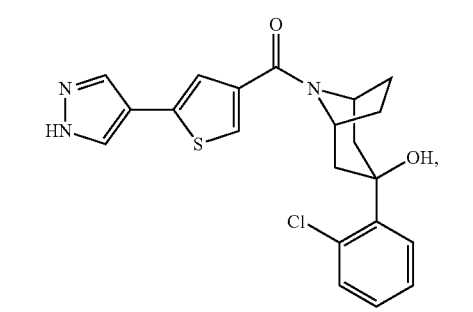
(AA-36)
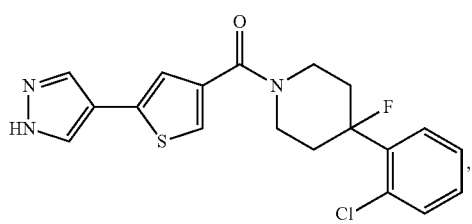

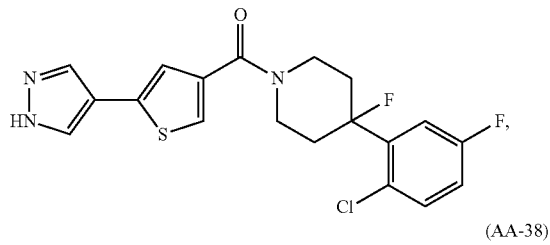
(AA-37)

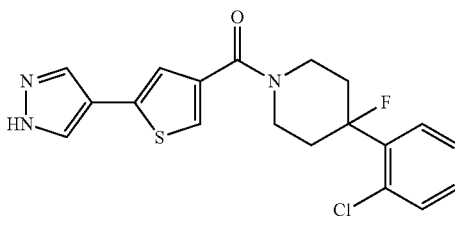
(AA-38)

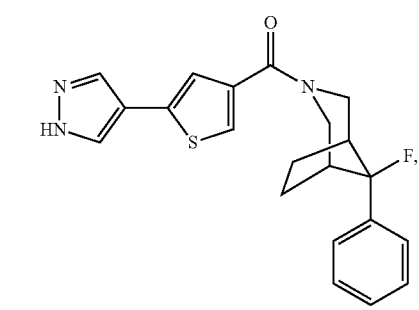
(AA-39)

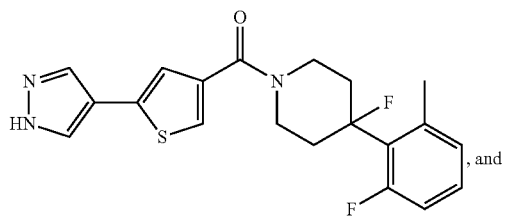
(AA-40)
, and

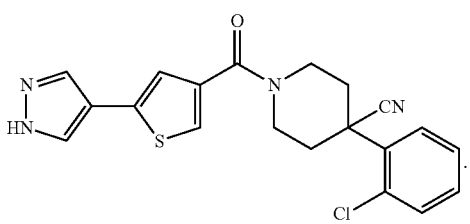
(AA-41)

28. A pharmaceutical composition comprising a compound according to claim 1 and a pharmaceutically acceptable carrier or diluent.

29. A method of preparing a pharmaceutical composition comprising the step of admixing a compound according to claim 1 and a pharmaceutically acceptable carrier or diluent.

30. A method of inhibiting 11 β-hydroxysteroid dehydrogenase type 1 function in a cell, in vitro, comprising contacting the cell with an effective amount of a compound according to claim 1.

* * * * *